United States Patent
Chakraborty et al.

(10) Patent No.: US 9,023,998 B2
(45) Date of Patent: May 5, 2015

(54) NEAR INFRARED FLUOROGEN AND FLUORESCENT ACTIVATING PROTEINS FOR IN VIVO IMAGING AND LIVE-CELL BIOSENSING

(71) Applicant: Carnegie Mellon University, Pittsburgh, PA (US)

(72) Inventors: Subhasish K. Chakraborty, Pittsburgh, PA (US); Mingrui Zhang, Pittsburgh, PA (US); Alan S. Waggoner, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 13/920,775

(22) Filed: Jun. 18, 2013

(65) Prior Publication Data
US 2014/0243509 A1    Aug. 28, 2014

Related U.S. Application Data

(60) Provisional application No. 61/850,872, filed on Feb. 25, 2013, provisional application No. 61/851,789, filed on Mar. 13, 2013.

(51) Int. Cl.
| | | |
|---|---|---|
| C07K 16/44 | (2006.01) | |
| G01N 21/64 | (2006.01) | |
| A61K 49/00 | (2006.01) | |
| C07D 207/46 | (2006.01) | |
| C07C 309/18 | (2006.01) | |
| C07C 251/30 | (2006.01) | |

(52) U.S. Cl.
CPC ........ *G01N 21/6486* (2013.01); *A61K 49/0021* (2013.01); *C07D 207/46* (2013.01); *C07K 16/44* (2013.01); *C07C 309/18* (2013.01); *C07C 251/30* (2013.01); *C07K 2317/515* (2013.01)

(58) Field of Classification Search
None
See application file for complete search history.

(56) References Cited

U.S. PATENT DOCUMENTS

| | | | | |
|---|---|---|---|---|
| 290,891 | A * | 12/1883 | Kern .............................. | 552/114 |
| 2,813,802 | A * | 11/1957 | Ingle et al. ..................... | 428/426 |
| 4,355,023 | A | 10/1982 | Ehrilich et al. | |
| 4,462,334 | A | 7/1984 | Kim | |
| 4,704,692 | A | 11/1987 | Ladner | |
| 4,946,778 | A | 8/1990 | Ladner et al. | |
| 2008/0274907 | A1* | 11/2008 | Beacham et al. ............. | 506/7 |
| 2011/0159519 | A1 | 6/2011 | Schmidt et al. | |
| 2012/0058494 | A1* | 3/2012 | Bruchez et al. .............. | 435/7.31 |

FOREIGN PATENT DOCUMENTS

| | | | |
|---|---|---|---|
| WO | WO 2008/092041 A3 | 7/2008 | |
| WO | WO 2010/096388 A2 | 8/2010 | |
| WO | WO 2011/150079 A1 | 12/2011 | |

OTHER PUBLICATIONS

Lipinski, Christopher A. et al; "Experimental and computational appropaches to estiamte solubility and permeability in drug discovery and development settings." Adv. Drug. Del. Rev. (1997) 23 p. 3-25.*
Zahnd, Christian et al, "Directed in vitro evolution and crystallographic analysis of a peptide binding single chain antibody fragment (scfv) with low picomolar affinity." J. Biol. Chem. (2004) 279(18) p. 18870-18877.*
Jones, Simon W. et al, "Characterisation of cell-penetrating peptide-mediated peptide delivery." Brit. J. Pharmacol. (2005) 145 p. 1093-1102.*
The web page for Photon Control, http://www.photon-control.com/spectroscopy.html?gclid=COip2Zyzl78CFWrl7AodxwoA1w, downloaded Jun. 26, 2014.*
The web page for Excelitas technology's NIR specrophotometers, http://www.excelitas.com/pages/product/Near-Infrared-NIR-750-nm-950-nm.aspx, downloaded Jun. 26, 2014.*
Nature magazine's definition of NIR, http://www.nature.com/subjects/near-infrared-spectroscopy, downloaded Jun. 26, 2014.*
Brey, L. A. et al, "High pressure studies of the effect of viscosity on fluorescence efficiency in crystal violet and auramine o." J. Chem. Phys. (1977) 67(6) p. 2648-2650.*
Wayne, Richard P; Principles and applications of photochemistry, 1988, isbn0-19-855233-5.*
Mathew, S. et al, "Quenching of fluorescence by crystal violet and its use to differentiate between surface bound and internalized bacteria." Proc. SPIE (2008) 6791, p. 67910C-1-67910C-4.*

(Continued)

*Primary Examiner* — Maury Audet
*Assistant Examiner* — Fred Reynolds
(74) *Attorney, Agent, or Firm* — K&L Gates LLP

(57) ABSTRACT

Tissue slices and whole organisms offer substantial challenges to fluorescence imaging. Autofluorescence and absorption via intrinsic chromophores, such as flavins, melanin, and hemoglobins, confound and degrade output from all fluorescent tags. An "optical window," farther red than most autofluorescence sources and in a region of low hemoglobin and water absorbance, lies between 650 and 900 nm. This valley of relative optical clarity is an attractive target for fluorescence-based studies within tissues, intact organs, and living organisms. Novel fluorescent tags were developed herein, based upon a genetically targeted fluorogen activating protein and cognate fluorogenic dye that yields emission with a peak at 733 nm exclusively when complexed as a "fluoromodule". This tool improves substantially over previously described far-red/NIR fluorescent proteins in terms of brightness, wavelength, and flexibility by leveraging the flexibility of synthetic chemistry to produce novel chromophores.

13 Claims, 27 Drawing Sheets

(56) References Cited

OTHER PUBLICATIONS

The Sigma Aldrich catalog entry C3886, crystal violet: http://www.sigmaaldrich.com/catalog/product/sigma/c3886?lang=en&region=US, downloaded Jun. 26, 2014.*

Pham, Wellington et al, "An azulene dimer as a near-infrared quencher." Angew. Chem. Int. Ed. (2002) 41(19) p. 3659-3663.*

Monet, Xavier et al; "Tomographic fluroescence mapping of tumor targets." Cancer. Res. (2005) 65 p. 6330-6336.*

Kelly, Kimberly A. et al; "Novel peptide sequence ("iq-tag") with high affinity for nir fluorochromes allows protein and cell specific labeling for in vivo imaging." PLoS One (2007) 2(7) e665, p. 1-9.*

Von Schmidt et al, "Uber die vinylenhomologen der di- und triphenylmethanefarbstoffe, III." Justus Liebigs Annalen der Chemie (1959) 623 p. 204-216.*

Carmody, An Easily Prepared Wide Range Buffer Series, Journal of Chemical Education, vol. 38, No. 11, pp. 559-560 (1961).

Chao, Herbert S. I., Improved synthesis of trans-4-(diethylamino)cinnamaldehyde, Synthetic Communications, 18(14), pp. 1641-1650 (1988).

Chao, et al., Isolating and engineering human antibodies using yeast surface display, Nature Protocols, vol. 1, No. 2, pp. 755-768 (2006).

Chou, et al., Expression of Chimeric Monomer and Dimer Proteins on the Plasma Membrane of Mammalian Cells, Biotechnology and Engineering, vol. 65, No. 2, (1999).

Duxbury, D., The Photochemistry and Photophysics of Triphenylmethane Dyes in Solid and Liquid Media, Chem. Rev., 93, 381-433, (1993).

Furstenberg et al.,Ultrafast Excited-State Dynamics of DNA Fluorescent Intercalators: New Insight into the Fluorescence Enhancement Mechanism, JACS, 128, 7661-7669, (2006).

Grover A. et al, Genetically Encoded pH Sensor for Tracking Surface Proteins through Endocytosis, Angewante Chemie, published online: Mar. 29, 2012.

Hochman et al., An Active Antibody Fragment (Fv) Composed of the Variable Portions of Heavy and Light Chains, Biochemistry, 12, 1130, 1973.

Magde et al., Picosecond Internal Conversion in Crystal Violet, Chem. Phys. Letters, 24, 144-148, (1974).

Mujumdar, et al., Cyanine Dyes Labeling Reagents: Sulfoindocyanine Succinimidyl Esters, Bioconjugate Chemistry, vol. 4, No. 2, 105-111 (1993).

Senutovitch et al., A Variable Light Domain Fluorogen Activating Protein Homodimerizes to Activate Dimethylindole Red, Biochemistry, 51, 2471-2485 (2012).

Sharon et al., Preparation of Fv Fragment from the Mouse Myeloma XRPC-25 Immunoglobulin Possessing Anti-Dinitrophenyl Activity, Biochemistry, vol. 15, No. 7, pp. 1591-1594, 1976.

Silva et al., Experimental and Computational Investigation of Unsymmetrical Cyanine Dyes: Understanding Torsionally Responsive Fluorogenic Dyes, JACS, vol. 129, pp. 5710-5718, (2007).

Szent-Gyorgyi C. et al., Fluorogen-activating single-chain antibodies for imaging cell surface proteins, Nat Biotechnol,. 26:235-240, (2008).

Williams, Winfield and Miller, Relative Fluorescent Quantum Yield Using a Computer-controlled Luminescence Spectrometer, Analyst, vol. 108, 1067-1071 (1983).

Wu Y. et al., Discovery of regulators of receptor internalization by high throughput cytometry, Mol. Pharmacol. (2012) PMID: 22767611.

Würth, et al., Integrating Sphere Setup for the Traceable Measurement of Absolute Photoluminescence Quantum Yields in the Near Infrared, Analytical Chemistry, 84, 1345-1352 (2012).

* cited by examiner

SKC602

SKC728

FIGURE 9A

TABLE 9A

Extracellular Display Vector pOIdL9.2N
The open reading frame is displayed between line breaks in bold text and includes the following annotated features. Igκ secretion signal is italicized. The nucleotide sequence encoding dL9.2 is capitalized. The transmembrane domain of CD80, which tethers the FAP to the extracellular face of the plasma membrane, is underlined.

(SEQ. ID. NO. 7)
tagttattaatagtaatcaattacggggtcattagttcatagcccatatatggagttccgcgttacataacttacggtaaatggcccgcctggctg
accgcccaacgaccccccgcccattgacgtcaataatgacgtatgttcccatagtaacgccaatagggactttccattgacgtcaatgggtgg
agtatttacggtaaactgcccacttggcagtacatcaagtgtatcatatgccaagtacgccccctattgacgtcaatgacggtaaatggcccg
cctggcattatgcccagtacatgaccttatgggactttcctacttggcagtacatctacgtattagtcatcgctattaccatggtgatgcggttttg
gcagtacatcaatgggcgtggatagcggtttgactcacggggatttccaagtctccacccattgacgtcaatgggagtttgttttggcacca
aaatcaacgggactttccaaaatgtcgtaacaactccgccccattgacgcaaatgggcggtaggcgtgtacggtgggaggtctatataagc
agagctggtttagtgaaccgtcagatccgctagcgctaccggtcgccacc
*atggagacagacacactcctgctatgggtactgctgctctgggttccaggttccactggtgac*tatccatatgatgttccagattatgctt
ctagcTCTTACGAATTAACACAACCTCCATCTGTTTCTGTTTCTCCAGGTCAAACT
GCTAGAATTACTTGTTCTGGTGATGCTTTGCCAAAACAATACACTTACTGGTAT
CAACAAAAAGCTGGTCAAGCTCCAGTTTTGGTTATTTATAAAGATACTGAAAGA
CCATCTGGTATTCCAGAAAGATTCTCAGGTACTTCTTCTGGTACTACTGCTACT
TTGACTATTTCTGGTGTTCAAGCTGAAGATGAAGCTGATTATTATTGTCAATCT
GCTGATTCTTCTGGTTCTTATGTATTTTTCGGTGGTGGTACTAAAGTTACTGTTT
TGTCTGGTGGAGGAGGCCCAGGTGGCGGTTCAGGTGGAGGTTCTGGCGGAGG
TTCTGGTGGAGGTTCCTATGAGTTGACTCAGCCACCCTCGGTGTCAGTGTCCCC
AGGACAGACGGCCAGGATCACCTGCTCTGGAGATGCATTGCCAAAGCAATATA
CTTATTGGTACCAGCAGAAGGCAGGCCAGGCCCCTGTCTTGGTGATATATAAA
GACACTGAGAGGCCCTCAGGGATCCCTGAGCGATTCTCTGGTACCAGTTCAGG
GACAACAGTCACATTGACCATCAGTGGAGTCCAGGCAGAAGACGAGGCTGACT
ATTACTGTCAATCAGCAGACAGCAGTGGTTCCTATGTTTTCTTCGGCGGAGGGA
CCAAGGTGACCGTACTATCCggaggcggtgggaagaagttcccccagaagaccctcctgatagcaagaaca
cacttgtgctctttggggcaggattcggcgcagtaataacagtcgtcgtcatcgttgtcatcatcaaatgcttctgtaagcacagaag
ctgtttcagaagaaatgaggcaagcagagaaacaaacaacagccttaccttcgggcctgaagaagcattagctgaacagaccgt
cttccttactagttaa
tagcccgggatccaccggatctagataactgatcataatcagccataccacatttgtagaggttttacttgctttaaaaaacctcccacacctcc
ccctgaacctgaaacataaaatgaatgcaattgttgttgttaacttgtttattgcagcttataatggttacaaataaagcaatagcatcacaaatttc
acaaataaagcatttttttcactgcattctagttgtggtttgtccaaactcatcaatgtatcttaacgcgtaaattgtaagcgttaatatttttgttaaaat
tcgcgttaaattttttgttaaatcagctcattttttaaccaataggccgaaatcggcaaaatcccttataaatcaaaagaatagaccgagataggt
tgagtgttgttccagtttggaacaagagtccactattaaagaacgtggactccaacgtcaaagggcgaaaaaccgtctatcagggcgatggc
ccactacgtgaaccatcaccctaatcaagttttttggggtcgaggtgccgtaaagcactaaatcggaaccctaaagggagcccccgatttag
agcttgacggggaaagccggcgaacgtggcgagaaaggaagggaagaaagcgaaaggagcgggcgctagggcgctggcaagtgta
gcggtcacgctgcgcgtaaccaccacacccgccgcgcttaatgcgccgctacagggcgcgtcaggtggcacttttcgggggaaatgtgcg
cggaacccctatttgtttatttttctaaatacattcaaatatgtatccgctcatgagacaataacccctgataaatgcttcaataatattgaaaaagga
agagtcctgaggcggaaagaaccagctgtggaatgtgtgtcagttagggtgtggaaagtccccaggctccccagcaggcagaagtatgc

FIGURE 9B

TABLE 9A continued (SEQ. ID. NO. 7, continued)
aaagcatgcatctcaattagtcagcaaccaggtgtggaaagtccccaggctccccagcaggcagaagtatgcaaagcatgcatctcaatta
gtcagcaaccatagtcccgcccctaactccgcccatcccgcccctaactccgcccagttccgcccattctccgcccatggctgactaattttt
tttatttatgcagaggccgaggccgcctcggcctctgagctattccagaagtagtgaggaggcttttttggaggcctaggcttttgcaaagatc
gatcaagagacaggatgaggatcgtttcgcatgattgaacaagatggattgcacgcaggttctccggccgcttgggtggagaggctattcg
gctatgactgggcacaacagacaatcggctgctctgatgccgccgtgttccggctgtcagcgcaggggcgcccggttcttttttgtcaagacc
gacctgtccggtgccctgaatgaactgcaagacgaggcagcgcggctatcgtggctggccacgacgggcgttccttgcgcagctgtgctc
gacgttgtcactgaagcgggaagggactggctgctattgggcgaagtgccggggcaggatctcctgtcatctcaccttgctcctgccgaga
aagtatccatcatggctgatgcaatgcggcggctgcatacgcttgatccggctacctgcccattcgaccaccaagcgaaacatcgcatcga
gcgagcacgtactcggatggaagccggtcttgtcgatcaggatgatctggacgaagagcatcaggggctcgcgccagccgaactgttcg
ccaggctcaaggcgagcatgcccgacggcgaggatctcgtcgtgacccatggcgatgcctgcttgccgaatatcatggtggaaaatggcc
gcttttctggattcatcgactgtggccggctgggtgtggcggaccgctatcaggacatagcgttggctacccgtgatattgctgaagagcttg
gcggcgaatgggctgaccgcttcctcgtgctttacggtatcgccgctcccgattcgcagcgcatcgccttctatgccttcttgacgagttctt
ctgagcgggactctggggttcgaaatgaccgaccaagcgacgcccaacctgccatcacgagatttcgattccaccgccgccttctatgaaa
ggttgggcttcggaatcgttttccgggacgccggctggatgatcctccagcgcggggatctcatgctggagttcttcgcccaccctaggg
gaggctaactgaaacacggaaggagacaataccggaaggaacccgcgctatgacggcaataaaaagacagaataaaacgcacggtgtt
gggtcgtttgttcataaacgcggggttcggtcccagggctggcactctgtcgataccccaccgagacccattggggccaatacgccgcg
tttcttccttttccccaccccacccccaagttcgggtgaaggcccagggctcgcagccaacgtcggggcggcaggccctgccatagcctc
aggttactcatatatactttagattgatttaaaacttcattttaattaaaaggatctaggtgaagatcctttttgataatctcatgaccaaaatcccttt
aacgtgagttttcgttccactgagcgtcagaccccgtagaaaagatcaaaggatcttcttgagatcctttttctgcgcgtaatctgctgcttgc
aaacaaaaaaaccaccgctaccagcggtggtttgtttgccggatcaagagctaccaactcttttccgaaggtaactggcttcagcagagcg
cagataccaaatactgtccttctagtgtagccgtagttaggccaccacttcaagaactctgtagcaccgcctacatacctcgctctgctaatcct
gttaccagtggctgctgccagtggcgataagtcgtgtcttaccgggttggactcaagacgatagttaccggataaggcgcagcggtcgggc
tgaacggggggttcgtgcacacagcccagcttggagcgaacgacctacaccgaactgagatacctacagcgtgagctatgagaaagcgc
cacgcttcccgaaggggagaaaggcggacaggtatccggtaagcggcagggtcggaacaggagagcgcacgagggagcttccagggg
gaaacgcctggtatctttatagtcctgtcgggtttcgccacctctgacttgagcgtcgatttttgtgatgctcgtcaggggggcggagcctatg
gaaaaacgccagcaacgcggcctttttacggttcctggccttttgctggccttttgctcacatgttctttcctgcgttatcccctgattctgtggat
aaccgtattaccgccatgcat

FIGURE 9C

TABLE 9B

Extracellular Display Vector pOIdL9.5N
The open reading frame is displayed between line breaks in bold text and includes the following annotated features. Igκ secretion signal is italicized. The nucleotide sequence encoding dL9.5 is capitalized. The transmembrane domain of CD80, which tethers the FAP to the extracellular face of the plasma membrane, is underlined.

(SEQ. ID. NO. 8)
tagttattaatagtaatcaattacggggtcattagttcatagcccatatatggagttccgcgttacataacttacggtaaatggcccgcctggctg
accgcccaacgaccccgcccattgacgtcaataatgacgtatgttcccatagtaacgccaatagggactttccattgacgtcaatgggtgg
agtatttacggtaaactgcccacttggcagtacatcaagtgtatcatatgccaagtacgccccctattgacgtcaatgacggtaaatggcccg
cctggcattatgcccagtacatgaccttatgggacttcctacttggcagtacatctacgtattagtcatcgctattaccatggtgatgcggttttg
gcagtacatcaatgggcgtggatagcggtttgactcacggggatttccaagtctccaccccattgacgtcaatgggagtttgttttggcacca
aaatcaacgggactttccaaaatgtcgtaacaactccgccccattgacgcaaatgggcggtaggcgtgtacggtgggaggtctatataagc
agagctggtttagtgaaccgtcagatccgctagcgctaccggtcgccacc
*atggagacagacacactcctgctatgggtactgctgctctgggttccaggttccactggtgac*atccatatgatgttccagattatgctt
ctagc**TCTTACGAATTAACACAACCTCCATCTGTTTCTGTTTCTCCAGGTCAAACT
GCTAGAATTACTTGTTCTGGTGATGCTTTGCCAAAACAATACACTTACTGGTAT
CAACAAAAAGCTGGTCAAGCTCCAGTTTTGGTTATTTATAAAGATACTGAAAGA
CCATCTGGTATTCCAGAAAGATTCTCAGGTACTTCTTCTGGTACTACTGCTACT
TTGACTATTTCTGGTGTTCAAGCTGAAGATGAAGCTGATTATTATTGTCAATCT
GCTGATTCTTCTGGTTCTCATGTATTTTTCGGTGGTGGTACTAAAGTTACTGTT
TTGTCTGGTGGAGGAGGCCCAGGTGGCGGTTCAGGTGGAGGTTCTGGCGGAG
GTTCTGGTGGAGGTTCCTATGAGTTGACTCAGCCACCCTCGGTGTCAGTGTCC
CCAGGACAGACGGCCAGGATCACCTGCTCTGGAGATGCATTGCCAAAGCAATA
TACTTATTGGTACCAGCAGAAGGCAGGCCAGGCCCCTGTCTTGGTGATATATA
AAGACACTGAGAGGCCCTCAGGGATCCCTGAGCGATTCTCTGGTACCAGTTCA
GGGACAACAGCCACATTGACCATCAGTGGAGTCCAGGCAGAAGACGAGGCTGA
CTATTACTGTCAATCAGCAGACAGCAGTGGTTCCCACGTTTTCTTCGGCGGAGG
GACCAAGGTGACCGTACTATCC**ggaggcggtgggaagaagttcccccagaagaccctcctgatagcaaga
acaca<u>cttgtgctctttggggcaggattcggcgcagtaataacagtcgtcgtcatcgttgtcatcatca</u>aatgcttctgtaagcacag
aagctgtttcagaagaaatgaggcaagcagagaaacaaacaacagccttaccttcgggcctgaagaagcattagctgaacagac
cgtcttccttactagttaa
tagcccgggatccaccggatctagataactgatcataatcagccataccacatttgtagaggttttacttgctttaaaaaacctcccacacctcc
ccctgaacctgaaacataaaatgaatgcaattgttgttgttaacttgtttattgcagcttataatggttacaaataaagcaatagcatcacaaatttc
acaaataaagcatttttttcactgcattctagttgtggtttgtccaaactcatcaatgtatcttaacgcgtaaattgtaagcgttaatatttttgttaaaat
tcgcgttaaattttgttaaatcagctcatttttaaccaataggccgaaatcggcaaaatcccttataaatcaaaagaatagaccgagataggt
tgagtgttgttccagtttggaacaagagtccactattaaagaacgtggactccaacgtcaaagggcgaaaaccgtctatcagggcgatggc
ccactacgtgaaccatcaccctaatcaagttttttggggtcgaggtgccgtaaagcactaaatcggaaccctaaagggagccccgatttag
agcttgacggggaaagccggcgaacgtggcgagaaaggaagggaagaaagcgaaaggagcgggcgctagggcgctggcaagtgta
gcggtcacgctgcgcgtaaccaccacacccgccgcgcttaatgcgccgctacagggcgcgtcaggtggcacttttcggggaaatgtgcg
cggaacccctatttgtttatttttctaaatacattcaaatatgtatccgctcatgagacaataaccctgataaatgcttcaataatattgaaaaagga
agagtcctgaggcggaaagaaccagctgtggaatgtgtgtcagttagggtgtggaaagtccccaggctccccagcaggcagaagtatgc

FIGURE 9D

TABLE 9B continued (SEQ. ID. NO. 8, continued)
aaagcatgcatctcaattagtcagcaaccaggtgtggaaagtccccaggctccccagcaggcagaagtatgcaaagcatgcatctcaatta
gtcagcaaccatagtcccgcccctaactccgcccatcccgcccctaactccgcccagttccgcccattctccgccccatggctgactaattttt
tttatttatgcagaggccgaggccgcctcggcctctgagctattccagaagtagtgaggaggcttttttggaggcctaggcttttgcaaagatc
gatcaagagacaggatgaggatcgtttcgcatgattgaacaagatggattgcacgcaggttctccggccgcttgggtggagaggctattcg
gctatgactgggcacaacagacaatcggctgctctgatgccgccgtgttccggctgtcagcgcaggggcgcccggttcttttttgtcaagacc
gacctgtccggtgccctgaatgaactgcaagacgaggcagcgcggctatcgtggctggccacgacgggcgttccttgcgcagctgtgctc
gacgttgtcactgaagcgggaagggactggctgctattgggcgaagtgccggggcaggatctcctgtcatctcaccttgctcctgccgaga
aagtatccatcatggctgatgcaatgcggcggctgcatacgcttgatccggctacctgcccattcgaccaccaagcgaaacatcgcatcga
gcgagcacgtactcggatggaagccggtcttgtcgatcaggatgatctggacgaagagcatcaggggctcgcgccagccgaactgttcg
ccaggctcaaggcgagcatgcccgacggcgaggatctcgtcgtgacccatggcgatgcctgcttgccgaatatcatggtggaaaatggcc
gcttttctggattcatcgactgtggccggctgggtgtggcggaccgctatcaggacatagcgttggctacccgtgatattgctgaagagcttg
gcggcgaatgggctgaccgcttcctcgtgctttacggtatcgccgctcccgattcgcagcgcatcgccttctatcgccttcttgacgagttctt
ctgagcgggactctggggttcgaaatgaccgaccaagcgacgcccaacctgccatcacgagatttcgattccaccgccgccttctatgaaa
ggttgggcttcggaatcgttttccgggacgccggctggatgatcctccagcgcggggatctcatgctggagttcttcgcccaccctagggg
gaggctaactgaaacacggaaggagacaataccggaaggaacccgcgctatgacggcaataaaaagacagaataaaacgcacggtgtt
gggtcgtttgttcataaacgcggggttcggtcccagggctggcactctgtcgataccccaccgagacccattggggccaatacgcccgcg
tttcttccttttcccccaccccaccccccaagttcgggtgaaggcccagggctcgcagccaacgtcggggcggcaggccctgccatagcctc
aggttactcatatatactttagattgatttaaaacttcattttaatttaaaaggatctaggtgaagatccttttgataatctcatgaccaaaatcccctt
aacgtgagttttcgttccactgagcgtcagaccccgtagaaaagatcaaaggatcttcttgagatcctttttttctgcgcgtaatctgctgcttgc
aaacaaaaaaaccaccgctaccagcggtggtttgtttgccggatcaagagctaccaactctttttccgaaggtaactggcttcagcagagcg
cagataccaaatactgtccttctagtgtagccgtagttaggccaccacttcaagaactctgtagcaccgcctacatacctcgctctgctaatcct
gttaccagtggctgctgccagtggcgataagtcgtgtcttaccgggttggactcaagacgatagttaccggataaggcgcagcggtcgggc
tgaacggggggttcgtgcacacagcccagcttggagcgaacgacctacaccgaactgagatacctacagcgtgagctatgagaaagcgc
cacgcttcccgaaggagaaaggcggacaggtatccggtaagcggcagggtcggaacaggagagcgcacgagggagcttccagggg
gaaacgcctggtatctttatagtcctgtcgggtttcgccacctctgacttgagcgtcgattttgtgatgctcgtcaggggggcggagcctatg
gaaaaacgccagcaacgcggcctttttacggttcctggccttttgctggccttttgctcacatgttctttcctgcgttatccctgattctgtggat
aaccgtattaccgccatgcat

FIGURE 9E

TABLE 9C

GFP-normalized cytoplasmic FAP expression vector pCYdL9.2eGFP
The open reading frame is displayed between line breaks in bold text and includes the following annotated features. The nucleotide sequence encoding dL9.2 is capitalized. The nucleotide sequence of eGFP is underlined.

(SEQ. ID. NO. 9)
tagttattaatagtaatcaattacggggtcattagttcatagcccatatatggagttccgcgttacataacttacggtaaatggcccgcctggctg
accgcccaacgaccccgcccattgacgtcaataatgacgtatgttcccatagtaacgccaatagggactttccattgacgtcaatgggtgg
agtatttacggtaaactgcccacttggcagtacatcaagtgtatcatatgccaagtacgccccctattgacgtcaatgacggtaaatggcccg
cctggcattatgcccagtacatgaccttatgggactttcctacttggcagtacatctacgtattagtcatcgctattaccatggtgatgcggttttg
gcagtacatcaatgggcgtggatagcggtttgactcacggggatttccaagtctccacccattgacgtcaatgggagtttgttttggcacca
aaatcaacgggactttccaaaatgtcgtaacaactccgccccattgacgcaaatgggcggtaggcgtgtacggtgggaggtctatataagc
agagctggtttagtgaaccgtcagatccgctagcgctaccggtcgccacc
atggccTCTTACGAATTAACACAACCTCCATCTGTTTCTGTTTCTCCAGGTCAAACT
GCTAGAATTACTTGTTCTGGTGATGCTTTGCCAAAACAATACACTTACTGGTAT
CAACAAAAAGCTGGTCAAGCTCCAGTTTTGGTTATTTATAAAGATACTGAAAGA
CCATCTGGTATTCCAGAAAGATTCTCAGGTACTTCTTCTGGTACTACTGCTACT
TTGACTATTTCTGGTGTTCAAGCTGAAGATGAAGCTGATTATTATTGTCAATCT
GCTGATTCTTCTGGTTCTTATGTATTTTTCGGTGGTGGTACTAAAGTTACTGTTT
TGTCTGGTGGAGGAGGCCCAGGTGGCGGTTCAGGTGGAGGTTCTGGCGGAGG
TTCTGGTGGAGGTTCCTATGAGTTGACTCAGCCACCCTCGGTGTCAGTGTCCCC
AGGACAGACGGCCAGGATCACCTGCTCTGGAGATGCATTGCCAAAGCAATATA
CTTATTGGTACCAGCAGAAGGCAGGCCAGGCCCCTGTCTTGGTGATATATAAA
GACACTGAGAGGCCCTCAGGGATCCCTGAGCGATTCTCTGGTACCAGTTCAGG
GACAACAGTCACATTGACCATCAGTGGAGTCCAGGCAGAAGACGAGGCTGACT
ATTACTGTCAATCAGCAGACAGCAGTGGTTCCTATGTTTTCTTCGGCGGAGGGA
CCAAGGTGACCGTACTATCC<u>ggagggcgcgcctctggtggcggagcttctggaggtggttctggcggctctggt</u>
<u>atggtgagcaagggcgaggagctgttcaccggggtggtgcccatcctggtcgagctggacggcgacgtaaacggccacaagttca</u>
<u>gcgtgtccggcgagggcgagggcgatgccacctacggcaagctgaccctgaagttcatctgcaccaccggcaagctgcccgtgcc</u>
<u>ctggcccacctcgtgaccaccctgacctacggcgtgcagtgcttcagccgctaccccgaccacatgaagcagcacgacttcttcaa</u>
<u>gtccgccatgcccgaaggctacgtccaggagcgcaccatcttcttcaaggacgacggcaactacaagacccgcgccgaggtgaa</u>
<u>gttcgagggcgacaccctggtgaaccgcatcgagctgaagggcatcgacttcaaggaggacggcaacatcctggggcacaagct</u>
<u>ggagtacaactacaacagccacaacgtctatatcatggccgacaagcagaagaacggcatcaaggtgaacttcaagatccgcca</u>
<u>caacatcgaggacggcagcgtgcagctcgccgaccactaccagcagaacacccccatcggcgacggccccgtgctgctgcccga</u>
<u>caaccactacctgagcacccagtccgccctgagcaaagaccccaacgagaagcgcgatcacatggtcctgctggagttcgtgacc</u>
<u>gccgccgggatcactctcggcatggacgagctgtacaagtaa</u>
cccgggatccaccggatctagataactgatcataatcagccataccacatttgtagaggttttacttgctttaaaaaacctcccacacctccccc
tgaacctgaaacataaaatgaatgcaattgttgttgttaacttgtttattgcagcttataatggttacaaataaagcaatagcatcacaaatttcaca
aataaagcattttttcactgcattctagttgtggtttgtccaaactcatcaatgtatcttaacgcgtaaattgtaagcgttaatatttgttaaaattcg
cgttaaattttgttaaatcagctcattttttaaccaataggccgaaatcggcaaaatcccttataaatcaaaagaatagaccgagatagggttga
gtgttgttccagtttggaacaagagtccactattaaagaacgtggactccaacgtcaaagggcgaaaaaccgtctatcagggcgatggccc
actacgtgaaccatcaccctaatcaagttttttggggtcgaggtgccgtaaagcactaaatcggaaccctaaagggagcccccgatttagag

FIGURE 9F

TABLE 9C continued (SEQ. ID. NO. 9, continued)
cttgacggggaaagccggcgaacgtggcgagaaaggaagggaagaaagcgaaaggagcgggcgctagggcgctggcaagtgtagc
ggtcacgctgcgcgtaaccaccacacccgccgcgcttaatgcgccgctacagggcgcgtcaggtggcacttttcggggaaatgtgcgcg
gaaccccctatttgtttattttctaaatacattcaaatatgtatccgctcatgagacaataaccctgataaatgcttcaataatattgaaaaaggaag
agtcctgaggcggaaagaaccagctgtggaatgtgtgtcagttagggtgtggaaagtccccaggctccccagcaggcagaagtatgcaaa
gcatgcatctcaattagtcagcaaccaggtgtggaaagtccccaggctccccagcaggcagaagtatgcaaagcatgcatctcaattagtc
agcaaccatagtcccgcccctaactccgcccatcccgccccctaactccgcccagttccgcccattctccgccccatggctgactaattttttt
atttatgcagaggccgaggccgcctcggcctctgagctattccagaagtagtgaggaggcttttttggaggcctaggcttttgcaaagatcga
tcaagagacaggatgaggatcgtttcgcatgattgaacaagatggattgcacgcaggttctccggccgcttgggtggagaggctattcggct
atgactgggcacaacagacaatcggctgctctgatgccgccgtgttccggctgtcagcgcaggggcgcccggttcttttgtcaagaccga
cctgtccggtgccctgaatgaactgcaagacgaggcagcgcggctatcgtggctggccacgacgggcgttccttgcgcagctgtgctcga
cgttgtcactgaagcgggaagggactggctgctattgggcgaagtgccggggcaggatctcctgtcatctcaccttgctcctgccgagaaa
gtatccatcatggctgatgcaatgcggcggctgcatacgcttgatccggctacctgcccattcgaccaccaagcgaaacatcgcatcgagc
gagcacgtactcggatggaagccggtcttgtcgatcaggatgatctggacgaagagcatcaggggctcgcgccagccgaactgttcgcca
ggctcaaggcgagcatgcccgacggcgaggatctcgtcgtgacccatggcgatgcctgcttgccgaatatcatggtggaaaatggccgct
tttctggattcatcgactgtggccggctgggtgtggcggaccgctatcaggacatagcgttggctacccgtgatattgctgaagagcttggcg
gcgaatgggctgaccgcttcctcgtgctttacggtatcgccgctcccgattcgcagcgcatcgccttctatcgccttcttgacgagttcttctga
gcgggactctggggttcgaaatgaccgaccaagcgacgcccaacctgccatcacgagatttcgattccaccgccgccttctatgaaaggtt
gggcttcggaatcgttttccgggacgccggctggatgatcctccagcgcggggatctcatgctggagttcttcgcccaccctaggggggagg
ctaactgaaacacggaaggagacaataccggaaggaacccgcgctatgacggcaataaaaagacagaataaaacgcacggtgttgggt
cgtttgttcataaacgcggggttcggtcccagggctggcactctgtcgatacccaccgagacccattggggccaatacgcccgcgtttct
tccttttccccaccccaccccccaagttcgggtgaaggcccagggctcgcagccaacgtcggggcggcaggccctgccatagcctcagg
ttactcatatatactttagattgatttaaaacttcattttttaatttaaaaggatctaggtgaagatcctttttgataatctcatgaccaaaatcccttaac
gtgagttttcgttccactgagcgtcagaccccgtagaaaagatcaaaggatcttcttgagatcctttttttctgcgcgtaatctgctgcttgcaaa
caaaaaaaccaccgctaccagcggtggtttgtttgccggatcaagagctaccaactcttttccgaaggtaactggcttcagcagagcgcag
ataccaaatactgtccttctagtgtagccgtagttaggccaccacttcaagaactctgtagcaccgcctacatacctcgctctgctaatcctgtta
ccagtggctgctgccagtggcgataagtcgtgtcttaccgggttggactcaagacgatagttaccggataaggcgcagcggtcgggctga
acggggggttcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttccagggggaa
acgcctggtatctttatagtcctgtcgggtttcgccacctctgacttgagcgtcgatttttgtgatgctcgtcagggggcggagcctatggaaa
aacgccagcaacgcggccttttacggttcctggccttttgctggccttttgctcacatgttctttcctgcgttatcccctgattctgtggataacc
gtattaccgccatgcat

FIGURE 9G

TABLE 9D

GFP-normalized cytoplasmic FAP expression vector pCYdL9.5eGFP
The open reading frame is displayed between line breaks in bold text and includes the following annotated features. The nucleotide sequence encoding dL9.5 is capitalized. The nucleotide sequence of eGFP is underlined.

(SEQ. ID. NO. 10)
tagttattaatagtaatcaattacggggtcattagttcatagcccatatatggagttccgcgttacataacttacggtaaatggcccgcctggctg
accgcccaacgacccccgcccattgacgtcaataatgacgtatgttcccatagtaacgccaatagggactttccattgacgtcaatgggtgg
agtatttacggtaaactgcccacttggcagtacatcaagtgtatcatatgccaagtacgccccctattgacgtcaatgacggtaaatggcccg
cctggcattatgcccagtacatgaccttatgggactttcctacttggcagtacatctacgtattagtcatcgctattaccatggtgatgcggttttg
gcagtacatcaatgggcgtggatagcggtttgactcacggggatttccaagtctccacccccattgacgtcaatgggagtttgttttggcacca
aaatcaacgggactttccaaaatgtcgtaacaactccgccccattgacgcaaatgggcggtaggcgtgtacggtgggaggtctatataagc
agagctggtttagtgaaccgtcagatccgctagcgctaccggtcgccacc
**atggccTCTTACGAATTAACACAACCTCCATCTGTTTCTGTTTCTCCAGGTCAAACT
GCTAGAATTACTTGTTCTGGTGATGCTTTGCCAAAACAATACACTTACTGGTAT
CAACAAAAAGCTGGTCAAGCTCCAGTTTTGGTTATTTATAAAGATACTGAAAGA
CCATCTGGTATTCCAGAAAGATTCTCAGGTACTTCTTCTGGTACTACTGCTACT
TTGACTATTTCTGGTGTTCAAGCTGAAGATGAAGCTGATTATTATTGTCAATCT
GCTGATTCTTCTGGTTCTCATGTATTTTTCGGTGGTGGTACTAAAGTTACTGTT
TTGTCTGGTGGAGGAGGCCCAGGTGGCGGTTCAGGTGGAGGTTCTGGCGGAG
GTTCTGGTGGAGGTTCCTATGAGTTGACTCAGCCACCCTCGGTGTCAGTGTCC
CCAGGACAGACGGCCAGGATCACCTGCTCTGGAGATGCATTGCCAAAGCAATA
TACTTATTGGTACCAGCAGAAGGCAGGCCAGGCCCCTGTCTTGGTGATATATA
AAGACACTGAGAGGCCCTCAGGGATCCCTGAGCGATTCTCTGGTACCAGTTCA
GGGACAACAGCCACATTGACCATCAGTGGAGTCCAGGCAGAAGACGAGGCTGA
CTATTACTGTCAATCAGCAGACAGCAGTGGTTCCCACGTTTTCTTCGGCGGAGG
GACCAAGGTGACCGTACTATCC**ggagggcgcgcctctggtggcggagcttctggaggtggttctggcggctct
<u>ggtatggtgagcaaggggaggagctgttcaccggggtggtgcccatcctggtcgagctggacggcgacgtaaacggccacaag</u>
<u>ttcagcgtgtccggcgagggcgagggcgatgccacctacggcaagctgaccctgaagttcatctgcaccaccggcaagctgcccg</u>
<u>tgccctggcccacctcgtgaccaccctgacctacggcgtgcagtgcttcagccgctaccccgaccacatgaagcagcacgacttct</u>
<u>tcaagtccgccatgcccgaaggctacgtccaggagcgcaccatcttcttcaaggacgacggcaactacaagacccgcgccgaggt</u>
<u>gaagttcgagggcgacaccctggtgaaccgcatcgagctgaagggcatcgacttcaaggaggacggcaacatcctggggcacaa</u>
<u>gctggagtacaactacaacagccacaacgtctatatcatggccgacaagcagaagaacggcatcaaggtgaacttcaagatccg</u>
<u>ccacaacatcgaggacggcagcgtgcagctcgccgaccactaccagcagaacacccccatcggcgacggccccgtgctgctgcc</u>
<u>cgacaaccactacctgagcacccagtccgccctgagcaaagaccccaacgagaagcgcgatcacatggtcctgctggagttcgtg</u>
<u>accgccgccgggatcactctcggcatggacgagctgtacaagtaa</u>
cccgggatccaccggatctagataactgatcataatcagccataccacatttgtagaggttttacttgctttaaaaaacctcccacacctccccc
tgaacctgaaacataaaatgaatgcaattgttgttgttaacttgtttattgcagcttataatggttacaaataaagcaatagcatcacaaatttcaca
aataaagcatttttttcactgcattctagttgtggtttgtccaaactcatcaatgtatcttaacgcgtaaattgtaagcgttaatattttgttaaaattcg
cgttaaattttgttaaatcagctcatttttaaccaataggccgaaatcggcaaaatcccttataaatcaaaagaatagaccgagatagggttga
gtgttgttccagtttggaacaagagtccactattaaagaacgtggactccaacgtcaaagggcgaaaaaccgtctatcagggcgatggccc
actacgtgaaccatcaccctaatcaagttttttggggtcgaggtgccgtaaagcactaaatcggaaccctaaagggagccccccgatttagag

FIGURE 9H

TABLE 9D continued (SEQ. ID. NO. 10, continued)
cttgacggggaaagccggcgaacgtggcgagaaaggaagggaagaaagcgaaaggagcgggcgctagggcgctggcaagtgtagc
ggtcacgctgcgcgtaaccaccacacccgccgcgcgcttaatgcgccgctacagggcgcgtcaggtggcactttcgggggaaatgtgcgcg
gaaccccctatttgtttattttctaaatacattcaaatatgtatccgctcatgagacaataaccctgataaatgcttcaataatattgaaaaaggaag
agtcctgaggcggaaagaaccagctgtggaatgtgtgtcagttagggtgtggaaagtccccaggctccccagcaggcagaagtatgcaaa
gcatgcatctcaattagtcagcaaccaggtgtggaaagtccccaggctccccagcaggcagaagtatgcaaagcatgcatctcaattagtc
agcaaccatagtcccgcccctaactccgcccatcccgcccctaactccgcccagttccgcccattctccgccccatggctgactaatttttttt
atttatgcagaggccgaggccgcctcggcctctgagctattccagaagtagtgaggaggcttttttggaggcctaggcttttgcaaagatcga
tcaagagacaggatgaggatcgtttcgcatgattgaacaagatggattgcacgcaggttctccggccgcttgggtggagaggctattcggct
atgactgggcacaacagacaatcggctgctctgatgccgccgtgttccggctgtcagcgcaggggcgcccggttcttttttgtcaagaccga
cctgtccggtgccctgaatgaactgcaagacgaggcagcgcggctatcgtggctggccacgacgggcgttccttgcgcagctgtgctcga
cgttgtcactgaagcgggaagggactggctgctattgggcgaagtgccggggcaggatctcctgtcatctcaccttgctcctgccgagaaa
gtatccatcatggctgatgcaatgcggcggctgcatacgcttgatccggctacctgcccattcgaccaccaagcgaaacatcgcatcgagc
gagcacgtactcggatggaagccggtcttgtcgatcaggatgatctggacgaagagcatcaggggctcgcgccagccgaactgttcgcca
ggctcaaggcgagcatgcccgacggcgaggatctcgtcgtgacccatggcgatgcctgcttgccgaatatcatggtggaaaatggccgct
tttctggattcatcgactgtggccggctgggtgtggcggaccgctatcaggacatagcgttggctacccgtgatattgctgaagagcttggcg
gcgaatgggctgaccgcttcctcgtgctttacggtatcgccgctcccgattcgcagcgcatcgccttctatcgccttcttgacgagttcttctga
gcgggactctggggttcgaaatgaccgaccaagcgacgcccaacctgccatcacgagatttcgattccaccgccgccttctatgaaaggtt
gggcttcggaatcgttttccgggacgccggctggatgatcctccagcgcggggatctcatgctggagttcttcgcccacccctaggggggagg
ctaactgaaacacggaaggagacaataccggaaggaacccgcgctatgacggcaataaaaagacagaataaaacgcacggtgttgggt
cgtttgttcataaacgcggggttcggtcccagggctggcactctgtcgataccccaccgagacccattggggccaatacgcccgcgtttct
tccttttcccaccccacccccccaagttcgggtgaaggcccagggctcgcagccaacgtcggggcggcaggccctgccatagcctcagg
ttactcatatatactttagattgatttaaaacttcattttttaatttaaaaggatctaggtgaagatcctttttgataatctcatgaccaaaatcccttaac
gtgagttttcgttccactgagcgtcagaccccgtagaaaagatcaaaggatcttcttgagatccttttttctgcgcgtaatctgctgcttgcaaa
caaaaaaaccaccgctaccagcggtggtttgtttgccggatcaagagctaccaactctttttccgaaggtaactggcttcagcagagcgcag
ataccaaatactgtccttctagtgtagccgtagttaggccaccacttcaagaactctgtagcaccgcctacatacctcgctctgctaatcctgtta
ccagtggctgctgccagtggcgataagtcgtgtcttaccgggttggactcaagacgatagttaccggataaggcgcagcggtcgggctga
acgggggttcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttccagggggaa
acgcctggtatctttatagtcctgtcgggtttcgccacctctgacttgagcgtcgatttttgtgatgctcgtcaggggggcggagcctatggaaa
aacgccagcaacgcggcctttttacggttcctggccttttgctggccttttgctcacatgttctttcctgcgttatcccctgattctgtggataacc
gtattaccgccatgcat

FIGURE 9I

TABLE 9E

Mitochondrial expression vector pMTdL9.5eGFP
The open reading frame is displayed between line breaks in bold text and includes the following annotated features. The mitochondrial localization signal is italicized. The nucleotide sequence encoding dL9.5 is capitalized. The nucleotide sequence of eGFP is underlined.

(SEQ. ID. NO. 11)
tagttattaatagtaatcaattacggggtcattagttcatagcccatatatggagttccgcgttacataacttacggtaaatggcccgcctggctg
accgcccaacgacccccgcccattgacgtcaataatgacgtatgttcccatagtaacgccaatagggactttccattgacgtcaatgggtgg
agtatttacggtaaactgcccacttggcagtacatcaagtgtatcatatgccaagtacgccccctattgacgtcaatgacggtaaatggcccg
cctggcattatgcccagtacatgaccttatgggactttcctacttggcagtacatctacgtattagtcatcgctattaccatggtgatgcggttttg
gcagtacatcaatgggcgtggatagcggtttgactcacggggatttccaagtctccacccattgacgtcaatgggagtttgttttggcacca
aaatcaacgggactttccaaaatgtcgtaacaactccgccccattgacgcaaatgggcggtaggcgtgtacggtgggaggtctatataagc
agagctggtttagtgaaccgtcagatccgctagcgctaccggtcgccacc
*atgctcgctacaagagttttctcacttgtcggcaaaagagccatttctacctcggtttgtgtaagggctgaagaa*tctaga**AGCTAC
GAACTGACACAACCTCCATCTGTTTCTGTTTCTCCAGGTCAAACTGCTAGAATT
ACTTGTTCTGGTGATGCTTTGCCAAAACAATACACTTACTGGTATCAACAAAAA
GCTGGTCAAGCTCCAGTTTTGGTTATTTATAAAGATACTGAAAGACCATCTGGT
ATTCCAGAAAGATTCTCAGGTACTTCTTCTGGTACTACTGCTACTTTGACTATTT
CTGGTGTTCAAGCTGAAGATGAAGCTGATTATTATTGTCAATCTGCTGATTCTT
CTGGTTCTCATGTATTTTTCGGTGGTGGTACTAAAGTTACTGTTTTGTCTGGTG
GAGGAGGCCCAGGTGGCGGTTCAGGTGGAGGTTCTGGCGGAGGTTCTGGTGG
AGGTTCCTATGAGTTGACTCAGCCACCCTCGGTGTCAGTGTCCCCAGGACAGA
CGGCCAGGATCACCTGCTCTGGAGATGCATTGCCAAAGCAATATACTTATTGGT
ACCAGCAGAAGGCAGGCCAGGCCCCTGTCTTGGTGATATATAAAGACACTGAG
AGGCCCTCAGGGATCCCTGAGCGATTCTCTGGTACCAGTTCAGGGACAACAGC
CACATTGACCATCAGTGGAGTCCAGGCAGAAGACGAGGCTGACTATTACTGTC
AATCAGCAGACAGCAGTGGTTCCCACGTTTTCTTCGGCGGAGGGACCAAGGTG
ACCGTACTATCC**<u>ggagggcgcgcctctggtggcggagcttctggaggtggttctggcggctctggtatggtgagcaagg
gcgaggagctgttcaccggggtggtgcccatcctggtcgagctggacggcgacgtaaacggccacaagttcagcgtgtccggcga
gggcgagggcgatgccacctacggcaagctgaccctgaagttcatctgcaccaccggcaagctgcccgtgccctggcccaccctc
gtgaccaccctgacctacggcgtgcagtgcttcagccgctaccccgaccacatgaagcagcacgacttcttcaagtccgccatgcc
cgaaggctacgtccaggagcgcaccatcttcttcaaggacgacggcaactacaagacccgcgccgaggtgaagttcgagggcga
cacctgtgaaccgcatcgagctgaagggcatcgacttcaaggaggacggcaacatcctggggcacaagctggagtacaacta
caacagccacaacgtctatatcatggccgacaagcagaagaacggcatcaaggtgaacttcaagatccgccacaacatcgagga
cggcagcgtgcagctcgccgaccactaccagcagaacacccccatcggcgacggccccgtgctgctgcccgacaaccactacctg
agcacccagtccgccctgagcaaagaccccaacgagaagcgcgatcacatggtcctgctggagttcgtgaccgccgccgggatca
ctctcggcatggacgagctgtacaagtaa</u>
cccgggatccaccggatctagataactgatcataatcagccataccacatttgtagaggttttacttgctttaaaaaacctcccacacctccccc
tgaacctgaaacataaaatgaatgcaattgttgttgttaacttgtttattgcagcttataatggttacaaataaagcaatagcatcacaaatttcaca
aataaagcatttttttcactgcattctagttgtggtttgtccaaactcatcaatgtatcttaacgcgtaaattgtaagcgttaatattttgttaaaattcg
cgttaaattttgttaaatcagctcattttttaaccaataggccgaaatcggcaaaatcccttataaatcaaaagaatagaccgagatagggttga
gtgttgttccagtttggaacaagagtccactattaaagaacgtggactccaacgtcaaagggcgaaaaaccgtctatcagggcgatggccc

FIGURE 9J

TABLE 9E continued (SEQ. ID. NO. 11, continued)
actacgtgaaccatcaccctaatcaagttttttgggtcgaggtgccgtaaagcactaaatcggaaccctaaagggagcccccgatttagag
cttgacggggaaagccggcgaacgtggcgagaaaggaagggaagaaagcgaaaggagcgggcgctagggcgctggcaagtgtagc
ggtcacgctgcgcgtaaccaccacacccgccgcgcttaatgcgccgctacagggcgcgtcaggtggcacttttcggggaaatgtgcgcg
gaacccctatttgtttattttctaaatacattcaaatatgtatccgctcatgagacaataaccctgataaatgcttcaataatattgaaaaaggaag
agtcctgaggcggaaagaaccagctgtggaatgtgtgtcagttagggtgtggaaagtccccaggctccccagcaggcagaagtatgcaaa
gcatgcatctcaattagtcagcaaccaggtgtggaaagtccccaggctccccagcaggcagaagtatgcaaagcatgcatctcaattagtc
agcaaccatagtcccgcccctaactccgcccatcccgcccctaactccgcccagttccgcccattctccgccccatggctgactaatttttttt
atttatgcagaggccgaggccgcctcggcctctgagctattccagaagtagtgaggaggcttttttggaggcctaggcttttgcaaagatcga
tcaagagacaggatgaggatcgtttcgcatgattgaacaagatggattgcacgcaggttctccggccgcttgggtggagaggctattcggct
atgactgggcacaacagacaatcggctgctctgatgccgccgtgttccggctgtcagcgcaggggcgcccggttcttttgtcaagaccga
cctgtccggtgccctgaatgaactgcaagacgaggcagcgcggctatcgtggctggccacgacgggcgttccttgcgcagctgtgctcga
cgttgtcactgaagcgggaagggactggctgctattgggcgaagtgccggggcaggatctcctgtcatctcaccttgctcctgccgagaaa
gtatccatcatggctgatgcaatgcggcggctgcatacgcttgatccggctacctgcccattcgaccaccaagcgaaacatcgcatcgagc
gagcacgtactcggatggaagccggtcttgtcgatcaggatgatctggacgaagagcatcaggggctcgcgccagccgaactgttcgcca
ggctcaaggcgagcatgcccgacggcgaggatctcgtcgtgacccatggcgatgcctgcttgccgaatatcatggtggaaaatggccgct
tttctggattcatcgactgtggccggctgggtgtggcggaccgctatcaggacatagcgttggctacccgtgatattgctgaagagcttggcg
gcgaatgggctgaccgcttcctcgtgctttacggtatcgccgctcccgattcgcagcgcatcgccttctatcgccttcttgacgagttcttctga
gcgggactctggggttcgaaatgaccgaccaagcgacgcccaacctgccatcacgagatttcgattccaccgccgccttctatgaaaggtt
gggcttcggaatcgttttccgggacgccggctggatgatcctccagcgcggggatctcatgctggagttcttcgcccaccctaggggggagg
ctaactgaaacacggaaggagacaataccggaaggaacccgcgctatgacggcaataaaaagacagaataaaacgcacggtgttgggt
cgtttgttcataaacgcggggttcggtcccagggctggcactctgtcgataccccaccgagacccattggggccaatacgcccgcgtttct
tccttttcccccaccccacccccccaagttcgggtgaaggcccagggctcgcagccaacgtcggggcggcaggccctgccatagcctcagg
ttactcatatatactttagattgatttaaaacttcatttttaatttaaaaggatctaggtgaagatccttttgataatctcatgaccaaaatcccttaac
gtgagttttcgttccactgagcgtcagaccccgtagaaaagatcaaaggatcttcttgagatcctttttttctgcgcgtaatctgctgcttgcaaa
caaaaaaaccaccgctaccagcggtggtttgtttgccggatcaagagctaccaactctttttccgaaggtaactggcttcagcagagcgcag
ataccaaatactgtccttctagtgtagccgtagttaggccaccacttcaagaactctgtagcaccgcctacatacctcgctctgctaatcctgtta
ccagtggctgctgccagtggcgataagtcgtgtcttaccgggttggactcaagacgatagttaccggataaggcgcagcggtcgggctga
acggggggttcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgaggggagcttccagggggaa
acgcctggtatctttatagtcctgtcgggtttcgccacctctgacttgagcgtcgatttttgtgatgctcgtcaggggggcggagcctatggaaa
aacgccagcaacgcggcctttttacggttcctggccttttgctggccttttgctcacatgttctttcctgcgttatcccctgattctgtggataacc
gtattaccgccatgcat

FIGURE 9K

TABLE 9F
Bi-cistronic lentiviral vector for transduction of mammalian cells with dL9.2 and eGFP
The bi-cistronic expression cassette encompassing both FAP and eGFP open reading frames is displayed between line breaks in bold text and includes the following annotated features. The Igκ signal is italicized. The nucleotide sequence encoding dL9.2 is capitalized. The transmembrane domain of CD80, which tethers the FAP to the extracellular face of the plasma membrane, is underlined. The nucleotide sequence of eGFP is double underlined.

(SEQ. ID. NO. 12)
gtcgacggatcgggagatctcccgatcccctatggtgcactctcagtacaatctgctctgatgccgcatagttaagccagtatctgctccctgc
ttgtgtgttggaggtcgctgagtagtgcgcgagcaaaatttaagctacaacaaggcaaggcttgaccgacaattgcatgaagaatctgcttag
ggttaggcgttttgcgctgcttcgcgatgtacgggccagatatacgcgttgacattgattattgactagttattaatagtaatcaattacggggtc
attagttcatagcccatatatggagttccgcgttacataacttacggtaaatggcccgcctggctgaccgcccaacgaccccgcccattgac
gtcaataatgacgtatgttcccatagtaacgccaatagggactttccattgacgtcaatgggtggagtatttacggtaaactgcccacttggca
gtacatcaagtgtatcatatgccaagtacgccccctattgacgtcaatgacggtaaatggcccgcctggcattatgcccagtacatgaccttat
gggactttcctacttggcagtacatctacgtattagtcatcgctattaccatggtgatgcggttttggcagtacatcaatgggcgtggatagcgg
tttgactcacggggatttccaagtctccacccattgacgtcaatgggagtttgttttggcaccaaaatcaacgggactttccaaaatgtcgtaa
caactccgccccattgacgcaaatgggcggtaggcgtgtacggtgggaggtctatataagcagcgcgttttgcctgtactgggtctctctggt
tagaccagatctgagcctgggagctctctggctaactagggaacccactgcttaagcctcaataaagcttgccttgagtgcttcaagtagtgt
gtgcccgtctgttgtgtgactctggtaactagagatccctcagacccttttagtcagtgtggaaaatctctagcagtggcgcccgaacaggga
cttgaaagcgaaagggaaaccagaggagctctctcgacgcaggactcggcttgctgaagcgcgcacggcaagaggcgaggggcggc
gactggtgagtacgccaaaaattttgactagcggaggctagaaggagagagatgggtgcgagagcgtcagtattaagcgggggagaatt
agatcgcgatgggaaaaaattcggttaaggccagggggaaagaaaaaatataaattaaaacatatagtatgggcaagcagggagctagaa
cgattcgcagttaatcctggcctgttagaaacatcagaaggctgtagacaaatactgggacagctacaaccatcccttcagacaggatcaga
agaacttagatcattatataatacagtagcaaccctctattgtgtgcatcaaaggatagagataaaagacaccaaggaagctttagacaagat
agaggaagagcaaaacaaaagtaagaccaccgcacagcaagcggccgctgatcttcagacctggaggaggagatatgagggacaattg
gagaagtgaattatataaatataaagtagtaaaaattgaaccattaggagtagcacccaccaaggcaaagagaagagtggtgcagagaga
aaaaagagcagtgggaataggagctttgttccttgggttcttgggagcagcaggaagcactatgggcgcagcgtcaatgacgctgacggt
acaggccagacaattattgtctggtatagtgcagcagcagaacaatttgctgagggctattgaggcgcaacagcatctgttgcaactcacagt
ctggggcatcaagcagctccaggcaagaatcctggctgtggaaagatacctaaaggatcaacagctcctggggatttggggttgctctgga
aaactcatttgcaccactgctgtgccttggaatgctagttggagtaataaatctctggaacagatttggaatcacacgacctggatggagtggg
acagagaaattaacaattacacaagcttaatacactccttaattgaagaatcgcaaaaccagcaagaaaagaatgaacaagaattattggaat
tagataaatgggcaagtttgtggaattggtttaacataacaaattggctgtggtatataaaattattcataatgatagtaggaggcttggtaggttt
aagaatagttttgctgtactttctatagtgaatagagttaggcagggatattcaccattatcgtttcagacccacctcccaacccc gaggggac
ccgacaggcccgaaggaatagaagaagaaggtggagagagagacagagacagatccattcgattagtgaacggatcggcactgcgtgc
gccaattctgcagacaaatggcagtattcatccacaattttaaaagaaaaggggggattggggggtacagtgcaggggaaagaatagtaga
cataatagcaacagacatacaaactaaagaattacaaaaacaaattacaaaaattcaaaattttcgggtttattacagggacagcagagatcc
agtttggttaattaatagttattaatagtaatcaattacggggtcattagttcatagcccatatatggagttccgcgttacataacttacggtaaatg
gcccgcctggctgaccgcccaacgaccccgcccattgacgtcaataatgacgtatgttcccatagtaacgccaatagggactttccattga
cgtcaatgggtggagtatttacggtaaactgcccacttggcagtacatcaagtgtatcatatgccaagtacgccccctattgacgtcaatgacg
gtaaatggcccgcctggcattatgcccagtacatgaccttatgggactttcctacttggcagtacatctacgtattagtcatcgctattaccatgg
tgatgcggttttggcagtacatcaatgggcgtggatagcggtttgactcacggggatttccaagtctccacccattgacgtcaatgggagttt
gttttggcaccaaaatcaacgggactttccaaaatgtcgtaacaactccgccccattgacgcaaatgggcggtaggcgtgtacggtgggag
gtctatataagcagagctggtttagtgaaccgtcagatccgctagcgctaccggtcgccacc

FIGURE 9L

TABLE 9F continued (SEQ. ID. NO. 12, continued)

*atggagacagacacactcctgctatgggtactgctgctctgggttccaggttccactggtgac*tatccatatgatgttccagattatgctt
ctagcTCTTACGAATTAACACAACCTCCATCTGTTTCTGTTTCTCCAGGTCAAACT
GCTAGAATTACTTGTTCTGGTGATGCTTTGCCAAAACAATACACTTACTGGTAT
CAACAAAAAGCTGGTCAAGCTCCAGTTTTGGTTATTTATAAAGATACTGAAAGA
CCATCTGGTATTCCAGAAAGATTCTCAGGTACTTCTTCTGGTACTACTGCTACT
TTGACTATTTCTGGTGTTCAAGCTGAAGATGAAGCTGATTATTATTGTCAATCT
GCTGATTCTTCTGGTTCTTATGTATTTTTCGGTGGTGGTACTAAAGTTACTGTTT
TGTCTGGTGGAGGAGGCCCAGGTGGCGGTTCAGGTGGAGGTTCTGGCGGAGG
TTCTGGTGGAGGTTCCTATGAGTTGACTCAGCCACCCTCGGTGTCAGTGTCCCC
AGGACAGACGGCCAGGATCACCTGCTCTGGAGATGCATTGCCAAAGCAATATA
CTTATTGGTACCAGCAGAAGGCAGGCCAGGCCCCTGTCTTGGTGATATATAAA
GACACTGAGAGGCCCTCAGGGATCCCTGAGCGATTCTCTGGTACCAGTTCAGG
GACAACAGTCACATTGACCATCAGTGGAGTCCAGGCAGAAGACGAGGCTGACT
ATTACTGTCAATCAGCAGACAGCAGTGGTTCCTATGTTTTCTTCGGCGGAGGGA
CCAAGGTGACCGTACTATCCggaggcggtgggaagaagttccccccagaagaccctcctgatagcaagaaca
cacttgtgctctttggggcaggattcggcgcagtaataacagtcgtcgtcatcgttgtcatcatcaaatgcttctgtaagcacagaag
ctgtttcagaagaaatgaggcaagcagagaaacaaacaacagccttaccttcgggcctgaagaagcattagctgaacagaccgt
cttcctttgtacatagtaatgaacggatccgtaattccgccctctccctccccccccctaacgttactggccgaagccgcttggaat
aaggccggtgtgcgtttgtctatatgttatttttccaccatattgccgtcttttggcaatgtgagggcccggaaacctggccctgtcttctt
gacgagcattcctaggggtctttcccctctcgccaaaggaatgcaaggtctgttgaatgtcgtgaaggaagcagttcctctggaagc
ttcttgaagacaaacaacgtctgtagcgacccttttgcaggcagcggaaccccccacctggcgacaggtgcctctgcggccaaaag
ccacgtgtataagatacacctgcaaaggcggcacaaccccagtgccacgttgtgagttggatagttgtggaaagagtcaaatggct
ctcctcaagcgtattcaacaaggggctgaaggatgcccagaaggtaccccattgtatgggatctgatctggggcctcggtgcacat
gctttacatgtgtttagtcgaggttaaaaaacgtctaggcccccgaaccacggggacgtggttttcctttgaaaaacacgatgata
agcttgccacaacccacaaggagacggcgcgccatggtgagcaaggcgaggagctgttcaccggggtggtgcccatcctggtc
gagctggacggcgacgtaaacggccacaagttcagcgtgtccggcgagggcgagggcgatgccacctacggcaagctgaccctg
aagttcatctgcaccaccggcaagctgcccgtgccctggcccaccctcgtgaccaccctgacctacggcgtgcagtgcttcagccgc
taccccgaccacatgaagcagcacgacttcttcaagtccgccatgcccgaaggctacgtccaggagcgcaccatcttcttcaagga
cgacggcaactacaagacccgcgccgaggtgaagttcgagggcgacaccctggtgaaccgcatcgagctgaagggcatcgactt
caaggaggacggcaacatcctggggcacaagctggagtacaactacaacagccacaacgtctatatcatggccgacaagcaga
agaacggcatcaaggtgaacttcaagatccgccacaacatcgaggacggcagcgtgcagctcgccgaccactaccagcagaaca
cccccatcggcgacggccccgtgctgctgcccgacaaccactacctgagcacccagtccgccctgagcaaagaccccaacgaga
agcgcgatcacatggtcctgctggagttcgtgaccgccgccgggatcactctcggcatggacgagctgtataagtaa
taggaattcgatatcaagcttatcgataatcaacctctggattacaaaatttgtgaaagattgactggtattcttaactatgttgctccttttacgcta
tgtggatacgctgctttaatgcctttgtatcatgctattgcttcccgtatggctttcattttctcctccttgtataaatcctggttgctgtctctttatgag
gagttgtggcccgttgtcaggcaacgtggcgtggtgtgcactgtgtttgctgacgcaacccccactggttggggcattgccaccacctgtca
gctccttccgggactttcgctttccccctccctattgccacggcggaactcatcgccgcctgccttgcccgctgctggacaggggctcggct
gttgggcactgacaattccgtggtgttgtcggggaaatcatcgtcctttccttggctgctcgcctgtgttgccacctggattctgcgcgggacg
tccttctgctacgtcccttcggccctcaatccagcggaccttccttcccgcggcctgctgccggctctgcggcctcttccgcgtcttcgccttc
gccctcagacgagtcggatctccctttgggccgcctccccgcatcgataccgtcgacctcgagacctagaaaaacatggagcaatcacaa

FIGURE 9M

TABLE 9F continued

(SEQ. ID. NO. 12, continued)
gtagcaatacagcagctaccaatgctgattgtgcctggctagaagcacaagaggaggaggaggtgggttttccagtcacacctcaggtacc
tttaagaccaatgacttacaaggcagctgtagatcttagccactttttaaaagaaaaggggggactggaagggctaattcactcccaacgaa
gacaagatatccttgatctgtggatctaccacacacaaggctacttccctgattggcagaactacacaccagggccagggatcagatatcca
ctgacctttggatggtgctacaagctagtaccagttgagcaagagaaggtagaagaagccaatgaaggagagaacacccgcttgttacacc
ctgtgagcctgcatgggatggatgacccggagagagaagtattagagtggaggtttgacagccgcctagcatttcatcacatggcccgaga
gctgcatccggactgtactgggtctctctggttagaccagatctgagcctgggagctctctggctaactagggaacccactgcttaagcctca
ataaagcttgccttgagtgcttcaagtagtgtgtgcccgtctgttgtgtgactctggtaactagagatccctcagacccttttagtcagtgtggaa
aatctctagcagggcccgtttaaacccgctgatcagcctcgactgtgccttctagttgccagccatctgttgtttgccccctccccgtgccttcc
ttgaccctggaaggtgccactcccactgtcctttcctaataaaatgaggaaattgcatcgcattgtctgagtaggtgtcattctattctggggggt
ggggtggggcaggacagcaagggggaggattgggaagacaatagcaggcatgctggggatgcggtgggctctatggcttctgaggcg
gaaagaaccagctggggctctagggggtatccccacgcgccctgtagcggcgcattaagcgcggcgggtgtggtggttacgcgcagcgt
gaccgctacacttgccagcgccctagcgcccgctcctttcgctttcttcccttccttctcgccacgttcgccggctttccccgtcaagctctaa
atcgggggctcccttaggggttccgatttagtgcttacggcacctcgaccccaaaaaacttgattagggtgatggttcacgtagtgggccatc
gccctgatagacggttttcgcccttgacgttggagtccacgttctttaatagtggactcttgttccaaactggaacaacactcaaccctatctc
ggtctattcttttgatttataagggattttgccgatttcggcctattggttaaaaaatgagctgatttaacaaaaatttaacgcgaattaattctgtgg
aatgtgtgtcagttagggtgtggaaagtccccaggctccccagcaggcagaagtatgcaaagcatgcatctcaattagtcagcaaccaggt
gtggaaagtccccaggctccccagcaggcagaagtatgcaaagcatgcatctcaattagtcagcaaccatagtcccgcccctaactccgcc
catcccgccctaactccgcccagttccgcccattctccgccccatggctgactaatttttttatttatgcagaggccgaggccgcctctgcct
ctgagctattccagaagtagtgaggaggcttttttggaggcctaggcttttgcaaaaagctcccgggagcttgtatatccattttcggatctgat
cagcacgtgttgacaattaatcatcggcatagtatatcggcatagtataatacgacaaggtgaggaactaaaccatggccaagttgaccagt
gccgttccggtgctcaccgcgcgcgacgtcgccggagcggtcgagttctggaccgaccggctcgggttctcccgggacttcgtggagga
cgacttcgccggtgtggtccgggacgacgtgaccctgttcatcagcgcggtccaggaccaggtggtgccggacaacacccctggcctggg
tgtgggtgcgcggcctggacgagctgtacgccgagtggtcggaggtcgtgtccacgaacttccgggacgcctccgggccggccatgacc
gagatcggcgagcagccgtgggggcgggagttcgccctgcgcgacccggccggcaactgcgtgcacttcgtggccgaggagcagga
ctgacacgtgctacgagatttcgattccaccgccgccttctatgaaaggttgggcttcggaatcgttttccgggacgccggctggatgatcct
ccagcgcggggatctcatgctggagttcttcgcccacccccaacttgtttattgcagcttataatggttacaaataaagcaatagcatcacaaatt
tcacaaataaagcatttttttcactgcattctagttgtggtttgtccaaactcatcaatgtatcttatcatgtctgtataccgtcgacctctagctaga
gcttggcgtaatcatggtcatagctgtttcctgtgtgaaattgttatccgctcacaattccacacaacatacgagccggaagcataaagtgtaaa
gcctggggtgcctaatgagtgagctaactcacattaattgcgttgcgctcactgcccgctttccagtcgggaaacctgtcgtgccagctgcatt
aatgaatcggccaacgcgcggggagaggcggtttgcgtattgggcgctcttccgcttcctcgctcactgactcgctgcgctcggtcgttcgg
ctgcggcgagcggtatcagctcactcaaaggcggtaatacggttatccacagaatcaggggataacgcaggaaagaacatgtgagcaaa
aggccagcaaaaggccaggaaccgtaaaaaggccgcgttgctggcgtttttccataggctccgcccccctgacgagcatcacaaaaatcg
acgctcaagtcagaggtggcgaaacccgacaggactataaagataccaggcgtttccccctggaagctccctcgtgcgctctcctgttccg
accctgccgcttaccggatacctgtccgcctttctcccttcgggaagcgtggcgctttctcatagctcacgctgtaggtatctcagttcggtgta
ggtcgttcgctccaagctgggctgtgtgcacgaaccccccgttcagcccgaccgctgcgccttatccggtaactatcgtcttgagtccaacc
cggtaagacacgacttatcgccactggcagcagccactggtaacaggattagcagagcgaggtatgtaggcggtgctacagagttcttgaa
gtggtggcctaactacggctacactagaagaacagtatttggtatctgcgctctgctgaagccagttaccttcggaaaaagagttggtagctct
tgatccggcaaacaaaccaccgctggtagcggtggtttttttgtttgcaagcagcagattacgcgcagaaaaaaaggatctcaagaagatcc
tttgatcttttctacggggtctgacgctcagtggaacgaaaactcacgttaagggattttggtcatgagattatcaaaaaggatcttcacctagat
ccttttaaattaaaaatgaagttttaaatcaatctaaagtatatatgagtaaacttggtctgacagttaccaatgcttaatcagtgaggcacctatct

FIGURE 9N

TABLE 9F continued (SEQ. ID. NO. 12, continued)

cagcgatctgtctatttcgttcatccatagttgcctgactccccgtcgtgtagataactacgatacgggagggcttaccatctggccccagtgct
gcaatgataccgcgagacccacgctcaccggctccagatttatcagcaataaaccagccagccggaagggccgagcgcagaagtggtc
ctgcaactttatccgcctccatccagtctattaattgttgccgggaagctagagtaagtagttcgccagttaatagtttgcgcaacgttgttgcca
ttgctacaggcatcgtggtgtcacgctcgtcgtttggtatggcttcattcagctccggttcccaacgatcaaggcgagttacatgatcccccat
gttgtgcaaaaaagcggttagctccttcggtcctccgatcgttgtcagaagtaagttggccgcagtgttatcactcatggttatggcagcactg
cataattctcttactgtcatgccatccgtaagatgcttttctgtgactggtgagtactcaaccaagtcattctgagaatagtgtatgcggcgaccg
agttgctcttgcccggcgtcaatacgggataataccgcgccacatagcagaactttaaaagtgctcatcattggaaaacgttcttcggggcga
aaactctcaaggatcttaccgctgttgagatccagttcgatgtaacccactcgtgcacccaactgatcttcagcatctttttactttcaccagcgttt
ctgggtgagcaaaaacaggaaggcaaaatgccgcaaaaaagggaataagggcgacacggaaatgttgaatactcatactcttccttttca
atattattgaagcatttatcagggttattgtctcatgagcggatacatatttgaatgtatttagaaaaataaacaaatagggggttccgcgcacattt
ccccgaaaagtgccacctgac

FIGURE 9O

TABLE 9G
Bi-cistronic lentiviral vector for transduction of mammalian cells with dL9.5 and eGFP
The bi-cistronic expression cassette encompassing both FAP and eGFP open reading frames is displayed between line breaks in bold text and includes the following annotated features. The Igκ signal is italicized. The nucleotide sequence encoding dL9.2 is capitalized. The transmembrane domain of CD80, which tethers the FAP to the extracellular face of the plasma membrane, is underlined. The nucleotide sequence of eGFP is double underlined.

(SEQ. ID. NO. 13)
gtcgacggatcgggagatctcccgatcccctatggtgcactctcagtacaatctgctctgatgccgcatagttaagccagtatctgctccctgc
ttgtgtgttggaggtcgctgagtagtgcgcgagcaaaatttaagctacaacaaggcaaggcttgaccgacaattgcatgaagaatctgcttag
ggttaggcgttttgcgctgcttcgcgatgtacgggccagatatacgcgttgacattgattattgactagttattaatagtaatcaattacggggtc
attagttcatagcccatatatggagttccgcgttacataacttacggtaaatggcccgcctggctgaccgcccaacgaccccgcccattgac
gtcaataatgacgtatgttcccatagtaacgccaatagggactttccattgacgtcaatgggtggagtatttacggtaaactgcccacttggca
gtacatcaagtgtatcatatgccaagtacgccccctattgacgtcaatgacggtaaatggcccgcctggcattatgcccagtacatgacctat
gggactttcctacttggcagtacatctacgtattagtcatcgctattaccatggtgatgcggttttggcagtacatcaatgggcgtggatagcgg
tttgactcacggggatttccaagtctccacccattgacgtcaatgggagtttgttttggcaccaaaatcaacgggactttccaaaatgtcgtaa
caactccgccccattgacgcaaatgggcggtaggcgtgtacggtggggaggtctatataagcagcgcgttttgcctgtactgggtctctctggt
tagaccagatctgagcctgggagctctctggctaactagggaacccactgcttaagcctcaataaagcttgccttgagtgcttcaagtagtgt
gtgcccgtctgttgtgtgactctggtaactagagatccctcagacccttttagtcagtgtggaaaatctctagcagtggcgcccgaacaggga
cttgaaagcgaaagggaaaccagaggagctctctcgacgcaggactcggcttgctgaagcgcgcacggcaagaggcgaggggcggc
gactggtgagtacgccaaaaattttgactagcggaggctagaaggagagagatgggtgcgagagcgtcagtattaagcggggagaatt
agatcgcgatgggaaaaaattcggttaaggccagggggaaagaaaaaatataaattaaaacatatagtatgggcaagcagggagctagaa
cgattcgcagttaatcctggcctgttagaaacatcagaaggctgtagacaaatactgggacagctacaaccatccttcagacaggatcaga
agaacttagatcattatataatacagtagcaaccctctattgtgtgcatcaaaggatagagataaaagacaccaaggaagcttagacaagat
agaggaagagcaaaacaaaagtaagaccaccgcacagcaagcggccgctgatcttcagacctggaggaggagatatgagggacaatg
gagaagtgaattatataaatataaagtagtaaaaattgaaccattaggagtagcacccaccaaggcaaagagaagagtggtgcagagaga
aaaaagagcagtgggaataggagctttgttccttgggttcttgggagcagcaggaagcactatgggcgcagcgtcaatgacgctgacggt
acaggccagacaattattgtctggtatagtgcagcagcagaacaatttgctgagggcgtattgaggcgcaacagcatctgttgcaactcacagt
ctggggcatcaagcagctccaggcaagaatcctggctgtggaaagatacctaaaggatcaacagctcctggggatttggggttgctctgga
aaactcatttgcaccactgctgtgccttggaatgctagttggagtaataaatctctggaacagatttggaatcacacgacctggatggagtggg
acagagaaattaacaattacacaagcttaatacactccttaattgaagaatcgcaaaaccagcaagaaaagaatgaacaagaattattggaat
tagataaatgggcaagtttgtggaattggtttaacataacaaattggctgtggtatataaaattattcataatgatagtaggaggcttggtaggttt
aagaatagttttgctgtactttctatagtgaatagagttaggcagggatattcaccattatcgtttcagacccacctcccaacccgagggac
ccgacaggcccgaaggaatagaagaagaaggtggagagagagacagagacagatccattcgattagtgaacggatcggcactgcgtgc
gccaattctgcagacaaatggcagtattcatccacaatttttaaaagaaaaggggggattgggggtacagtgcaggggaaagaatagtaga
cataatagcaacagacatacaaactaaagaattacaaaaacaaattacaaaaattcaaaattttcgggttattacagggacagcagagatcc
agtttggttaattaatagttattaatagtaatcaattacggggtcattagttcatagcccatatatggagttccgcgttacataacttacggtaaatg
gcccgcctggctgaccgcccaacgaccccgcccattgacgtcaataatgacgtatgttcccatagtaacgccaatagggactttccattga
cgtcaatgggtggagtatttacggtaaactgcccacttggcagtacatcaagtgtatcatatgccaagtacgccccctattgacgtcaatgacg
gtaaatggcccgcctggcattatgcccagtacatgaccttatgggactttcctacttggcagtacatctacgtattagtcatcgctattaccatgg
tgatgcggttttggcagtacatcaatgggcgtggatagcggtttgactcacggggatttccaagtctccacccattgacgtcaatgggagttt
gttttggcaccaaaatcaacgggactttccaaaatgtcgtaacaactccgccccattgacgcaaatgggcggtaggcgtgtacggtgggag
gtctatataagcagagctggtttagtgaaccgtcagatccgctagcgctaccggtcgccacc

FIGURE 9P

TABLE 9G continued (SEQ. ID. NO. 13, continued)

*atggagacagacacactcctgctatgggtactgctgctctgggttccaggttccactggtgac*tatccatatgatgttccagattatgctt
ctagcTCTTACGAATTAACACAACCTCCATCTGTTTCTGTTTCTCCAGGTCAAACT
GCTAGAATTACTTGTTCTGGTGATGCTTTGCCAAAACAATACACTTACTGGTAT
CAACAAAAAGCTGGTCAAGCTCCAGTTTTGGTTATTTATAAAGATACTGAAAGA
CCATCTGGTATTCCAGAAAGATTCTCAGGTACTTCTTCTGGTACTACTGCTACT
TTGACTATTTCTGGTGTTCAAGCTGAAGATGAAGCTGATTATTATTGTCAATCT
GCTGATTCTTCTGGTTCTCATGTATTTTTCGGTGGTGGTACTAAAGTTACTGTT
TTGTCTGGTGGAGGAGGCCCAGGTGGCGGTTCAGGTGGAGGTTCTGGCGGAG
GTTCTGGTGGAGGTTCCTATGAGTTGACTCAGCCACCCTCGGTGTCAGTGTCC
CCAGGACAGACGGCCAGGATCACCTGCTCTGGAGATGCATTGCCAAAGCAATA
TACTTATTGGTACCAGCAGAAGGCAGGCCAGGCCCCTGTCTTGGTGATATATA
AAGACACTGAGAGGCCCTCAGGGATCCCTGAGCGATTCTCTGGTACCAGTTCA
GGGACAACAGCCACATTGACCATCAGTGGAGTCCAGGCAGAAGACGAGGCTGA
CTATTACTGTCAATCAGCAGACAGCAGTGGTTCCCACGTTTTCTTCGGCGGAGG
GACCAAGGTGACCGTACTATCCggaggcggtgggaagaagttcccccagaagaccctcctgatagcaaga
acaca<u>cttgtgctctttggggcaggattcggcgcagtaataacagtcgtcgtcatcgttgtcatcatc</u>aaatgcttctgtaagcacag
aagctgtttcagaagaaatgaggcaagcagagaaacaaacaacagccttaccttcgggcctgaagaagcattagctgaacagac
cgtcttcctttgtacatagtaatgaacggatccgtaattccgccctctccctccccccccctaacgttactggccgaagccgcttgg
aataaggccggtgtgcgtttgtctatatgttattttccaccatattgccgtcttttggcaatgtgagggcccggaaacctggccctgtct
tcttgacgagcattcctaggggtctttcccctctcgccaaaggaatgcaaggtctgttgaatgtcgtgaaggaagcagttcctctgga
agcttcttgaagacaaacaacgtctgtagcgaccctttgcaggcagcggaaccccccacctggcgacaggtgcctctgcggccaa
aagccacgtgtataagatacacctgcaaaggcggcacaaccccagtgccacgttgtgagttggatagttgtggaaagagtcaaat
ggctctcctcaagcgtattcaacaaggggctgaaggatgcccagaaggtacccattgtatgggatctgatctggggcctcggtgc
acatgctttacatgtgtttagtcgaggttaaaaaacgtctaggcccccccgaaccacggggacgtggttttcctttgaaaaacacgat
gataagcttgccacaacccacaaggagacggcgcgcc<u>atggtgagcaagggcgaggagctgttcaccggggtggtgcccatcct
ggtcgagctggacggcgacgtaaacggccacaagttcagcgtgtccggcgagggcgagggcgatgccacctacggcaagctgac
cctgaagttcatctgcaccaccggcaagctgcccgtgccctggcccaccctcgtgaccaccctgacctacggcgtgcagtgcttcag
ccgctaccccgaccacatgaagcagcacgacttcttcaagtccgccatgcccgaaggctacgtccaggagcgcaccatcttcttca
aggacgacggcaactacaagacccgcgccgaggtgaagttcgagggcgacaccctggtgaaccgcatcgagctgaagggcatc
gacttcaaggaggacggcaacatcctggggcacaagctggagtacaactacaacagccacaacgtctatatcatggccgacaag
cagaagaacggcatcaaggtgaacttcaagatccgccacaacatcgaggacggcagcgtgcagctcgccgaccactaccagcag
aacacccccatcggcgacggccccgtgctgctgcccgacaaccactacctgagcacccagtccgccctgagcaaagaccccaacg
agaagcgcgatcacatggtcctgctggagttcgtgaccgccgccgggatcactctcggcatggacgagctgtataagtaa</u>
taggaattcgatatcaagcttatcgataatcaacctctggattacaaaatttgtgaaagattgactggtattcttaactatgttgctccttttacgcta
tgtggatacgctgctttaatgcctttgtatcatgctattgcttcccgtatggctttcatttctcctccttgtataaatcctggttgctgtctctttatgag
gagttgtggcccgttgtcaggcaacgtggcgtggtgtgcactgtgtttgctgacgcaacccccactggttggggcattgccaccacctgtca
gctcctttccgggactttcgctttccccctccctattgccacggcggaactcatcgccgcctgccttgcccgctgctggacaggggctcggct
gttgggcactgacaattccgtggtgttgtcggggaaatcatcgtccttcctggctgctcgcctgtgttgccacctggattctgcgcgggacg
tccttctgctacgtcccttcggccctcaatccagcggaccttcctcccgcggcctgctgccggctctgcggcctcttccgcgtcttcgccttc
gccctcagacgagtcggatctcccttgggccgcctccccgcatcgataccgtcgacctcgagacctagaaaaacatggagcaatcacaa

FIGURE 9Q

TABLE 9G continued (SEQ. ID. NO. 13, continued)

gtagcaatacagcagctaccaatgctgattgtgcctggctagaagcacaagaggaggaggaggtgggttttccagtcacacctcaggtacc
tttaagaccaatgacttacaaggcagctgtagatcttagccactttttaaaagaaaaggggggactggaagggctaattcactcccaacgaa
gacaagatatccttgatctgtggatctaccacacacaaggctacttccctgattggcagaactacacaccagggccagggatcagatatcca
ctgacctttggatggtgctacaagctagtaccagttgagcaagagaaggtagaagaagccaatgaaggagagaacacccgcttgttacacc
ctgtgagcctgcatgggatggatgacccggagagagaagtattagagtggaggtttgacagccgcctagcatttcatcacatggcccgaga
gctgcatccggactgtactgggtctctctggttagaccagatctgagcctgggagctctctggctaactagggaacccactgcttaagcctca
ataaagcttgccttgagtgcttcaagtagtgtgtgcccgtctgttgtgtgactctggtaactagagatccctcagacccttttagtcagtgtggaa
aatctctagcagggcccgtttaaacccgctgatcagcctcgactgtgccttctagttgccagccatctgttgtttgccccctccccgtgccttcc
ttgaccctggaaggtgccactcccactgtcctttcctaataaaaatgaggaaattgcatcgcattgtctgagtaggtgtcattctattctgggggt
ggggtggggcaggacagcaaggggggaggattgggaagacaatagcaggcatgctggggatgcggtgggctctatggcttctgaggcg
gaaagaaccagctggggctctaggggggtatccccacgcgcccctgtagcggcgcattaagcgcggcgggtgtggtggttacgcgcagcgt
gaccgctacacttgccagcgcccagcgcccgctcctttcgctttcttcccttcctttctcgccacgttcgccggctttccccgtcaagctctaa
atcgggggctccctttaggggttccgatttagtgctttacggcacctcgaccccaaaaaacttgattagggtgatggttcacgtagtgggccatc
gccctgatagacggttttttcgccctttgacgttggagtccacgttctttaatagtggactcttgttccaaactggaacaacactcaaccctatctc
ggtctattctttgatttataagggattttgccgatttcggcctattggttaaaaaatgagctgatttaacaaaaatttaacgcgaattaattctgtgg
aatgtgtgtcagttagggtgtggaaagtccccaggctccccagcaggcagaagtatgcaaagcatgcatctcaattagtcagcaaccaggt
gtggaaagtccccaggctccccagcaggcagaagtatgcaaagcatgcatctcaattagtcagcaaccatagtcccgcccctaactccgcc
catcccgccccaactccgcccagttccgcccattctccgccccatggctgactaattttttttatttatgcagaggccgaggccgcctctgcct
ctgagctattccagaagtagtgaggaggctttttggaggcctaggcttttgcaaaaagctcccgggagcttgtatatccattttcggatctgat
cagcacgtgttgacaattaatcatcggcatagtatatcggcatagtataatacgacaaggtgaggaactaaaccatggccaagttgaccagt
gccgttccggtgctcaccgcgcgcgacgtcgccggagcggtcgagttctggaccgaccggctcgggttctcccgggacttcgtggagga
cgacttcgccggtgtggtccgggacgacgtgaccctgttcatcagcgcggtccaggaccaggtggtgccggacaacaccctggcctggg
tgtgggtgcgcggcctggacgagctgtacgccgagtggtcggaggtcgtgtccacgaacttccgggacgcctccgggccggccatgacc
gagatcggcgagcagccgtgggggcgggagttcgccctgcgcgacccggccggcaactgcgtgcacttcgtggccgaggagcagga
ctgacacgtgctacgagatttcgattccaccgccgccttctatgaaaggttgggcttcggaatcgtttccgggacgccggctggatgatcct
ccagcgcggggatctcatgctggagttcttcgcccacccaacttgtttattgcagcttataatggttacaaataaagcaatagcatcacaaatt
tcacaaataaagcatttttttcactgcattctagttgtggtttgtccaaactcatcaatgtatcttatcatgtctgtataccgtcgacctctagctaga
gcttggcgtaatcatggtcatagctgtttcctgtgtgaaattgttatccgctcacaattccacacaacatacgagccggaagcataaagtgtaaa
gcctggggtgcctaatgagtgagctaactcacattaattgcgttgcgctcactgcccgctttccagtcgggaaacctgtcgtgccagctgcatt
aatgaatcggccaacgcgcggggagaggcggtttgcgtattgggcgctcttccgcttcctcgctcactgactcgctgcgctcggtcgttcgg
ctgcggcgagcggtatcagctcactcaaaggcggtaatacggttatccacagaatcaggggataacgcaggaaagaacatgtgagcaaa
aggccagcaaaaggccaggaaccgtaaaaaggccgcgttgctggcgtttttccataggctccgcccccctgacgagcatcacaaaaatcg
acgctcaagtcagaggtggcgaaacccgacaggactataaagataccaggcgtttccccctggaagctccctcgtgcgctctcctgttccg
accctgccgcttaccggatacctgtccgcctttctcccttcgggaagcgtggcgctttctcatagctcacgctgtaggtatctcagttcggtgta
ggtcgttcgctccaagctgggctgtgtgcacgaaccccccgttcagcccgaccgctgcgccttatccggtaactatcgtcttgagtccaacc
cggtaagacacgacttatcgccactggcagcagccactggtaacaggattagcagagcgaggtatgtaggcggtgctacagagttcttgaa
gtggtggcctaactacggctacactagaagaacagtatttggtatctgcgctctgctgaagccagttaccttcggaaaaagagttggtagctct
tgatccggcaaacaaaccaccgctggtagcggtggtttttttgtttgcaagcagcagattacgcgcagaaaaaaaggatctcaagaagatcc
tttgatcttttctacggggtctgacgctcagtggaacgaaaactcacgttaagggattttggtcatgagattatcaaaaaggatcttcacctagat
ccttttaaattaaaaatgaagttttaaatcaatctaaagtatatatgagtaaacttggtctgacagttaccaatgcttaatcagtgaggcacctatct

FIGURE 9R

TABLE 9G continued (SEQ. ID. NO. 13, continued)
cagcgatctgtctatttcgttcatccatagttgcctgactccccgtcgtgtagataactacgatacgggagggcttaccatctggccccagtgct
gcaatgataccgcgagacccacgctcaccggctccagatttatcagcaataaaccagccagccggaagggccgagcgcagaagtggtc
ctgcaactttatccgcctccatccagtctattaattgttgccgggaagctagagtaagtagttcgccagttaatagtttgcgcaacgttgttgcca
ttgctacaggcatcgtggtgtcacgctcgtcgtttggtatggcttcattcagctccggttcccaacgatcaaggcgagttacatgatcccccat
gttgtgcaaaaaagcggttagctccttcggtcctccgatcgttgtcagaagtaagttggccgcagtgttatcactcatggttatggcagcactg
cataattctcttactgtcatgccatccgtaagatgcttttctgtgactggtgagtactcaaccaagtcattctgagaatagtgtatgcggcgaccg
agttgctcttgcccggcgtcaatacgggataataccgcgccacatagcagaactttaaaagtgctcatcattggaaaacgttcttcggggcga
aaactctcaaggatcttaccgctgttgagatccagttcgatgtaacccactcgtgcacccaactgatcttcagcatctttactttcaccagcgttt
ctgggtgagcaaaaacaggaaggcaaaatgccgcaaaaaagggaataagggcgacacggaaatgttgaatactcatactcttccttttca
atattattgaagcatttatcagggttattgtctcatgagcggatacatatttgaatgtatttagaaaaataaacaaatagggggttccgcgcacattt
ccccgaaaagtgccacctgac

SEQUENCE LISTING

```
<160> NUMBER OF SEQ ID NOS: 31

<210> SEQ ID NO 1
<211> LENGTH: 238
<212> TYPE: PRT
<213> ORGANISM: Artificial Sequence
<220> FEATURE:
<223> OTHER INFORMATION: Fluorogen Activating Peptide (FAP) sequence

<400> SEQUENCE: 1

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Thr
            20                  25                  30

Tyr Trp Tyr Gln Gln Lys Ala Gly Gln Ala Pro Val Leu Val Ile Tyr
        35                  40                  45

Lys Asp Thr Glu Arg Pro Ser Gly Ile Pro Glu Arg Phe Ser Gly Thr
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Ser Tyr
                85                  90                  95

Val Phe Phe Gly Gly Gly Thr Lys Val Thr Val Leu Ser Gly Gly Gly
            100                 105                 110

Gly Pro Gly Gly Gly Ser Gly Gly Gly Ser Gly Gly Gly Ser Gly Gly
            115                 120                 125

Gly Ser Tyr Glu Leu Thr Gln Pro Pro Ser Val Ser Val Ser Pro Gly
        130                 135                 140

Gln Thr Ala Arg Ile Thr Cys Ser Gly Asp Ala Leu Pro Lys Gln Tyr
145                 150                 155                 160

Thr Tyr Trp Tyr Gln Gln Lys Ala Gly Gln Ala Pro Val Leu Val Ile
                165                 170                 175

Tyr Lys Asp Thr Glu Arg Pro Ser Gly Ile Pro Glu Arg Phe Ser Gly
            180                 185                 190

Thr Ser Ser Gly Thr Thr Val Thr Leu Thr Ile Ser Gly Val Gln Ala
        195                 200                 205

Glu Asp Glu Ala Asp Tyr Tyr Cys Gln Ser Ala Asp Ser Ser Gly Ser
```

```
            210                 215                 220
Tyr Val Phe Phe Gly Gly Gly Thr Lys Val Thr Val Leu Ser
225                 230                 235

<210> SEQ ID NO 2
<211> LENGTH: 238
<212> TYPE: PRT
<213> ORGANISM: Artificial Sequence
<220> FEATURE:
<223> OTHER INFORMATION: Fluorogen Activating Peptide (FAP) sequence

<400> SEQUENCE: 2

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Thr
            20                  25                  30

Tyr Trp Tyr Gln Gln Lys Ala Gly Gln Ala Pro Val Leu Val Ile Tyr
        35                  40                  45

Lys Asp Thr Glu Arg Pro Ser Gly Ile Pro Glu Arg Phe Ser Gly Thr
50                  55                  60

Ser Ser Gly Thr Thr Ala Thr Leu Thr Ile Ser Gly Val Gln Ala Glu
65                  70                  75                  80

Asp Glu Ala Asp Tyr Tyr Cys Gln Ser Ala Asp Ser Ser Gly Ser Tyr
                85                  90                  95

Val Phe Phe Gly Gly Gly Thr Lys Val Thr Val Leu Ser Gly Gly Gly
            100                 105                 110

Gly Pro Gly Gly Gly Ser Gly Gly Ser Gly Gly Ser Gly Gly Ser Gly
        115                 120                 125

Gly Ser Tyr Glu Leu Thr Gln Pro Pro Ser Val Ser Val Ser Pro Gly
    130                 135                 140

Gln Thr Ala Arg Ile Thr Cys Ser Gly Asp Ala Leu Pro Lys Gln Tyr
145                 150                 155                 160

Thr Tyr Trp Tyr Gln Gln Lys Ala Gly Gln Ala Pro Val Leu Val Ile
                165                 170                 175

Tyr Lys Asp Thr Glu Arg Pro Ser Gly Ile Pro Glu Arg Phe Ser Gly
            180                 185                 190

Thr Ser Ser Gly Thr Thr Val Thr Leu Thr Ile Ser Gly Val Gln Ala
        195                 200                 205

Glu Asp Glu Ala Asp Tyr Tyr Cys Gln Ser Ala Asp Ser Ser Gly Ser
    210                 215                 220

Tyr Val Phe Phe Gly Gly Gly Thr Lys Val Thr Val Leu Ser
225                 230                 235

<210> SEQ ID NO 3
<211> LENGTH: 238
<212> TYPE: PRT
<213> ORGANISM: Artificial Sequence
<220> FEATURE:
<223> OTHER INFORMATION: Fluorogen Activating Peptide (FAP) sequence

<400> SEQUENCE: 3

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Thr
            20                  25                  30

Tyr Trp Tyr Gln Gln Lys Ala Gly Gln Ala Pro Val Leu Val Ile Tyr
        35                  40                  45
```

| | | | | | | | | | | | |
|---|---|---|---|---|---|---|---|---|---|---|---|
|Lys|Asp|Thr|Glu|Arg|Pro|Ser|Gly|Ile|Pro|Glu|Arg|Phe|Ser|Gly|Thr|
| |50| | | |55| | | |60| | | | | | |

Lys Asp Thr Glu Arg Pro Ser Gly Ile Pro Glu Arg Phe Ser Gly Thr
       50                  55                  60

Ser Ser Gly Thr Thr Ala Thr Leu Thr Ile Ser Gly Val Gln Ala Glu
65                  70                  75                  80

Asp Glu Ala Asp Tyr Tyr Cys Gln Ser Ala Asp Ser Ser Gly Ser His
                85                  90                  95

Val Phe Phe Gly Gly Gly Thr Lys Val Thr Val Leu Ser Gly Gly Gly
            100                 105                 110

Gly Pro Gly Gly Gly Ser Gly Gly Ser Gly Gly Ser Gly Gly
            115                 120                 125

Gly Ser Tyr Glu Leu Thr Gln Pro Pro Ser Val Ser Val Ser Pro Gly
    130                 135                 140

Gln Thr Ala Arg Ile Thr Cys Ser Gly Asp Ala Leu Pro Lys Gln Tyr
145                 150                 155                 160

Thr Tyr Trp Tyr Gln Gln Lys Ala Gly Gln Ala Pro Val Leu Val Ile
                165                 170                 175

Tyr Lys Asp Thr Glu Arg Pro Ser Gly Ile Pro Glu Arg Phe Ser Gly
            180                 185                 190

Thr Ser Ser Gly Thr Thr Ala Thr Leu Thr Ile Ser Gly Val Gln Ala
    195                 200                 205

Glu Asp Glu Ala Asp Tyr Tyr Cys Gln Ser Ala Asp Ser Ser Gly Ser
210                 215                 220

His Val Phe Phe Gly Gly Gly Thr Lys Val Thr Val Leu Ser
225                 230                 235

<210> SEQ ID NO 4
<211> LENGTH: 714
<212> TYPE: DNA
<213> ORGANISM: Artificial Sequence
<220> FEATURE:
<223> OTHER INFORMATION: Fluorogen Activating Peptide (FAP) sequence

<400> SEQUENCE: 4
tcttacgaat taacacaacc tccatctgtt tctgtttctc caggtcaaac tgctagaatt        60
acttgttctg gtgatgcttt gccaaaacaa tacacttact ggtatcaaca aaaagctggt       120
caagctccag ttttggttat ttataaagat actgaaagac catctggtat tccagaaaga       180
ttctcaggta cttcttctgg tactactgtt actttgacta tttctggtgt tcaagctgaa       240
gatgaagctg attattattg tcaatctgct gattcttctg gttcttatgt attttttcggt      300 ggtggtacta agttactgt tttgtctggt ggaggaggcc aggtggcgg ttcaggtgga         360 ggttctggcg gaggttctgg tggaggttcc tatgagttga ctcagccacc ctcggtgtca       420
gtgtccccag acagacggc caggatcacc tgctctggag atgcattgcc aaagcaatat       480
acttattggt accagcagaa ggcaggccag gcccctgtct ggtgatata taaagacact       540 gagaggccct cagggatccc tgagcgattc tctggtacca gttcagggac aacagtcaca       600
ttgaccatca gtggagtcca ggcagaagac gaggctgact attactgtca atcagcagac       660
agcagtggtt cctatgtttt cttcggcgga gggaccaagg tgaccgtact atcc             714

<210> SEQ ID NO 5
<211> LENGTH: 714
<212> TYPE: DNA
<213> ORGANISM: Artificial Sequence
<220> FEATURE:
<223> OTHER INFORMATION: Fluorogen Activating Peptide (FAP) sequence

<400> SEQUENCE: 5

```
tcttacgaat taacacaacc tccatctgtt tctgtttctc caggtcaaac tgctagaatt      60
acttgttctg gtgatgcttt gccaaaacaa tacacttact ggtatcaaca aaaagctggt     120
caagctccag ttttggttat ttataaagat actgaaagac catctggtat tccagaaaga     180
ttctcaggta cttcttctgg tactactgct actttgacta tttctggtgt tcaagctgaa     240
gatgaagctg attattattg tcaatctgct gattcttctg ttcttatgt attttttcggt     300 ggtggtacta aagttactgt tttgtctggt ggaggaggcc aggtggcgg ttcaggtgga     360 ggttctggcg gaggttctgg tggaggttcc tatgagttga ctcagccacc ctcggtgtca     420
gtgtccccag acagacggc caggatcacc tgctctggag atgcattgcc aaagcaatat     480
acttattggt accagcagaa ggcaggccag gcccctgtct tggtgatata taagacact     540 gagaggccct cagggatccc tgagcgattc tctggtacca gttcagggac aacagtcaca     600
ttgaccatca gtggagtcca ggcagaagac gaggctgact attactgtca atcagcagac     660
agcagtggtt cctatgtttt cttcggcgga gggaccaagg tgaccgtact atcc            714

<210> SEQ ID NO 6
<211> LENGTH: 714
<212> TYPE: DNA
<213> ORGANISM: Artificial Sequence
<220> FEATURE:
<223> OTHER INFORMATION: Fluorogen Activating Peptide (FAP) sequence

<400> SEQUENCE: 6
tcttacgaat taacacaacc tccatctgtt tctgtttctc caggtcaaac tgctagaatt      60
acttgttctg gtgatgcttt gccaaaacaa tacacttact ggtatcaaca aaaagctggt     120
caagctccag ttttggttat ttataaagat actgaaagac catctggtat tccagaaaga     180
ttctcaggta cttcttctgg tactactgct actttgacta tttctggtgt tcaagctgaa     240
gatgaagctg attattattg tcaatctgct gattcttctg ttctcatgt attttttcggt     300 ggtggtacta aagttactgt tttgtctggt ggaggaggcc aggtggcgg ttcaggtgga     360 ggttctggcg gaggttctgg tggaggttcc tatgagttga ctcagccacc ctcggtgtca     420
gtgtccccag acagacggc caggatcacc tgctctggag atgcattgcc aaagcaatat     480
acttattggt accagcagaa ggcaggccag gcccctgtct tggtgatata taagacact     540 gagaggccct cagggatccc tgagcgattc tctggtacca gttcagggac aacagccaca     600
ttgaccatca gtggagtcca ggcagaagac gaggctgact attactgtca atcagcagac     660
agcagtggtt cccacgtttt cttcggcgga gggaccaagg tgaccgtact atcc            714

<210> SEQ ID NO 7
<211> LENGTH: 5011
<212> TYPE: DNA
<213> ORGANISM: Artificial Sequence
<220> FEATURE:
<223> OTHER INFORMATION: Vector pOIdL9.2N

<400> SEQUENCE: 7
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
```

```
catgacccta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggtcgcca ccatggagac agacacactc ctgctatggg tactgctgct ctggttcca    660
ggttccactg gtgactatcc atatgatgtt ccagattatg cttctagctc ttacgaatta    720
acacaacctc catctgtttc tgtttctcca ggtcaaactg ctagaattac ttgttctggt    780
gatgctttgc caaaacaata cacttactgg tatcaacaaa agctggtca agctccagtt    840
ttggttattt ataaagatac tgaaagacca tctggtattc agaaagatt ctcaggtact    900
tcttctggta ctactgctac tttgactatt tctggtgttc aagctgaaga tgaagctgat    960
tattattgtc aatctgctga ttcttctggt tcttatgtat ttttcggtgg tggtactaaa   1020
gttactgttt tgtctggtgg aggaggccca ggtggcggtt caggtggagg ttctggcgga   1080
ggttctggtg gaggttccta tgagttgact cagccaccct cggtgtcagt gtccccagga   1140
cagacggcca ggatcacctg ctctggagat gcattgccaa agcaatatac ttattggtac   1200
cagcagaagg caggccaggc ccctgtcttg gtgatatata agacactga gaggccctca   1260
gggatccctg agcgattctc tggtaccagt tcagggacaa cagtcacatt gaccatcagt   1320
ggagtccagg cagaagacga ggctgactat tactgtcaat cagcagacag cagtggttcc   1380
tatgtttttct tcggcggagg gaccaaggtg accgtactat ccgaggcgg tgggaagaag   1440
ttccccccag aagaccctcc tgatagcaag aacacacttg tgctctttgg ggcaggattc   1500
ggcgcagtaa taacagtcgt cgtcatcgtt gtcatcatca aatgcttctg taagcacaga   1560
agctgtttca aagaaaatga ggcaagcaga gaaacaaaca acagccttac cttcgggcct   1620
gaagaagcat tagctgaaca gaccgtcttc cttactagtt aatagcccgg gatccaccgg   1680
atctagataa ctgatcataa tcagccatac cacatttgta gaggttttac ttgctttaaa   1740
aaacctccca cacctccccc tgaacctgaa acataaaatg aatgcaattg ttgttgttaa   1800
cttgtttatt gcagcttata atggttacaa ataaagcaat agcatcacaa atttcacaaa   1860
taaagcattt ttttcactgc attctagttg tggtttgtcc aaactcatca atgtatctta   1920
acgcgtaaat tgtaagcgtt aatattttgt taaaattcgc gttaaatttt tgttaaatca   1980
gctcatttt taaccaatag gccgaaatcg gcaaaatccc ttataaatca aagaataga   2040
ccgagatagg gttgagtgtt gttccagttt ggaacaagag tccactatta agaacgtgg   2100
actccaacgt caaagggcga aaaccgtct atcagggcga tggcccacta cgtgaaccat   2160
cacccctaatc aagttttttg gggtcgaggt gccgtaaagc actaaatcgg aaccctaaag   2220
ggagccccg atttagagct tgacggggaa agccggcgaa cgtggcgaga aggaaggga   2280
agaaagcgaa aggagcgggc gctagggcgc tggcaagtgt agcggtcacg ctgcgcgtaa   2340
ccaccacacc cgccgcgctt aatgcgccgc tacagggcgc gtcaggtggc acttttcggg   2400
gaaatgtgcg cggaacccct atttgtttat ttttctaaat acattcaaat atgtatccgc   2460
tcatgagaca ataaccctga taaatgcttc aataatattg aaaaaggaag agtcctgagg   2520
cggaaagaac cagctgtgga atgtgtgtca gttagggtgt ggaaagtccc caggctcccc   2580
agcaggcaga agtatgcaaa gcatgcatct caattagtca gcaaccaggt gtggaaagtc   2640
cccaggctcc ccagcaggca gaagtatgca aagcatgcat ctcaattagt cagcaaccat   2700
```

-continued

```
agtcccgccc ctaactccgc ccatcccgcc cctaactccg cccagttccg cccattctcc    2760
gccccatggc tgactaattt tttttattta tgcagaggcc gaggccgcct cggcctctga    2820
gctattccag aagtagtgag gaggcttttt tggaggccta ggcttttgca aagatcgatc    2880
aagagacagg atgaggatcg tttcgcatga ttgaacaaga tggattgcac gcaggttctc    2940
cggccgcttg ggtggagagg ctattcggct atgactgggc acaacagaca atcggctgct    3000
ctgatgccgc cgtgttccgg ctgtcagcgc aggggcgccc ggttcttttt gtcaagaccg    3060
acctgtccgg tgccctgaat gaactgcaag acgaggcagc gcggctatcg tggctggcca    3120
cgacgggcgt tccttgcgca gctgtgctcg acgttgtcac tgaagcggga agggactggc    3180
tgctattggg cgaagtgccg gggcaggatc tcctgtcatc tcaccttgct cctgccgaga    3240
aagtatccat catggctgat gcaatgcggc ggctgcatac gcttgatccg gctacctgcc    3300
cattcgacca ccaagcgaaa catcgcatcg agcgagcacg tactcggatg aagccggtc    3360 ttgtcgatca ggatgatctg gacgaagagc atcaggggct cgcgccagcc gaactgttcg    3420
ccaggctcaa ggcgagcatg cccgacggcg aggatctcgt cgtgacccat ggcgatgcct    3480
gcttgccgaa tatcatggtg gaaaatggcc gcttttctgg attcatcgac tgtgccggc    3540 tgggtgtggc ggaccgctat caggacatag cgttggctac ccgtgatatt gctgaagagc    3600
ttggcggcga atgggctgac cgcttcctcg tgctttacgg tatcgccgct cccgattcgc    3660
agcgcatcgc cttctatcgc cttcttgacg agttcttctg agcgggactc tggggttcga    3720
aatgaccgac caagcgacgc ccaacctgcc atcacgagat ttcgattcca ccgccgcctt    3780
ctatgaaagg ttgggcttcg gaatcgtttt ccgggacgcc ggctggatga tcctccagcg    3840
cggggatctc atgctggagt tcttcgccca ccctaggggg aggctaactg aaacacggaa    3900
ggagacaata ccggaaggaa cccgcgctat gacggcaata aaaagacaga ataaaacgca    3960
cggtgttggg tcgtttgttc ataaacgcgg ggttcggtcc cagggctggc actctgtcga    4020
taccccaccg agaccccatt ggggccaata cgcccgcgtt tcttccttt ccccacccca    4080 cccccaagt tcgggtgaag gcccagggct cgcagccaac gtcggggcgg caggccctgc    4140
catagcctca ggttactcat atatacttta gattgattta aaacttcatt tttaatttaa    4200
aaggatctag gtgaagatcc ttttgataa tctcatgacc aaaatccctt aacgtgagtt    4260
ttcgttccac tgagcgtcag accccgtaga aagatcaaa ggatcttctt gagatccttt    4320
ttttctgcgc gtaatctgct gcttgcaaac aaaaaaacca ccgctaccag cggtggtttg    4380
tttgccggat caagagctac caactctttt tccgaaggta actggcttca gcagagcgca    4440
gataccaaat actgtccttc tagtgtagcc gtagttaggc caccacttca agaactctgt    4500
agcaccgcct acatacctcg ctctgctaat cctgttacca gtggctgctg ccagtggcga    4560
taagtcgtgt cttaccgggt tggactcaag acgatagtta ccggataagg cgcagcggtc    4620
gggctgaacg gggggttcgt gcacacagcc cagcttggag cgaacgacct acaccgaact    4680 gagatacctac cagcgtgagc tatgagaaag cgccacgctt cccgaaggga aaaggcgga    4740 caggtatccg gtaagcggca gggtcggaac aggagagcgc acgagggagc ttccaggggg    4800
aaacgcctgg tatctttata gtcctgtcgg gtttcgccac ctctgacttg agcgtcgatt    4860
tttgtgatgc tcgtcagggg ggcggagcct atggaaaaac gccagcaacg cggccttttt    4920
acggttcctg gccttttgct ggccttttgc tcacatgttc tttcctgcgt tatcccctga    4980
ttctgtggat aaccgtatta ccgccatgca t                                   5011
```

<210> SEQ ID NO 8
<211> LENGTH: 5011
<212> TYPE: DNA
<213> ORGANISM: Artificial Sequence
<220> FEATURE:
<223> OTHER INFORMATION: Vector pOIdL9.5N

<400> SEQUENCE: 8

| | | | | | |
|---|---|---|---|---|---|
| tagttattaa | tagtaatcaa | ttacggggtc | attagttcat | agcccatata | tggagttccg | 60 |
| cgttacataa | cttacggtaa | atggcccgcc | tggctgaccg | cccaacgacc | cccgcccatt | 120 |
| gacgtcaata | atgacgtatg | ttcccatagt | aacgccaata | gggactttcc | attgacgtca | 180 |
| atgggtggag | tatttacggt | aaactgccca | cttggcagta | catcaagtgt | atcatatgcc | 240 |
| aagtacgccc | cctattgacg | tcaatgacgg | taaatggccc | gcctggcatt | atgcccagta | 300 |
| catgacctta | tgggactttc | ctacttggca | gtacatctac | gtattagtca | tcgctattac | 360 |
| catggtgatg | cggttttggc | agtacatcaa | tgggcgtgga | tagcggtttg | actcacgggg | 420 |
| atttccaagt | ctccacccca | ttgacgtcaa | tgggagtttg | ttttggcacc | aaaatcaacg | 480 |
| ggactttcca | aaatgtcgta | acaactccgc | cccattgacg | caaatgggcg | gtaggcgtgt | 540 |
| acggtgggag | gtctatataa | gcagagctgg | tttagtgaac | cgtcagatcc | gctagcgcta | 600 |
| ccggtcgcca | ccatggagac | agacacactc | ctgctatggg | tactgctgct | ctgggttcca | 660 |
| ggttccactg | tgactatcc | atatgatgtt | ccagattatg | cttctagctc | ttacgaatta | 720 |
| acacaacctc | catctgtttc | tgtttctcca | ggtcaaactg | ctagaattac | ttgttctggt | 780 |
| gatgctttgc | caaacaata | cacttactgg | tatcaacaaa | agctggtca | agctccagtt | 840 |
| ttggttattt | ataaagatac | tgaaagacca | tctggtattc | cagaaagatt | ctcaggtact | 900 |
| tcttctggta | ctactgctac | tttgactatt | tctggtgttc | aagctgaaga | tgaagctgat | 960 |
| tattattgtc | aatctgctga | ttcttctggt | tctcatgtat | ttttcggtgg | tggtactaaa | 1020 |
| gttactgttt | tgtctggtgg | aggaggccca | ggtggcggtt | caggtggagg | ttctggcgga | 1080 |
| ggttctggtg | gaggttccta | tgagttgact | cagccaccct | cggtgtcagt | gtccccagga | 1140 |
| cagacggcca | ggatcacctg | ctctggagat | gcattgccaa | agcaatatac | ttattggtac | 1200 |
| cagcagaagg | caggccaggc | ccctgtcttg | gtgatatata | aagacactga | gaggccctca | 1260 |
| gggatccctg | agcgattctc | tggtaccagt | tcagggacaa | cagccacatt | gaccatcagt | 1320 |
| ggagtccagg | cagaagacga | ggctgactat | tactgtcaat | cagcagacag | cagtggttcc | 1380 |
| cacgtttttct | tcggcggagg | gaccaaggtg | accgtactat | ccggaggcgg | tgggaagaag | 1440 |
| ttcccccccag | aagaccctcc | tgatagcaag | aacacacttg | tgctctttgg | ggcaggattc | 1500 |
| ggcgcagtaa | taacagtcgt | cgtcatcgtt | gtcatcatca | aatgcttctg | taagcacaga | 1560 |
| agctgtttca | gaagaaatga | ggcaagcaga | gaaacaaaca | acagccttac | cttcgggcct | 1620 |
| gaagaagcat | tagctgaaca | gaccgtcttc | cttactagtt | aatagcccgg | gatccaccgg | 1680 |
| atctagataa | ctgatcataa | tcagccatac | cacatttgta | gaggttttac | ttgctttaaa | 1740 |
| aaacctccca | cacctcccc | tgaacctgaa | acataaaatg | aatgcaattg | ttgttgttaa | 1800 |
| cttgtttatt | gcagcttata | atggttacaa | ataaagcaat | agcatcacaa | atttcacaaa | 1860 |
| taaagcattt | ttttcactgc | attctagttg | tggtttgtcc | aaactcatca | atgtatctta | 1920 |
| acgcgtaaat | tgtaagcgtt | aatattttgt | taaaattcgc | gttaaatttt | tgttaaatca | 1980 |
| gctcattttt | taaccaatag | gccgaaatcg | gcaaaatccc | ttataaatca | aagaatagac | 2040 |
| ccgagatagg | gttgagtgtt | gttccagttt | ggaacaagag | tccactatta | aagaacgtgg | 2100 |

```
actccaacgt caaagggcga aaaaccgtct atcagggcga tggcccacta cgtgaaccat   2160 cacctaatc aagttttttg gggtcgaggt gccgtaaagc actaaatcgg aaccctaaag   2220 ggagccccg atttagagct tgacggggaa agccggcgaa cgtggcgaga aaggaaggga    2280
agaaagcgaa aggagcgggc gctagggcgc tggcaagtgt agcggtcacg ctgcgcgtaa   2340
ccaccacacc cgccgcgctt aatgcgccgc tacagggcgc gtcaggtggc acttttcggg   2400
gaaatgtgcg cggaaccct atttgtttat ttttctaaat acattcaaat atgtatccgc    2460
tcatgagaca ataaccctga taaatgcttc aataatattg aaaaggaag agtcctgagg    2520 cggaaagaac cagctgtgga atgtgtgtca gttagggtgt ggaaagtccc caggctcccc   2580
agcaggcaga agtatgcaaa gcatgcatct caattagtca gcaaccaggt gtggaaagtc   2640
cccaggctcc ccagcaggca gaagtatgca aagcatgcat ctcaattagt cagcaaccat   2700
agtcccgccc ctaactccgc ccatcccgcc cctaactccg cccagttccg cccattctcc   2760
gccccatggc tgactaattt tttttattta tgcagaggcc gaggccgcct cggcctctga   2820
gctattccag aagtagtgag gaggcttttt tggaggccta ggcttttgca aagatcgatc   2880
aagagacagg atgaggatcg tttcgcatga ttgaacaaga tggattgcac gcaggttctc   2940
cggccgcttg ggtggagagg ctattcggct atgactgggc acaacagaca atcggctgct   3000
ctgatgccgc cgtgttccgg ctgtcagcgc aggggcgccc ggttcttttt gtcaagaccg   3060
acctgtccgg tgccctgaat gaactgcaag acgaggcagc gcggctatcg tggctggcca   3120
cgacgggcgt tccttgcgca gctgtgctcg acgttgtcac tgaagcggga agggactggc   3180
tgctattggg cgaagtgccg gggcaggatc tcctgtcatc tcaccttgct cctgccgaga   3240
aagtatccat catggctgat gcaatgcggc ggctgcatac gcttgatccg gctacctgcc   3300
cattcgacca ccaagcgaaa catcgcatcg agcgagcacg tactcggatg gaagccggtc   3360
ttgtcgatca ggatgatctg gacgaagagc atcaggggct cgcgccagcc gaactgttcg   3420
ccaggctcaa ggcgagcatg cccgacggcg aggatctcgt cgtgacccat ggcgatgcct   3480
gcttgccgaa tatcatggtg gaaaatggcc gcttttctgg attcatcgac tgtggccggc   3540
tgggtgtggc ggaccgctat caggacatag cgttggctac ccgtgatatt gctgaagagc   3600
ttggcggcga atgggctgac cgcttcctcg tgctttacgg tatcgccgct cccgattcgc   3660
agcgcatcgc cttctatcgc cttcttgacg agttcttctg agcgggactc tggggttcga   3720
aatgaccgac caagcgacgc ccaacctgcc atcacgagat ttcgattcca ccgccgcctt   3780
ctatgaaagg ttgggcttcg gaatcgtttt ccgggacgcc ggctggatga tcctccagcg   3840
cggggatctc atgctggagt tcttcgccca ccctaggggg aggctaactg aaacacggaa   3900
ggagacaata ccggaaggaa cccgcgctat gacggcaata aaaagacaga ataaaacgca   3960
cggtgttggg tcgtttgttc ataaacgcgg ggttcggtcc cagggctggc actctgtcga   4020 tacccaccg agacccatt ggggccaata cgcccgcgtt tcttcctttt ccccacccca    4080
ccccccaagt tcgggtgaag gcccagggct cgcagccaac gtcggggcgg caggccctgc   4140
catagcctca ggttactcat atatacttta gattgattta aaacttcatt tttaatttaa   4200
aaggatctag gtgaagatcc ttttttgataa tctcatgacc aaaatccctt aacgtgagtt   4260
ttcgttccac tgagcgtcag accccgtaga aagatcaaa ggatcttctt gagatccttt    4320
ttttctgcgc gtaatctgct gcttgcaaac aaaaaaacca ccgctaccag cggtggtttg   4380
tttgccggat caagagctac caactctttt tccgaaggta actggcttca gcagagcgca   4440
```

| | |
|---|---:|
| gataccaaat actgtccttc tagtgtagcc gtagttaggc caccacttca agaactctgt | 4500 |
| agcaccgcct acatacctcg ctctgctaat cctgttacca gtggctgctg ccagtggcga | 4560 |
| taagtcgtgt cttaccgggt tggactcaag acgatagtta ccggataagg cgcagcggtc | 4620 |
| gggctgaacg gggggttcgt gcacacagcc cagcttggag cgaacgacct acaccgaact | 4680 |
| gagataccta cagcgtgagc tatgagaaag cgccacgctt cccgaaggga gaaaggcgga | 4740 |
| caggtatccg gtaagcggca gggtcggaac aggagagcgc acgagggagc ttccaggggg | 4800 |
| aaacgcctgg tatctttata gtcctgtcgg gtttcgccac ctctgacttg agcgtcgatt | 4860 |
| tttgtgatgc tcgtcagggg ggcggagcct atggaaaaac gccagcaacg cggccttttt | 4920 |
| acggttcctg gccttttgct ggccttttgc tcacatgttc tttcctgcgt tatcccctga | 4980 |
| ttctgtggat aaccgtatta ccgccatgca t | 5011 |

<210> SEQ ID NO 9
<211> LENGTH: 5452
<212> TYPE: DNA
<213> ORGANISM: Artificial Sequence
<220> FEATURE:
<223> OTHER INFORMATION: Vector pCYdL9.2eGFP

<400> SEQUENCE: 9

| | |
|---|---:|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta caactccgcc ccattgacg caaatgggcg gtaggcgtgt | 540 |
| acggtgggag gtctatataa gcagagctgg tttagtgaac cgtcagatcc gctagcgcta | 600 |
| ccggtcgcca ccatggcctc ttacgaatta acacaacctc catctgtttc tgtttctcca | 660 |
| ggtcaaactg ctagaattac ttgttctggt gatgctttgc caaaacaata cacttactgg | 720 |
| tatcaacaaa agctggtcaa gctccagtt tggttatt ataaagatac tgaaagacca | 780 |
| tctggtattc cagaaagatt ctcaggtact cttctggta ctactgctac tttgactatt | 840 |
| tctggtgttc aagctgaaga tgaagctgat tattattgtc aatctgctga ttcttctggt | 900 |
| tcttatgtat ttttcggtgg tggtactaaa gttactgttt tgtctggtgg aggaggccca | 960 |
| ggtggcggtt caggtggagg ttctggcgga ggttctggtg gaggttccta tgagttgact | 1020 |
| cagccaccct cggtgtcagt gtccccagga cagacggcca ggatcacctg ctctggagat | 1080 |
| gcattgccaa agcaatatac ttattggtac cagcagaagg caggccaggc ccctgtcttg | 1140 |
| gtgatatata agacactga gaggccctca gggatccctg agcgattctc tggtaccagt | 1200 |
| tcagggacaa cagtcacatt gaccatcagt ggagtccagg cagaagacga ggctgactat | 1260 |
| tactgtcaat cagcagacag cagtggttcc tatgtttct tcggcggagg gaccaaggtg | 1320 |
| accgtactat ccgaggggcg cgcctctggt ggcggagctt ctggaggtgg ttctggcggc | 1380 |
| tctggtatgg tgagcaaggg cgaggagctg ttcaccgggg tggtgcccat cctggtcgag | 1440 |
| ctggacggcg acgtaaacgg ccacaagttc agcgtgtccg gcgagggcga gggcgatgcc | 1500 |

```
acctacggca agctgaccct gaagttcatc tgcaccaccg gcaagctgcc cgtgccctgg      1560 cccacccteg tgaccaccct gacctacggc gtgcagtgct tcagccgcta ccccgaccac      1620
atgaagcagc acgacttctt caagtccgcc atgcccgaag gctacgtcca ggagcgcacc      1680
atcttcttca aggacgacgg caactacaag acccgcgccg aggtgaagtt cgagggcgac      1740
accctggtga accgcatcga gctgaagggc atcgacttca aggaggacgg caacatcctg      1800
gggcacaagc tggagtacaa ctacaacagc cacaacgtct atatcatggc cgacaagcag      1860
aagaacggca tcaaggtgaa cttcaagatc cgccacaaca tcgaggacgg cagcgtgcag      1920
ctcgccgacc actaccagca gaacaccccc atcggcgacg gccccgtgct gctgcccgac      1980
aaccactacc tgagcaccca gtccgccctg agcaaagacc ccaacgagaa gcgcgatcac      2040
atggtcctgc tggagttcgt gaccgccgcc gggatcactc tcggcatgga cgagctgtac      2100
aagtaacccg ggatccaccg gatctagata actgatcata atcagccata ccacatttgt      2160
agaggtttta cttgctttaa aaaacctccc acacctcccc ctgaacctga aacataaaat      2220
gaatgcaatt gttgttgtta acttgtttat tgcagcttat aatggttaca ataaagcaa      2280 tagcatcaca aatttcacaa ataaagcatt ttttcactg cattctagtt gtggtttgtc      2340
caaactcatc aatgtatctt aacgcgtaaa ttgtaagcgt taatattttg ttaaaattcg      2400
cgttaaattt tgttaaatc agctcatttt ttaaccaata ggccgaaatc ggcaaaatcc      2460
cttataaatc aaaagaatag accgagatag ggttgagtgt tgttccagtt tggaacaaga      2520
gtccactatt aaagaacgtg gactccaacg tcaaagggcg aaaaaccgtc tatcagggcg      2580
atggcccact acgtgaacca tcaccctaat caagttttt ggggtcgagg tgccgtaaag      2640
cactaaatcg gaaccctaaa gggagccccc gatttagagc ttgacgggga agccggcga      2700 acgtggcgag aaaggaaggg aagaaagcga aggagcggg cgtagggcg ctggcaagtg      2760 tagcggtcac gctgcgcgta accaccacac ccgccgcgct taatgcgccg ctacagggcg      2820
cgtcaggtgg cactttcgg ggaaatgtgc gcggaacccc tatttgttta ttttctaaa      2880 tacattcaaa tatgtatccg ctcatgagac aataaccctg ataaatgctt caataatatt      2940 gaaaaggaa gagtcctgag gcggaaagaa ccagctgtgg aatgtgtgtc agttagggtg      3000
tggaaagtcc ccaggctccc cagcaggcag aagtatgcaa agcatgcatc tcaattagtc      3060
agcaaccagg tgtggaaagt ccccaggctc cccagcaggc agaagtatgc aaagcatgca      3120
tctcaattag tcagcaacca tagtcccgcc cctaactccg cccatcccgc cctaactcc      3180 gcccagttcc gcccattctc cgccccatgg ctgactaatt ttttttattt atgcagaggc      3240
cgaggccgcc tcggcctctg agctattcca gaagtagtga ggaggctttt ttggaggcct      3300
aggcttttgc aaagatcgat caagagacag gatgaggatc gtttcgcatg attgaacaag      3360
atggattgca cgcaggttct ccggccgctt gggtggagag gctattcggc tatgactggg      3420
cacaacagac aatcggctgc tctgatgccg ccgtgttccg gctgtcagcg caggggcgcc      3480
cggttctttt tgtcaagacc gacctgtccg gtgccctgaa tgaactgcaa gacgaggcag      3540
cgcggctatc gtggctggcc acgacgggcg ttccttgcgc agctgtgctc gacgttgtca      3600
ctgaagcggg aagggactgg ctgctattgg gcgaagtgcc ggggcaggat tcctgtcat      3660 ctcaccttgc tcctgccgag aaagtatcca tcatggctga tgcaatgcgg cggctgcata      3720
cgcttgatcc ggctacctgc ccattcgacc accaagcgaa acatcgcatc gagcgagcac      3780
gtactcggat ggaagccggt cttgtcgatc aggatgatct ggacgaagag catcagggc      3840
```

-continued

```
tcgcgccagc cgaactgttc gccaggctca aggcgagcat gcccgacggc gaggatctcg    3900
tcgtgaccca tggcgatgcc tgcttgccga atatcatggt ggaaaatggc cgcttttctg    3960
gattcatcga ctgtggccgg ctgggtgtgg cggaccgcta tcaggacata gcgttggcta    4020
cccgtgatat tgctgaagag cttggcggcg aatgggctga ccgcttcctc gtgctttacg    4080
gtatcgccgc tcccgattcg cagcgcatcg ccttctatcg ccttcttgac gagttcttct    4140
gagcgggact ctggggttcg aaatgaccga ccaagcgacg cccaacctgc catcacgaga    4200
tttcgattcc accgccgcct ctatgaaaag gttgggcttc ggaatcgttt tccgggacgc    4260
cggctggatg atcctccagc gcggggatct catgctggag ttcttcgccc acctagggg    4320
gaggctaact gaaacacgga aggagacaat accggaagga accgcgcta tgacggcaat    4380
aaaaagacag aataaaacgc acggtgttgg gtcgtttgtt cataaacgcg gggttcggtc    4440
ccagggctgg cactctgtcg ataccccacc gagacccat tggggccaat acgcccgcgt    4500
ttcttccttt tccccacccc acccccaag ttcgggtgaa ggcccagggc tcgcagccaa    4560
cgtcggggcg gcaggccctg ccatagcctc aggttactca tatatacttt agattgattt    4620
aaaacttcat ttttaattta aaaggatcta ggtgaagatc cttttttgata atctcatgac    4680
caaaatccct taacgtgagt tttcgttcca ctgagcgtca daccccgtag aaaagatcaa    4740
aggatcttct tgagatcctt ttttctgcg cgtaatctgc tgcttgcaaa caaaaaaacc    4800
accgctacca gcggtggttt gtttgccgga tcaagagcta ccaactcttt ttccgaaggt    4860
aactggcttc agcagagcgc agataccaaa tactgtcctt ctagtgtagc cgtagttagg    4920
ccaccacttc aagaactctg tagcaccgcc tacatacctc gctctgctaa tcctgttacc    4980
agtggctgct gccagtggcg ataagtcgtg tcttaccggg ttggactcaa gacgatagtt    5040
accggataag gcgcagcggt cgggctgaac ggggggttcg tgcacacagc ccagcttgga    5100
gcgaacgacc tacaccgaac tgagatacct acagcgtgag ctatgagaaa gcgccacgct    5160
tcccgaaggg agaaaggcgg acaggtatcc ggtaagcggc agggtcggaa caggagagcg    5220
cacgagggag cttccagggg gaaacgcctg gtatctttat agtcctgtcg ggtttcgcca    5280
cctctgactt gagcgtcgat ttttgtgatg ctcgtcaggg gggcggagcc tatggaaaaa    5340
cgccagcaac gcggcctttt tacggttcct ggccttttgc tggccttttg ctcacatgtt    5400
ctttcctgcg ttatcccctg attctgtgga taaccgtatt accgccatgc at          5452
```

<210> SEQ ID NO 10
<211> LENGTH: 5452
<212> TYPE: DNA
<213> ORGANISM: Artificial Sequence
<220> FEATURE:
<223> OTHER INFORMATION: Vector pCYdL9.5eGFP

<400> SEQUENCE: 10

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
```

```
ggactttcca aaatgtcgta caaactccgc cccattgacg caaatgggcg gtaggcgtgt    540
acggtgggag gtctatataa gcagagctgg tttagtgaac cgtcagatcc gctagcgcta    600
ccggtcgcca ccatggcctc ttacgaatta acacaacctc catctgtttc tgtttctcca    660
ggtcaaactg ctagaattac ttgttctggt gatgctttgc caaacaata cacttactgg     720 tatcaacaaa aagctggtca agctccagtt ttggttattt ataaagatac tgaaagacca    780
tctggtattc cagaaagatt ctcaggtact tcttctggta ctactgctac tttgactatt    840
tctggtgttc aagctgaaga tgaagctgat tattattgtc aatctgctga ttcttctggt    900
tctcatgtat ttttcggtgg tggtactaaa gttactgttt tgtctggtgg aggaggccca    960
ggtggcggtt caggtggagg ttctggcgga ggttctggtg gaggttccta tgagttgact   1020
cagccaccct cggtgtcagt gtccccagga cagacggcca ggatcacctg ctctggagat   1080
gcattgccaa agcaatatac ttattggtac cagcagaagg caggccaggc ccctgtcttg   1140
gtgatatata aagacactga gaggccctca gggatccctg agcgattctc tggtaccagt   1200
tcagggacaa cagccacatt gaccatcagt ggagtccagg cagaagacga ggctgactat   1260
tactgtcaat cagcagacag cagtggttcc cacgttttct cggcggagg gaccaaggtg    1320 accgtactat ccggagggcg cgcctctggt ggcggagctt ctggaggtgg ttctggcggc   1380
tctggtatgg tgagcaaggg cgaggagctg ttcaccgggg tggtgcccat cctggtcgag   1440
ctggacggcg acgtaaacgg ccacaagttc agcgtgtccg gcgagggcga gggcgatgcc   1500
acctacggca agctgaccct gaagttcatc tgcaccaccg gcaagctgcc cgtgccctgg   1560
cccaccctcg tgaccaccct gacctacggc gtgcagtgct tcagccgcta ccccgaccac   1620
atgaagcagc acgacttctt caagtccgcc atgcccgaag gctacgtcca ggagcgcacc   1680
atcttcttca aggacgacgg caactacaag acccgcgccg aggtgaagtt cgagggcgac   1740
accctggtga accgcatcga gctgaagggc atcgacttca aggaggacgg caacatcctg   1800
gggcacaagc tggagtacaa ctacaacagc cacaacgtct atatcatggc cgacaagcag   1860
aagaacggca tcaaggtgaa cttcaagatc cgccacaaca tcgaggacgg cagcgtgcag   1920
ctcgccgacc actaccagca gaacacccc atcggcgacg gccccgtgct gctgcccgac   1980
aaccactacc tgagcaccca gtccgccctg agcaaagacc ccaacgagaa gcgcgatcac   2040
atggtcctgc tggagttcgt gaccgccgcc gggatcactc tcggcatgga cgagctgtac   2100
aagtaacccg ggatccaccg gatctagata actgatcata atcagccata ccacatttgt   2160
agaggtttta cttgctttaa aaaacctccc acacctcccc ctgaacctga acataaaat    2220 gaatgcaatt gttgttgtta acttgtttat tgcagcttat aatggttaca aataaagcaa   2280
tagcatcaca aatttcacaa ataaagcatt ttttcactg cattctagtt gtggtttgtc    2340
caaactcatc aatgtatctt aacgcgtaaa ttgtaagcgt taatattttg ttaaaattcg   2400
cgttaaattt ttgttaaatc agctcatttt ttaaccaata ggccgaaatc ggcaaaatcc   2460
cttataaatc aaaagaatag accgagatag ggttgagtgt tgttccagtt tggaacaaga   2520
gtccactatt aaagaacgtg gactccaacg tcaagggcg aaaaccgtc tatcagggcg     2580 atggcccact acgtgaacca tcaccctaat caagttttt ggggtcgagg tgccgtaaag    2640
cactaaatcg gaaccctaaa gggagccccc gatttagagc ttgacgggga agccggcga    2700 acgtggcgag aaaggaaggg aagaaagcga aaggagcggg cgctaggcg ctggcaagtg    2760 tagcggtcac gctgcgcgta accaccacac ccgccgcgct taatgcgccg ctacagggcg   2820
```

```
cgtcaggtgg cacttttcgg ggaaatgtgc gcggaacccc tatttgttta tttttctaaa   2880
tacattcaaa tatgtatccg ctcatgagac aataaccctg ataaatgctt caataatatt   2940
gaaaaaggaa gagtcctgag gcggaaagaa ccagctgtgg aatgtgtgtc agttagggtg   3000
tggaaagtcc ccaggctccc cagcaggcag aagtatgcaa agcatgcatc tcaattagtc   3060
agcaaccagg tgtggaaagt ccccaggctc cccagcaggc agaagtatgc aaagcatgca   3120
tctcaattag tcagcaacca tagtcccgcc cctaactccg cccatcccgc cctaactcc    3180 gcccagttcc gcccattctc cgccccatgg ctgactaatt ttttttattt atgcagaggc   3240
cgaggccgcc tcggcctctg agctattcca gaagtagtga ggaggctttt ttggaggcct   3300
aggcttttgc aaagatcgat caagagacag gatgaggatc gtttcgcatg attgaacaag   3360
atggattgca cgcaggttct ccggccgctt gggtggagag gctattcggc tatgactggg   3420
cacaacagac aatcggctgc tctgatgccg ccgtgttccg gctgtcagcg caggggcgcc   3480
cggttctttt tgtcaagacc gacctgtccg gtgccctgaa tgaactgcaa gacgaggcag   3540
cgcggctatc gtggctggcc acgacgggcg ttccttgcgc agctgtgctc gacgttgtca   3600
ctgaagcggg aagggactgg ctgctattgg gcgaagtgcc ggggcaggat ctcctgtcat   3660
ctcaccttgc tcctgccgag aaagtatcca tcatggctga tgcaatgcgg cggctgcata   3720
cgcttgatcc ggctacctgc ccattcgacc accaagcgaa acatcgcatc gagcgagcac   3780
gtactcggat ggaagccggt cttgtcgatc aggatgatct ggacgaagag catcaggggc   3840
tcgcgccagc cgaactgttc gccaggctca aggcgagcat gcccgacggc gaggatctcg   3900
tcgtgaccca tggcgatgcc tgcttgccga atatcatggt ggaaaatggc cgcttttctg   3960
gattcatcga ctgtggccgg ctgggtgtgg cggaccgcta tcaggacata gcgttggcta   4020
cccgtgatat tgctgaagag cttggcggcg aatgggctga ccgcttcctc gtgctttacg   4080
gtatcgccgc tcccgattcg cagcgcatcg ccttctatcg ccttcttgac gagttcttct   4140
gagcgggact ctggggttcg aaatgaccga ccaagcgacg cccaacctgc catcacgaga   4200
tttcgattcc accgccgcct tctatgaaag gttgggcttc ggaatcgttt tccgggacgc   4260
cggctggatg atcctccagc gcggggatct catgctggag ttcttcgccc acctaggggg   4320
gaggctaact gaaacacgga aggagacaat accggaagga acccgcgcta tgacggcaat   4380
aaaaagacag aataaaacgc acggtgttgg gtcgtttgtt cataaacgcg gggttcggtc   4440
ccagggctgg cactctgtcg ataccccacc gagacccat tggggccaat acgcccgcgt    4500
ttcttccttt tccccacccc acccccaag ttcgggtgaa ggcccagggc tcgcagccaa    4560
cgtcggggcg gcaggccctg ccatagcctc aggttactca tatatacttt agattgattt   4620
aaaacttcat ttttaattta aaaggatcta ggtgaagatc cttttttgata atctcatgac   4680 caaaatccct taacgtgagt tttcgttcca ctgagcgtca gaccccgtag aaaagatcaa   4740
aggatcttct tgagatcctt ttttttctgcg cgtaatctgc tgcttgcaaa caaaaaaacc   4800
accgctacca gcggtggttt gtttgccgga tcaagagcta ccaactcttt ttccgaaggt   4860
aactggcttc agcagagcgc agataccaaa tactgtcctt ctagtgtagc cgtagttagg   4920
ccaccacttc aagaactctg tagcaccgcc tacatacctc gctctgctaa tcctgttacc   4980
agtggctgct gccagtggcg ataagtcgtg tcttaccggg ttggactcaa gacgatagtt   5040
accggataag gcgcagcggt cgggctgaac ggggggttcg tgcacacagc ccagcttgga   5100
gcgaacgacc tacaccgaac tgagatacct acagcgtgag ctatgagaaa gcgccacgct   5160
tcccgaaggg agaaaggcgg acaggtatcc ggtaagcggc agggtcggaa caggagagcg   5220
```

```
cacgagggag cttccagggg gaaacgcctg gtatctttat agtcctgtcg ggtttcgcca    5280
cctctgactt gagcgtcgat ttttgtgatg ctcgtcaggg gggcggagcc tatggaaaaa    5340
cgccagcaac gcggcctttt tacggttcct ggcctttttgc tggcctttttg ctcacatgtt    5400 cttttcctgcg ttatcccctg attctgtgga taaccgtatt accgccatgc at            5452
```

<210> SEQ ID NO 11
<211> LENGTH: 5527
<212> TYPE: DNA
<213> ORGANISM: Artificial Sequence
<220> FEATURE:
<223> OTHER INFORMATION: Vector pMTdL9.5eGFP

<400> SEQUENCE: 11

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta caactccgcc ccattgacg caaatgggcg gtaggcgtgt     540
acggtgggag gtctatataa gcagagctgg tttagtgaac cgtcagatcc gctagcgcta     600
ccggtcgcca ccatgctcgc tacaagagtt ttctcacttg tcggcaaaag agccatttct     660
acctcggttt gtgtaagggc tgaagaatct agaagctacg aactgacaca acctccatct     720
gtttctgttt ctccaggtca aactgctaga attacttgtt ctggtgatgc tttgccaaaa     780
caatacactt actggtatca acaaaaagct ggtcaagctc cagttttggt tatttataaa     840
gatactgaaa gaccatctgg tattccagaa agattctcag gtacttcttc tggtactact     900
gctactttga ctatttctgg tgttcaagct gaagatgaag ctgattatta ttgtcaatct     960
gctgattctt ctggttctca tgtatttttc ggtggtggta ctaaagttac tgttttgtct    1020
ggtggaggag gccaggtgg cggttcaggt ggaggttctg gcggaggttc tggtggaggt    1080
tcctatgagt tgactcagcc acctcggtg tcagtgtccc aggacagac ggccaggatc     1140 acctgctctg gagatgcatt gccaaagcaa tatacttatt ggtaccagca gaaggcaggc    1200
caggcccctg tcttggtgat atataaagac actgagaggc cctcagggat ccctgagcga    1260
ttctctggta ccagttcagg gacaacagcc acattgacca tcagtggagt ccaggcagaa    1320
gacgaggctg actattactg tcaatcagca gacagcagtg gttcccacgt tttcttcggc    1380
ggagggacca aggtgaccgt actatccgga gggcgcgcct ctggtggcgg agcttctgga    1440
ggtggttctg gcggctctgg tatggtgagc aagggcgagg agctgttcac cggggtggtg    1500
cccatcctgg tcgagctgga cggcgacgta aacggccaca agttcagcgt gtccggcgag    1560
ggcgagggcg atgccaccta cggcaagctg accctgaagt tcatctgcac caccggcaag    1620
ctgcccgtgc cctggcccac cctcgtgacc accctgacct acggcgtgca gtgcttcagc    1680
cgctaccccg accacatgaa gcagcacgac ttcttcaagt ccgccatgcc cgaaggctac    1740
gtccaggagc gcaccatctt cttcaaggac gacggcaact acaagacccg cgccgaggtg    1800
```

```
aagttcgagg gcgacaccct ggtgaaccgc atcgagctga agggcatcga cttcaaggag    1860
gacggcaaca tcctgggca caagctggag tacaactaca acagccacaa cgtctatatc     1920
atggccgaca agcagaagaa cggcatcaag gtgaacttca agatccgcca caacatcgag    1980
gacggcagcg tgcagctcgc cgaccactac cagcagaaca cccccatcgg cgacggcccc    2040
gtgctgctgc ccgacaacca ctacctgagc acccagtccg ccctgagcaa agaccccaac    2100
gagaagcgcg atcacatggt cctgctggag ttcgtgaccg ccgccgggat cactctcggc    2160
atggacgagc tgtacaagta acccgggatc caccggatct agataactga tcataatcag    2220
ccataccaca tttgtagagg ttttacttgc tttaaaaaac ctcccacacc tccccctgaa    2280
cctgaaacat aaaatgaatg caattgttgt tgttaacttg tttattgcag cttataatgg    2340
ttacaaataa agcaatagca tcacaaattt cacaaataaa gcattttttt cactgcattc    2400
tagttgtggt ttgtccaaac tcatcaatgt atcttaacgc gtaaattgta agcgttaata    2460
ttttgttaaa attcgcgtta aattttttgtt aaatcagctc attttttaac caataggccg    2520
aaatcggcaa aatcccttat aaatcaaaag aatagaccga gatagggttg agtgttgttc    2580
cagtttggaa caagagtcca ctattaaaga acgtggactc caacgtcaaa gggcgaaaaa    2640
ccgtctatca gggcgatggc ccactacgtg aaccatcacc ctaatcaagt tttttggggt    2700
cgaggtgccg taaagcacta atcggaacc ctaagggag ccccgattt agagcttgac    2760 ggggaaagcc ggcgaacgtg gcgagaaagg aagggaagaa agcgaaagga gcgggcgcta    2820
gggcgctggc aagtgtagcg gtcacgctgc gcgtaaccac cacacccgcc gcgcttaatg    2880
cgccgctaca gggcgcgtca ggtggcactt tcggggaaa tgtgcgcgga acccctattt    2940 gtttatttt ctaaatacat tcaaatatgt atccgctcat gagacaataa ccctgataaa    3000
tgcttcaata atattgaaaa aggaagagtc ctgaggcgga aagaaccagc tgtggaatgt    3060
gtgtcagtta gggtgtggaa agtccccagg ctccccagca ggcagaagta tgcaaagcat    3120
gcatctcaat tagtcagcaa ccaggtgtgg aaagtcccca ggctccccag caggcagaag    3180
tatgcaaagc atgcatctca attagtcagc aaccatagtc cgcccctaa ctccgcccat    3240 cccgccccta actccgccca gttccgccca ttctccgccc catggctgac taatttttttt    3300 tatttatgca gaggccgagg ccgcctcggc ctctgagcta ttccagaagt agtgaggagg    3360
cttttttgga ggcctaggct tttgcaaaga tcgatcaaga acaggatga ggatcgtttc    3420 gcatgattga acaagatgga ttgcacgcag gttctccggc cgcttgggtg agaggctat    3480 tcggctatga ctgggcacaa cagacaatcg gctgctctga tgccgccgtg ttccggctgt    3540
cagcgcaggg gcgcccggtt ctttttgtca agaccgacct gtccggtgcc ctgaatgaac    3600
tgcaagacga ggcagcgcgg ctatcgtggc tggccacgac gggcgttcct tgcgcagctg    3660
tgctcgacgt tgtcactgaa gcgggaaggg actggctgct attgggcgaa gtgccggggc    3720
aggatctcct gtcatctcac cttgctcctg ccgagaaagt atccatcatg gctgatgcaa    3780
tgcggcggct gcatacgctt gatccggcta cctgcccatt cgaccaccaa gcgaaacatc    3840
gcatcgagcg agcacgtact cggatggaag ccggtcttgt cgatcaggat gatctggacg    3900
aagagcatca ggggctcgcg ccagccgaac tgttcgccag gctcaaggcg agcatgcccg    3960
acggcgagga tctcgtcgtg acccatggcg atgcctgctt gccgaatatc atggtggaaa    4020
atggccgctt ttctggattc atcgactgtg gccggctggg tgtggcggac cgctatcagg    4080
acatagcgtt ggctacccgt gatattgctg aagagcttgg cggcgaatgg gctgaccgct    4140
tcctcgtgct ttacggtatc gccgctcccg attcgcagcg catcgccttc tatcgccttc    4200
```

```
ttgacgagtt cttctgagcg ggactctggg gttcgaaatg accgaccaag cgacgcccaa    4260
cctgccatca cgagatttcg attccaccgc cgccttctat gaaaggttgg gcttcggaat    4320
cgttttccgg gacgccggct ggatgatcct ccagcgcggg gatctcatgc tggagttctt    4380
cgcccaccct aggggaggc taactgaaac acggaaggag acaataccgg aaggaacccg    4440
cgctatgacg gcaataaaaa gacagaataa aacgcacggt gttgggtcgt ttgttcataa    4500
acgcggggtt cggtcccagg gctggcactc tgtcgatacc ccaccgagac cccattgggg    4560
ccaatacgcc cgcgtttctt ccttttcccc accccacccc caagttcgg gtgaaggccc    4620
agggctcgca gccaacgtcg gggcggcagg ccctgccata gcctcaggtt actcatatat    4680
actttagatt gatttaaaac ttcattttta atttaaaagg atctaggtga agatccttt    4740
tgataatctc atgaccaaaa tcccttaacg tgagttttcg ttccactgag cgtcagaccc    4800
cgtagaaaag atcaaaggat cttcttgaga tcctttttttt ctgcgcgtaa tctgctgctt    4860
gcaaacaaaa aaaccaccgc taccagcggt ggtttgtttg ccggatcaag agctaccaac    4920
tcttttccg aaggtaactg gcttcagcag agcgcagata ccaaatactg tccttctagt    4980
gtagccgtag ttaggccacc acttcaagaa ctctgtagca ccgcctacat acctcgctct    5040
gctaatcctg ttaccagtgg ctgctgccag tggcgataag tcgtgtctta ccgggttgga    5100
ctcaagacga tagttaccgg ataaggcgca gcggtcgggc tgaacggggg gttcgtgcac    5160
acagcccagc ttggagcgaa cgacctacac cgaactgaga tacctacagc gtgagctatg    5220
agaaagcgcc acgcttcccg aagggagaaa ggcggacagg tatccggtaa gcggcagggt    5280
cggaacagga gagcgcacga gggagcttcc agggggaaac gcctggtatc tttatagtcc    5340
tgtcgggttt cgccacctct gacttgagcg tcgatttttg tgatgctcgt caggggggcg    5400
gagcctatgg aaaaacgcca gcaacgcggc ctttttacgg ttcctggcct tttgctggcc    5460
ttttgctcac atgttctttc ctgcgttatc ccctgattct gtggataacc gtattaccgc    5520
catgcat                                                              5527
```

<210> SEQ ID NO 12
<211> LENGTH: 10947
<212> TYPE: DNA
<213> ORGANISM: Artificial Sequence
<220> FEATURE:
<223> OTHER INFORMATION: Bi-cistronic lentiviral vector

<400> SEQUENCE: 12

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360
accccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
```

```
ttgactcacg gggatttcca agtctccacc ccattgacgt caatgggagt ttgttttggc      720
accaaaatca acgggacttt ccaaaatgtc gtaacaactc cgccccattg acgcaaatgg      780
gcggtaggcg tgtacggtgg gaggtctata taagcagcgc gttttgcctg tactgggtct      840
ctctggttag accagatctg agcctgggag ctctctggct aactagggaa cccactgctt      900
aagcctcaat aaagcttgcc ttgagtgctt caagtagtgt gtgcccgtct gttgtgtgac      960
tctggtaact agagatccct cagaccctt tagtcagtgt ggaaaatctc tagcagtggc     1020
gcccgaacag ggacttgaaa gcgaaaggga accagagga gctctctcga cgcaggactc     1080
ggcttgctga agcgcgcacg gcaagaggcg aggggcggcg actggtgagt acgccaaaaa     1140
ttttgactag cggaggctag aaggagagag atgggtgcga gagcgtcagt attaagcggg     1200
ggagaattag atcgcgatgg gaaaaaattc ggttaaggcc agggggaaag aaaaaatata     1260
aattaaaaca tatagtatgg gcaagcaggg agctagaacg attcgcagtt aatcctggcc     1320
tgttagaaac atcagaaggc tgtagacaaa tactgggaca gctacaacca tcccttcaga     1380
caggatcaga agaacttaga tcattatata atacagtagc aaccctctat tgtgtgcatc     1440
aaaggataga gataaaagac accaaggaag ctttagacaa gatagaggaa gagcaaaaca     1500
aaagtaagac caccgcacag caagcggccg ctgatcttca gacctggagg aggagatatg     1560
agggacaatt ggagaagtga attatataaa tataaagtag taaaaattga accattagga     1620
gtagcaccca ccaaggcaaa gagaagagtg gtgcagagag aaaaaagagc agtgggaata     1680
ggagctttgt tccttgggtt cttgggagca gcaggaagca ctatgggcgc agcgtcaatg     1740
acgctgacgg tacaggccag acaattattg tctggtatag tgcagcagca gaacaatttg     1800
ctgagggcta ttgaggcgca acagcatctg ttgcaactca cagtctgggg catcaagcag     1860
ctccaggcaa gaatcctggc tgtggaaaga tacctaaagg atcaacagct cctgggcatt     1920
tggggttgct ctggaaaact catttgcacc actgctgtgc cttggaatgc tagttggagt     1980
aataaatctc tggaacagat ttggaatcac acgacctgga tggagtggga cagagaaatt     2040
aacaattaca caagcttaat acactcctta attgaagaat cgcaaaacca gcaagaaaag     2100
aatgaacaag aattattgga attagataaa tgggcaagtt tgtggaattg gtttaacata     2160
acaaattggc tgtggtatat aaaattattc ataatgatag taggaggctt ggtaggttta     2220
agaatagttt ttgctgtact ttctatagtg aatagagtta ggcagggata ttcaccatta     2280
tcgtttcaga cccacctccc aaccccgagg ggacccgaca ggcccgaagg aatagaagaa     2340
gaaggtggag agagacag agacagatcc attcgattag tgaacggatc ggcactgcgt     2400
gcgccaattc tgcagacaaa tggcagtatt catccacaat tttaaaagaa aagggggggat     2460 tggggggtac agtgcagggg aaagaatagt agacataata gcaacagaca tacaaactaa     2520
agaattacaa aaacaaatta caaaaattca aaattttcgg gtttattaca gggacagcag     2580
agatccagtt tggttaatta atagttatta atagtaatca attacggggt cattagttca     2640
tagcccatat atggagttcc gcgttacata acttacggta aatggcccgc ctggctgacc     2700
gcccaacgac ccccgcccat tgacgtcaat aatgacgtat gttcccatag taacgccaat     2760
agggactttc cattgacgtc aatgggtgga gtatttacgg taaactgccc acttggcagt     2820
acatcaagtg tatcatatgc caagtacgcc ccctattgac gtcaatgacg gtaaatggcc     2880
cgcctggcat tatgcccagt acatgacctt atgggacttt cctacttggc agtacatcta     2940
cgtattagtc atcgctatta ccatggtgat gcggttttgg cagtacatca atgggcgtgg     3000
atagcggttt gactcacggg gatttccaag tctccacccc attgacgtca atgggagttt     3060
```

```
gttttggcac caaaatcaac gggactttcc aaaatgtcgt aacaactccg ccccattgac   3120
gcaaatgggc ggtaggcgtg tacggtggga ggtctatata agcagagctg gtttagtgaa   3180
ccgtcagatc cgctagcgct accggtcgcc accatggaga cagacacact cctgctatgg   3240
gtactgctgc tctgggttcc aggttccact ggtgactatc catatgatgt tccagattat   3300
gcttctagct cttacgaatt aacacaacct ccatctgttt ctgtttctcc aggtcaaact   3360
gctagaatta cttgttctgg tgatgctttg ccaaaacaat acacttactg gtatcaacaa   3420
aaagctggtc aagctccagt tttggttatt tataaagata ctgaaagacc atctggtatt   3480
ccagaaagat tctcaggtac ttcttctggt actactgcta cttttgactat ttctggtgtt   3540 caagctgaag atgaagctga ttattattgt caatctgctg attcttctgg ttcttatgta   3600
tttttcggtg gtggtactaa agttactgtt ttgtctggtg gaggaggccc aggtggcggt   3660
tcaggtggag gttctggcgg aggttctggt ggaggttcct atgagttgac tcagccaccc   3720
tcggtgtcag tgtccccagg acagacggcc aggatcacct gctctggaga tgcattgcca   3780
aagcaatata cttattggta ccagcagaag gcaggccagg cccctgtctt ggtgatatat   3840
aaagacactg agaggccctc agggatccct gagcgattct ctggtaccag ttcagggaca   3900
acagtcacat tgaccatcag tggagtccag gcagaagacg aggctgacta ttactgtcaa   3960
tcagcagaca gcagtggttc ctatgttttc ttcggcggag ggaccaaggt gaccgtacta   4020
tccggaggcg gtgggaagaa gttcccccca gaagaccctc ctgatagcaa gaacacactt   4080
gtgctctttg gggcaggatt cggcgcagta ataacagtcg tcgtcatcgt tgtcatcatc   4140
aaatgcttct gtaagcacag aagctgtttc agaagaaatg aggcaagcag agaaacaaac   4200
aacagcctta ccttcgggcc tgaagaagca ttagctgaac agaccgtctt cctttgtaca   4260
tagtaatgaa cggatccgta attccgcccc tctccctccc ccccccctaa cgttactggc   4320
cgaagccgct tggaataagg ccggtgtgcg tttgtctata tgttattttc caccatattg   4380
ccgtcttttg gcaatgtgag ggcccggaaa cctggccctg tcttcttgac gagcattcct   4440
aggggtcttt cccctctcgc caaaggaatg caaggtctgt tgaatgtcgt gaaggaagca   4500
gttcctctgg aagcttcttg aagacaaaca acgtctgtag cgaccctttg caggcagcgg   4560
aaccccccac ctggcgacag gtgcctctgc ggccaaaagc cacgtgtata agatacacct   4620
gcaaaggcgg cacaacccca gtgccacgtt gtgagttgga tagttgtgga aagagtcaaa   4680
tggctctcct caagcgtatt caacaagggg ctgaaggatg cccagaaggt accccattgt   4740
atgggatctg atctggggcc tcggtgcaca tgctttacat gtgtttagtc gaggttaaaa   4800
aacgtctagg ccccccgaac cacggggacg tggttttcct ttgaaaaaca cgatgataag   4860
cttgccacaa cccacaagga gacggcgcgc catggtgagc aagggcgagg agctgttcac   4920
cggggtggtg cccatcctgg tcgagctgga cggcgacgta aacggccaca agttcagcgt   4980
gtccggcgag ggcgagggcg atgccaccta cggcaagctg accctgaagt tcatctgcac   5040
caccggcaag ctgcccgtgc cctggcccac cctcgtgacc accctgacct acggcgtgca   5100
gtgcttcagc cgctaccccg accacatgaa gcagcacgac ttcttcaagt ccgccatgcc   5160
cgaaggctac gtccaggagc gcaccatctt cttcaaggac gacggcaact acaagacccg   5220
cgccgaggtg aagttcgagg gcgacaccct ggtgaaccgc atcgagctga agggcatcga   5280
cttcaaggag gacggcaaca tcctggggca caagctggag tacaactaca acagccacaa   5340
cgtctatatc atggccgaca agcagaagaa cggcatcaag gtgaacttca agatccgcca   5400
```

```
caacatcgag gacggcagcg tgcagctcgc cgaccactac cagcagaaca cccccatcgg    5460
cgacggcccc gtgctgctgc ccgacaacca ctacctgagc acccagtccg ccctgagcaa    5520 agacccaac gagaagcgcg atcacatggt cctgctggag ttcgtgaccg ccgccgggat    5580
cactctcggc atggacgagc tgtataagta ataggaattc gatatcaagc ttatcgataa    5640
tcaacctctg gattacaaaa tttgtgaaag attgactggt attcttaact atgttgctcc    5700
ttttacgcta tgtggatacg ctgctttaat gcctttgtat catgctattg cttcccgtat    5760
ggctttcatt ttctcctcct tgtataaatc ctggttgctg tctctttatg aggagttgtg    5820
gcccgttgtc aggcaacgtg gcgtggtgtg cactgtgttt gctgacgcaa ccccactgg    5880 ttggggcatt gccaccacct gtcagctcct ttccgggact ttcgctttcc cctccctat    5940 tgccacggcg gaactcatcg ccgcctgcct tgcccgctgc tggacagggg ctcggctgtt    6000
gggcactgac aattccgtgg tgttgtcggg gaaatcatcg tccttttcctt ggctgctcgc    6060 ctgtgttgcc acctggattc tgcgcgggac gtccttctgc tacgtccctt cggccctcaa    6120
tccagcggac cttccttccc gcggcctgct gccggctctg cggcctcttc cgcgtcttcg    6180
ccttcgccct cagacgagtc ggatctccct ttgggccgcc tccccgcatc gataccgtcg    6240
acctcgagac ctagaaaaac atggagcaat cacaagtagc aatacagcag ctaccaatgc    6300
tgattgtgcc tggctagaag cacaagagga ggaggaggtg ggttttccag tcacacctca    6360 ggtacctta agaccaatga cttacaaggc agctgtagat cttagccact ttttaaaaga    6420 aaaggggga ctggaagggc taattcactc ccaacgaaga caagatatcc ttgatctgtg    6480
gatctaccac acacaaggct acttccctga ttggcagaac tacacaccag gccagggat    6540 cagatatcca ctgacctttg gatggtgcta caagctagta ccagttgagc aagagaaggt    6600
agaagaagcc aatgaaggag agaacacccg cttgttacac cctgtgagcc tgcatgggat    6660
ggatgacccg gagagagaag tattagagtg gaggtttgac agccgcctag catttcatca    6720
catggcccga gagctgcatc cggactgtac tgggtctctc tggttagacc agatctgagc    6780
ctgggagctc tctggctaac tagggaaccc actgcttaag cctcaataaa gcttgccttg    6840
agtgcttcaa gtagtgtgtg cccgtctgtt gtgtgactct ggtaactaga gatccctcag    6900 accctttta tcagtgtgga aaatctctag caggccccgt ttaaaccgc tgatcagcct    6960 cgactgtgcc ttctagttgc cagccatctg ttgtttgccc ctccccgtg ccttccttga    7020 ccctggaagg tgccactccc actgtccttt cctaataaaa tgaggaaatt gcatcgcatt    7080
gtctgagtag tgtcattct attctggggg gtgggtggg gcaggacagc aaggggagg    7140 attgggaaga caatagcagg catgctgggg atgcggtggg ctctatggct tctgaggcgg    7200
aaagaaccag ctggggctct agggggtatc cccacgcgcc ctgtagcggc gcattaagcg    7260
cggcgggtgt ggtggttacg cgcagcgtga ccgctacact tgccagcgcc ctagcgcccg    7320
ctcctttcgc tttcttccct tcctttctcg ccacgttcgc cggctttccc cgtcaagctc    7380
taaatcgggg gctcccttta gggttccgat ttagtgcttt acggcacctc gacccaaaa    7440 aacttgatta gggtgatggt tcacgtagtg gccatcgccc tgatagacg gtttttcgcc    7500 ctttgacgtt ggagtccacg ttctttaata gtggactctt gttccaaact ggaacaacac    7560
tcaaccctat ctcggtctat tcttttgatt tataagggat tttgccgatt tcggcctatt    7620
ggttaaaaaa tgagctgatt taacaaaaat ttaacgcgaa ttaattctgt ggaatgtgtg    7680
tcagttaggg tgtggaaagt ccccaggctc cccagcaggc agaagtatgc aaagcatgca    7740
tctcaattag tcagcaacca ggtgtggaaa gtccccaggc tccccagcag gcagaagtat    7800
```

```
gcaaagcatg catctcaatt agtcagcaac catagtcccg cccctaactc cgcccatccc    7860
gcccctaact ccgcccagtt ccgcccattc tccgccccat ggctgactaa ttttttttat    7920
ttatgcagag gccgaggccg cctctgcctc tgagctattc cagaagtagt gaggaggctt    7980
ttttggaggc ctaggctttt gcaaaaagct cccgggagct tgtatatcca ttttcggatc    8040
tgatcagcac gtgttgacaa ttaatcatcg gcatagtata tcggcatagt ataatacgac    8100
aaggtgagga actaaaccat ggccaagttg accagtgccg ttccggtgct caccgcgcgc    8160
gacgtcgccg gagcggtcga gttctggacc gaccggctcg ggttctcccg ggacttcgtg    8220
gaggacgact tcgccggtgt ggtccgggac gacgtgaccc tgttcatcag cgcggtccag    8280
gaccaggtgg tgccggacaa caccctggcc tgggtgtggg tgcgcggcct ggacgagctg    8340
tacgccgagt ggtcggaggt cgtgtccacg aacttccggg acgcctccgg gccggccatg    8400
accgagatcg gcgagcagcc gtgggggcgg gagttcgccc tgcgcgaccc ggccggcaac    8460
tgcgtgcact tcgtggccga ggagcaggac tgacacgtgc tacgagattt cgattccacc    8520
gccgccttct atgaaaggtt gggcttcgga atcgttttcc gggacgccgg ctggatgatc    8580
ctccagcgcg gggatctcat gctggagttc ttcgcccacc ccaacttgtt tattgcagct    8640
tataatggtt acaaataaag caatagcatc acaaatttca caaataaagc attttttcca    8700
ctgcattcta gttgtggttt gtccaaactc atcaatgtat cttatcatgt ctgtataccg    8760
tcgacctcta gctagagctt ggcgtaatca tggtcatagc tgtttcctgt gtgaaattgt    8820
tatccgctca caattccaca acatacga gccggaagca taagtgtaa agcctggggt    8880 gcctaatgag tgagctaact cacattaatt gcgttgcgct cactgcccgc tttccagtcg    8940
ggaaacctgt cgtgccagct gcattaatga atcggccaac gcgcggggag aggcggtttg    9000
cgtattgggc gctcttccgc ttcctcgctc actgactcgc tgcgctcggt cgttcggctg    9060
cggcgagcgg tatcagctca ctcaaaggcg gtaatacggt tatccacaga atcaggggat    9120
aacgcaggaa agaacatgtg agcaaaaggc cagcaaaagg ccaggaaccg taaaaaggcc    9180
gcgttgctgg cgttttttcca taggctccgc cccctgacg agcatcacaa aaatcgacgc    9240
tcaagtcaga ggtggcgaaa cccgacagga ctataaagat accaggcgtt ccccctgga    9300 agctccctcg tgcgctctcc tgttccgacc ctgccgctta ccggatacct gtccgccttt    9360
ctcccttcgg aagcgtggc gctttctcat agctcacgct gtaggtatct cagttcggtg    9420
taggtcgttc gctccaagct gggctgtgtg cacgaacccc ccgttcagcc cgaccgctgc    9480
gccttatccg gtaactatcg tcttgagtcc aacccggtaa gacacgactt atcgccactg    9540
gcagcagcca ctggtaacag gattagcaga gcgaggtatg taggcggtgc tacagagttc    9600
ttgaagtggt ggcctaacta cggctacact agaagaacag tatttggtat ctgcgctctg    9660
ctgaagccag ttaccttcgg aaaaagagtt ggtagctctt gatccggcaa acaaaccacc    9720
gctggtagcg gtggtttttt tgtttgcaag cagcagatta cgcgcagaaa aaaggatct    9780 caagaagatc ctttgatctt ttctacgggg tctgacgctc agtggaacga aaactcacgt    9840
taagggattt tggtcatgag attatcaaaa aggatcttca cctagatcct tttaaattaa    9900
aaatgaagtt ttaaatcaat ctaaagtata tatgagtaaa cttggtctga cagttaccaa    9960
tgcttaatca gtgaggcacc tatctcagcg atctgtctat ttcgttcatc catagttgcc   10020
tgactccccg tcgtgtagat aactacgata cgggagggct taccatctgg ccccagtgct   10080
gcaatgatac cgcgagaccc acgctcaccg gctccagatt tatcagcaat aaaccagcca   10140
```

```
gccggaaggg ccgagcgcag aagtggtcct gcaactttat ccgcctccat ccagtctatt   10200
aattgttgcc gggaagctag agtaagtagt tcgccagtta atagtttgcg caacgttgtt   10260
gccattgcta caggcatcgt ggtgtcacgc tcgtcgtttg gtatggcttc attcagctcc   10320
ggttcccaac gatcaaggcg agttacatga tcccccatgt tgtgcaaaaa agcggttagc   10380
tccttcggtc ctccgatcgt tgtcagaagt aagttggccg cagtgttatc actcatggtt   10440
atggcagcac tgcataattc tcttactgtc atgccatccg taagatgctt ttctgtgact   10500
ggtgagtact caaccaagtc attctgagaa tagtgtatgc ggcgaccgag ttgctcttgc   10560
ccggcgtcaa tacgggataa taccgcgcca catagcagaa ctttaaaagt gctcatcatt   10620
ggaaaacgtt cttcggggcg aaaactctca aggatcttac cgctgttgag atccagttcg   10680
atgtaaccca ctcgtgcacc caactgatct tcagcatctt ttactttcac cagcgtttct   10740
gggtgagcaa aaacaggaag gcaaaatgcc gcaaaaaagg gaataagggc gacacggaaa   10800
tgttgaatac tcatactctt ccttttcaa tattattgaa gcatttatca gggttattgt   10860
ctcatgagcg gatacatatt tgaatgtatt tagaaaaata aacaaatagg ggttccgcgc   10920
acatttcccc gaaaagtgcc acctgac                                       10947
```

<210> SEQ ID NO 13
<211> LENGTH: 10947
<212> TYPE: DNA
<213> ORGANISM: Artificial Sequence
<220> FEATURE:
<223> OTHER INFORMATION: Bi-cistronic lentiviral vector

<400> SEQUENCE: 13

```
gtcgacggat cgggagatct cccgatcccc tatggtgcac tctcagtaca atctgctctg     60
atgccgcata gttaagccag tatctgctcc ctgcttgtgt gttggaggtc gctgagtagt    120
gcgcgagcaa aatttaagct acaacaaggc aaggcttgac cgacaattgc atgaagaatc    180
tgcttagggt taggcgtttt gcgctgcttc gcgatgtacg ggccagatat acgcgttgac    240
attgattatt gactagttat taatagtaat caattacggg gtcattagtt catagcccat    300
atatggagtt ccgcgttaca taacttacgg taaatggccc gcctggctga ccgcccaacg    360
acccccgccc attgacgtca ataatgacgt atgttcccat agtaacgcca atagggactt    420
tccattgacg tcaatgggtg gagtatttac ggtaaactgc ccacttggca gtacatcaag    480
tgtatcatat gccaagtacg ccccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga accagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
```

| | |
|---|---|
| aattaaaaca tatagtatgg gcaagcaggg agctagaacg attcgcagtt aatcctggcc | 1320 |
| tgttagaaac atcagaaggc tgtagacaaa tactgggaca gctacaacca tcccttcaga | 1380 |
| caggatcaga agaacttaga tcattatata atacagtagc aaccctctat tgtgtgcatc | 1440 |
| aaaggataga gataaaagac accaaggaag ctttagacaa gatagaggaa gagcaaaaca | 1500 |
| aaagtaagac caccgcacag caagcggccg ctgatcttca gacctggagg aggagatatg | 1560 |
| agggacaatt ggagaagtga attatataaa tataaagtag taaaaattga accattagga | 1620 |
| gtagcaccca ccaaggcaaa gagaagagtg gtgcagagag aaaaaagagc agtgggaata | 1680 |
| ggagctttgt tccttgggtt cttgggagca gcaggaagca ctatgggcgc agcgtcaatg | 1740 |
| acgctgacgg tacaggccag acaattattg tctggtatag tgcagcagca gaacaatttg | 1800 |
| ctgagggcta ttgaggcgca acagcatctg ttgcaactca cagtctgggg catcaagcag | 1860 |
| ctccaggcaa gaatcctggc tgtggaaaga tacctaaagg atcaacagct cctggggatt | 1920 |
| tggggttgct ctggaaaact catttgcacc actgctgtgc cttggaatgc tagttggagt | 1980 |
| aataaatctc tggaacagat ttggaatcac acgacctgga tggagtggga cagagaaatt | 2040 |
| aacaattaca caagcttaat acactcctta attgaagaat cgcaaaacca gcaagaaaag | 2100 |
| aatgaacaag aattattgga attagataaa tgggcaagtt tgtggaattg gtttaacata | 2160 |
| acaaattggc tgtggtatat aaaattattc ataatgatag taggaggctt ggtaggttta | 2220 |
| agaatagttt ttgctgtact ttctatagtg aatagagtta ggcagggata ttcaccatta | 2280 |
| tcgtttcaga cccacctccc aaccccgagg ggacccgaca ggcccgaagg aatagaagaa | 2340 |
| gaaggtggag agagagacag agacagatcc attcgattag tgaacggatc ggcactgcgt | 2400 |
| gcgccaattc tgcagacaaa tggcagtatt catccacaat tttaaaagaa aaggggggat | 2460 |
| tggggggtac agtgcagggg aaagaatagt agacataata gcaacagaca tacaaactaa | 2520 |
| agaattacaa aaacaaatta caaaaattca aaattttcgg gtttattaca gggacagcag | 2580 |
| agatccagtt tggttaatta atagttatta atagtaatca attacgggt cattagttca | 2640 |
| tagcccatat atggagttcc gcgttacata acttacggta aatggcccgc ctggctgacc | 2700 |
| gcccaacgac ccccgcccat tgacgtcaat aatgacgtat gttcccatag taacgccaat | 2760 |
| agggactttc cattgacgtc aatgggtgga gtatttacgg taaactgccc acttggcagt | 2820 |
| acatcaagtg tatcatatgc caagtacgcc ccctattgac gtcaatgacg gtaaatggcc | 2880 |
| cgcctggcat tatgcccagt acatgacctt atgggacttt cctacttggc agtacatcta | 2940 |
| cgtattagtc atcgctatta ccatggtgat gcggttttgg cagtacatca atgggcgtgg | 3000 |
| atagcggttt gactcacggg gatttccaag tctccacccc attgacgtca atgggagttt | 3060 |
| gttttggcac caaaatcaac gggactttcc aaaatgtcgt aacaactccg ccccattgac | 3120 |
| gcaaatgggc ggtaggcgtg tacggtggga ggtctatata agcagagctg gtttagtgaa | 3180 |
| ccgtcagatc cgctagcgct accggtcgcc accatggaga cagacacact cctgctatgg | 3240 |
| gtactgctgc tctgggttcc aggttccact ggtgactatc catatgatgt tccagattat | 3300 |
| gcttctagct cttacgaatt aacacaacct ccatctgttt ctgtttctcc aggtcaaact | 3360 |
| gctagaatta cttgttctgg tgatgctttg ccaaaacaat acacttactg gtatcaacaa | 3420 |
| aaagctggtc aagctccagt tttggttatt tataaagata ctgaaagacc atctggtatt | 3480 |
| ccagaaagat tctcaggtac ttcttctggt actactgcta ctttgactat ttctggtgtt | 3540 |
| caagctgaag atgaagctga ttattattgt caatctgctg attcttctgg ttctcatgta | 3600 |

```
ttttcggtg gtggtactaa agttactgtt ttgtctggtg gaggaggccc aggtggcggt    3660
tcaggtggag gttctggcgg aggttctggt ggaggttcct atgagttgac tcagccaccc    3720
tcggtgtcag tgtccccagg acagacggcc aggatcacct gctctggaga tgcattgcca    3780
aagcaatata cttattggta ccagcagaag gcaggccagg cccctgtctt ggtgatatat    3840
aaagacactg agaggccctc agggatccct gagcgattct ctggtaccag ttcagggaca    3900
acagccacat tgaccatcag tggagtccag gcagaagacg aggctgacta ttactgtcaa    3960
tcagcagaca gcagtggttc ccacgttttc ttcggcggag ggaccaaggt gaccgtacta    4020
tccgaggcg gtgggaagaa gttcccccca aagaccctc ctgatagcaa gaacacactt    4080
gtgctctttg gggcaggatt cggcgcagta ataacagtcg tcgtcatcgt tgtcatcatc    4140
aaatgcttct gtaagcacag aagctgtttc agaagaaatg aggcaagcag agaaacaaac    4200
aacagcctta ccttcgggcc tgaagaagca ttagctgaac agaccgtctt cctttgtaca    4260
tagtaatgaa cggatccgta attccgcccc tctccctccc ccccccctaa cgttactggc    4320
cgaagccgct tggaataagg ccggtgtgcg tttgtctata tgttattttc caccatattg    4380
ccgtcttttg gcaatgtgag ggcccggaaa cctggccctg tcttcttgac gagcattcct    4440
aggggtcttt cccctctcgc caaaggaatg caaggtctgt tgaatgtcgt gaaggaagca    4500
gttcctctgg aagcttcttg aagacaaaca acgtctgtag cgacccttg caggcagcgg    4560
aacccccac ctggcgacag tgcctctgc ggccaaaagc cacgtgtata agatacacct    4620
gcaaaggcgg cacaacccca gtgccacgtt gtgagttgga tagttgtgga aagagtcaaa    4680
tggctctcct caagcgtatt caacaagggg ctgaaggatg cccagaaggt accccattgt    4740
atgggatctg atctggggcc tcggtgcaca tgctttacat gtgtttagtc gaggttaaaa    4800
aacgtctagg ccccccgaac cacggggacg tggttttcct ttgaaaaaca cgatgataag    4860
cttgccacaa cccacaagga gacggcgcgc catggtgagc aagggcgagg agctgttcac    4920
cggggtggtg cccatcctgg tcgagctgga cggcgacgta aacggccaca gttcagcgt    4980
gtccggcgag ggcgagggcg atgccaccta cggcaagctg accctgaagt tcatctgcac    5040
caccggcaag ctgcccgtgc cctggcccac cctcgtgacc accctgacct acggcgtgca    5100
gtgcttcagc cgctaccccg accacatgaa gcagcacgac ttcttcaagt ccgccatgcc    5160
cgaaggctac gtccaggagc gcaccatctt cttcaaggac gacggcaact acaagacccg    5220
cgccgaggtg aagttcgagg gcgacaccct ggtgaaccgc atcgagctga agggcatcga    5280
cttcaaggag gacggcaaca tcctggggca caagctggag tacaactaca acagccacaa    5340
cgtctatatc atggccgaca agcagaagaa cggcatcaag gtgaacttca gatccgcca    5400
caacatcgag gacggcagcg tgcagctcgc cgaccactac cagcagaaca cccccatcgg    5460
cgacggcccc gtgctgctgc ccgacaacca ctacctgagc acccagtccg ccctgagcaa    5520
agaccccaac gagaagcgcg atcacatggt cctgctggag ttcgtgaccg ccgccgggat    5580
cactctcggc atggacgagc tgtataagta ataggaattc gatatcaagc ttatcgataa    5640
tcaacctctg gattacaaaa tttgtgaaag attgactggt attcttaact atgttgctcc    5700
ttttacgcta tgtggatacg ctgctttaat gcctttgtat catgctattg cttcccgtat    5760
ggctttcatt ttctcctcct tgtataaatc ctggttgctg tctctttatg aggagttgtg    5820
gcccgttgtc aggcaacgtg gcgtggtgtg cactgtgttt gctgacgcaa ccccccactgg    5880
ttggggcatt gccaccacct gtcagctcct tccgggact tcgctttcc ccctccctat    5940
tgccacggcg gaactcatcg ccgcctgcct tgcccgctgc tggacagggg ctcggctgtt    6000
```

```
gggcactgac aattccgtgg tgttgtcggg gaaatcatcg tcctttcctt ggctgctcgc    6060
ctgtgttgcc acctggattc tgcgcggggac gtccttctgc tacgtccctt cggccctcaa   6120
tccagcggac cttccttccc gcggcctgct gccggctctg cggcctcttc cgcgtcttcg    6180
ccttcgccct cagacgagtc ggatctccct ttgggccgcc tccccgcatc gataccgtcg    6240
acctcgagac ctagaaaaac atggagcaat acaagtagc aatacagcag ctaccaatgc     6300
tgattgtgcc tggctagaag cacaagagga ggaggaggtg ggttttccag tcacacctca    6360 ggtacccttta agaccaatga cttacaaggc agctgtagat cttagccact ttttaaaga   6420 aaagggggga ctgaagggc taattcactc ccaacgaaga caagatatcc ttgatctgtg     6480
gatctaccac acacaaggct acttccctga ttggcagaac tacacaccag gccagggat    6540 cagatatcca ctgacctttg gatggtgcta caagctagta ccagttgagc aagagaaggt    6600
agaagaagcc aatgaaggag agaacacccg cttgttacac cctgtgagcc tgcatgggat    6660
ggatgacccg gagagagaag tattagagtg gaggtttgac agccgcctag catttcatca    6720
catggcccga gagctgcatc cggactgtac tgggtctctc tggttagacc agatctgagc    6780
ctgggagctc tctggctaac tagggaaccc actgcttaag cctcaataaa gcttgccttg    6840
agtgcttcaa gtagtgtgtg cccgtctgtt gtgtgactct ggtaactaga gatccctcag    6900 accctttttag tcagtgtgga aaatctctag cagggcccgt ttaaacccgc tgatcagcct   6960
cgactgtgcc ttctagttgc cagccatctg ttgtttgccc ctcccccgtg ccttccttga    7020
ccctggaagg tgccactccc actgtccttt cctaataaaa tgaggaaatt gcatcgcatt    7080
gtctgagtag gtgtcattct attctggggg gtggggtggg gcaggacagc aaggggggagg   7140 attgggaaga caatagcagg catgctgggg atgcggtggg ctctatggct tctgaggcgg    7200
aaagaaccag ctgggctct aggggtatc cccacgcgcc ctgtagcggc gcattaagcg      7260
cggcgggtgt ggtggttacg cgcagcgtga ccgctacact tgccagcgcc ctagcgcccg    7320
ctcctttcgc tttcttccct ccttttctcg ccacgttcgc cggctttccc cgtcaagctc    7380
taaatcgggg gctcccttta gggttccgat ttagtgcttt acggcacctc gaccccaaaa    7440
aacttgatta gggtgatggt tcacgtagtg gccatcgcc ctgatagacg gttttcgcc      7500 ctttgacgtt ggagtccacg ttctttaata gtggactctt gttccaaact ggaacaacac    7560
tcaaccctat ctcggtctat tcttttgatt tataagggat tttgccgatt tcggcctatt    7620
ggttaaaaaa tgagctgatt taacaaaaat ttaacgcgaa ttaattctgt ggaatgtgtg    7680
tcagttaggg tgtggaaagt ccccaggctc cccagcaggc agaagtatgc aaagcatgca    7740
tctcaattag tcagcaacca ggtgtggaaa gtccccaggc tccccagcag gcagaagtat    7800
gcaaagcatg catctcaatt agtcagcaac catagtcccg cccctaactc cgcccatccc    7860
gcccctaact ccgcccagtt ccgcccattc tccgccccat ggctgactaa ttttttttat    7920
ttatgcagag gccgaggccg cctctgcctc tgagctattc cagaagtagt gaggaggctt    7980
ttttggaggc ctaggctttt gcaaaaagct cccgggagct gtatatcca ttttcggatc     8040 tgatcagcac gtgttgacaa ttaatcatcg gcatagtata tcggcatagt ataatacgac    8100
aaggtgagga actaaaccat ggccaagttg accagtgccg ttccggtgct caccgcgcgc    8160
gacgtcgccg gagcggtcga gttctggacc gaccggctcg ggttctcccg ggacttcgtg    8220
gaggacgact tcgccggtgt ggtccgggac gacgtgaccc tgttcatcag cgcggtccag    8280
gaccaggtgg tgccggacaa caccctggcc tgggtgtggg tgcgcggcct ggacgagctg    8340
```

```
tacgccgagt ggtcggaggt cgtgtccacg aacttccggg acgcctccgg gccggccatg    8400
accgagatcg gcgagcagcc gtggggggcgg gagttcgccc tgcgcgaccc ggccggcaac    8460
tgcgtgcact tcgtggccga ggagcaggac tgacacgtgc tacgagattt cgattccacc    8520
gccgccttct atgaaaggtt gggcttcgga atcgttttcc gggacgccgg ctggatgatc    8580
ctccagcgcg gggatctcat gctggagttc ttcgcccacc ccaacttgtt tattgcagct    8640
tataatggtt acaaataaag caatagcatc acaaatttca caaataaagc attttttca    8700 ctgcattcta gttgtggttt gtccaaactc atcaatgtat cttatcatgt ctgtataccg    8760
tcgacctcta gctagagctt ggcgtaatca tggtcatagc tgtttcctgt gtgaaattgt    8820
tatccgctca caattccaca acatacga gccggaagca taaagtgtaa agcctggggt    8880
gcctaatgag tgagctaact cacattaatt gcgttgcgct cactgcccgc tttccagtcg    8940
ggaaacctgt cgtgccagct gcattaatga atcggccaac gcgcgggag aggcggtttg    9000 cgtattgggc gctcttccgc ttcctcgctc actgactcgc tgcgctcggt cgttcggctg    9060
cggcgagcgg tatcagctca ctcaaaggcg gtaatacggt tatccacaga atcaggggat    9120
aacgcaggaa agaacatgtg agcaaaaggc cagcaaaagg ccaggaaccg taaaaaggcc    9180
gcgttgctgg cgttttttcca taggctccgc ccccctgacg agcatcacaa aaatcgacgc    9240
tcaagtcaga ggtggcgaaa cccgacagga ctataaagat accaggcgtt tccccctgga    9300
agctccctcg tgcgctctcc tgttccgacc ctgccgctta ccggatacct gtccgccttt    9360
ctcccttcgg gaagcgtggc gctttctcat agctcacgct gtaggtatct cagttcggtg    9420
taggtcgttc gctccaagct gggctgtgtg cacgaacccc ccgttcagcc cgaccgctgc    9480
gccttatccg gtaactatcg tcttgagtcc aacccggtaa gacacgactt atcgccactg    9540
gcagcagcca ctggtaacag gattagcaga gcgaggtatg taggcggtgc tacagagttc    9600
ttgaagtggt ggcctaacta cggctacact agaagaacag tatttggtat ctgcgctctg    9660
ctgaagccag ttaccttcgg aaaaagagtt ggtagctctt gatccggcaa acaaaccacc    9720
gctggtagcg gtggtttttt tgtttgcaag cagcagatta cgcgcagaaa aaaggatct    9780 caagaagatc ctttgatctt ttctacgggg tctgacgctc agtggaacga aaactcacgt    9840
taagggattt tggtcatgag attatcaaaa aggatcttca cctagatcct tttaaattaa    9900
aaatgaagtt ttaaatcaat ctaaagtata tatgagtaaa cttggtctga cagttaccaa    9960
tgcttaatca gtgaggcacc tatctcagcg atctgtctat ttcgttcatc catagttgcc   10020
tgactccccg tcgtgtagat aactacgata cgggagggct taccatctgg ccccagtgct   10080
gcaatgatac cgcgagaccc acgctcaccg gctccagatt tatcagcaat aaaccagcca   10140
gccggaaggg ccgagcgcag aagtggtcct gcaactttat ccgcctccat ccagtctatt   10200
aattgttgcc gggaagctag agtaagtagt tcgccagtta atagtttgcg caacgttgtt   10260
gccattgcta caggcatcgt ggtgtcacgc tcgtcgtttg gtatggcttc attcagctcc   10320
ggttcccaac gatcaaggcg agttacatga tcccccatgt tgtgcaaaaa agcggttagc   10380
tccttcggtc ctccgatcgt tgtcagaagt aagttggccg cagtgttatc actcatggtt   10440
atggcagcac tgcataattc tcttactgtc atgccatccg taagatgctt ttctgtgact   10500
ggtgagtact caaccaagtc attctgagaa tagtgtatgc ggcgaccgag ttgctcttgc   10560
ccggcgtcaa tacgggataa taccgcgcca catagcagaa ctttaaaagt gctcatcatt   10620
ggaaaacgtt cttcggggcg aaaactctca aggatcttac cgctgttgag atccagttcg   10680
atgtaaccca ctcgtgcacc caactgatct tcagcatctt ttactttcac cagcgtttct   10740
```

```
gggtgagcaa aaacaggaag gcaaaatgcc gcaaaaaagg gaataagggc gacacggaaa    10800
tgttgaatac tcatactctt cctttttcaa tattattgaa gcatttatca gggttattgt    10860
ctcatgagcg gatacatatt tgaatgtatt tagaaaaata aacaaatagg ggttccgcgc    10920
acatttcccc gaaaagtgcc acctgac                                       10947
```

```
<210> SEQ ID NO 14
<211> LENGTH: 18
<212> TYPE: PRT
<213> ORGANISM: Artificial Sequence
<220> FEATURE:
<223> OTHER INFORMATION: Glycine-rich linker

<400> SEQUENCE: 14

Gly Gly Arg Ala Ser Gly Gly Ala Ser Gly Gly Ser Gly Gly
1               5                   10                  15

Ser Gly
```

```
<210> SEQ ID NO 15
<211> LENGTH: 13
<212> TYPE: DNA
<213> ORGANISM: Artificial Sequence
<220> FEATURE:
<223> OTHER INFORMATION: Replacement sequence for nucleotides 789-903 of
      vector pPNL9

<400> SEQUENCE: 15
gcaacgatag tgg                                                       13
```

```
<210> SEQ ID NO 16
<211> LENGTH: 90
<212> TYPE: DNA
<213> ORGANISM: Artificial Sequence
<220> FEATURE:
<223> OTHER INFORMATION: Primer

<400> SEQUENCE: 16
ttgctgctaa agaagaaggg gtatctctcg agaaaagaga ggctgaagct tcttacgaat    60
taacacaacc tccatctgtt tctgtttctc                                     90
```

```
<210> SEQ ID NO 17
<211> LENGTH: 73
<212> TYPE: DNA
<213> ORGANISM: Artificial Sequence
<220> FEATURE:
<223> OTHER INFORMATION: Primer

<400> SEQUENCE: 17
ctctaggatc agcgggttta aactcaatgg tgatggtgat gatgaccggt ggatagtacg    60
gtcaccttgg tcc                                                       73
```

```
<210> SEQ ID NO 18
<211> LENGTH: 27
<212> TYPE: PRT
<213> ORGANISM: Artificial Sequence
<220> FEATURE:
<223> OTHER INFORMATION: Localization signal from human cytochrome c
      oxidase subunit 4

<400> SEQUENCE: 18
```

```
Met Leu Ala Thr Arg Val Phe Ser Leu Val Gly Lys Arg Ala Ile Ser
1               5                   10                  15

Thr Ser Val Cys Val Arg Ala Glu Glu Ser Arg
            20                  25
```

<210> SEQ ID NO 19
<211> LENGTH: 109
<212> TYPE: PRT
<213> ORGANISM: Artificial Sequence
<220> FEATURE:
<223> OTHER INFORMATION: Light-chain from single-chain Fv (scFv)

<400> SEQUENCE: 19

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Thr
            20                  25                  30

Tyr Trp Tyr Gln Gln Lys Ala Gly Gln Ala Pro Val Leu Val Ile Tyr
        35                  40                  45

Lys Asp Thr Glu Arg Pro Ser Gly Ile Pro Glu Arg Phe Ser Gly Thr
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Ser Tyr
                85                  90                  95

Val Phe Phe Gly Gly Gly Thr Lys Val Thr Val Leu Ser
            100                 105
```

<210> SEQ ID NO 20
<211> LENGTH: 109
<212> TYPE: PRT
<213> ORGANISM: Artificial Sequence
<220> FEATURE:
<223> OTHER INFORMATION: Light-chain from single-chain Fv (scFv)

<400> SEQUENCE: 20

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Thr
            20                  25                  30

Tyr Trp Tyr Gln Gln Lys Ala Gly Gln Ala Pro Val Leu Val Ile Tyr
        35                  40                  45

Lys Asp Thr Glu Arg Pro Ser Gly Ile Pro Glu Arg Phe Ser Gly Thr
    50                  55                  60

Ser Ser Gly Thr Thr Ala Thr Leu Thr Ile Ser Gly Val Gln Ala Glu
65                  70                  75                  80

Asp Glu Ala Asp Tyr Tyr Cys Gln Ser Ala Asp Ser Ser Gly Ser Tyr
                85                  90                  95

Val Phe Phe Gly Gly Gly Thr Lys Val Thr Val Leu Ser
            100                 105
```

<210> SEQ ID NO 21
<211> LENGTH: 109
<212> TYPE: PRT
<213> ORGANISM: Artificial Sequence
<220> FEATURE:
<223> OTHER INFORMATION: Light-chain from single-chain Fv (scFv)

<400> SEQUENCE: 21

```
Ser Tyr Glu Leu Thr Gln Pro Pro Val Ser Val Ser Pro Gly Gln
1               5                   10                  15

Thr Ala Arg Ile Thr Cys Ser Gly Asp Ala Leu Pro Lys Gln Tyr Thr
            20                  25                  30

Tyr Trp Tyr Gln Gln Lys Ala Gly Gln Ala Pro Val Leu Val Ile Tyr
            35                  40                  45

Lys Asp Thr Glu Arg Pro Ser Gly Ile Pro Glu Arg Phe Ser Gly Thr
50                  55                  60

Ser Ser Gly Thr Thr Ala Thr Leu Thr Ile Ser Gly Val Gln Ala Glu
65                  70                  75                  80

Asp Glu Ala Asp Tyr Tyr Cys Gln Ser Ala Asp Ser Ser Gly Ser His
                85                  90                  95

Val Phe Phe Gly Gly Gly Thr Lys Val Thr Val Leu Ser
            100                 105
```

<210> SEQ ID NO 22
<211> LENGTH: 327
<212> TYPE: DNA
<213> ORGANISM: Artificial Sequence
<220> FEATURE:
<223> OTHER INFORMATION: Light-chain from single-chain Fv (scFv)

<400> SEQUENCE: 22

| | | | | | |
|---|---|---|---|---|---|
| tcttacgaat | taacacaacc | tccatctgtt | tctgtttctc | caggtcaaac tgctagaatt | 60 |
| acttgttctg | gtgatgcttt | gccaaaacaa | tacacttact | ggtatcaaca aaaagctggt | 120 |
| caagctccag | ttttggttat | ttataaagat | actgaaagac | catctggtat tccagaaaga | 180 |
| ttctcaggta | cttcttctgg | tactactgtt | actttgacta | tttctggtgt tcaagctgaa | 240 |
| gatgaagctg | attattattg | tcaatctgct | gattcttctg | gttcttatgt atttttcggt | 300 |
| ggtggtacta | aagttactgt | tttgtct | | | 327 |

<210> SEQ ID NO 23
<211> LENGTH: 327
<212> TYPE: DNA
<213> ORGANISM: Artificial Sequence
<220> FEATURE:
<223> OTHER INFORMATION: Light-chain from single-chain Fv (scFv)

<400> SEQUENCE: 23

| | | | | | |
|---|---|---|---|---|---|
| tcttacgaat | taacacaacc | tccatctgtt | tctgtttctc | caggtcaaac tgctagaatt | 60 |
| acttgttctg | gtgatgcttt | gccaaaacaa | tacacttact | ggtatcaaca aaaagctggt | 120 |
| caagctccag | ttttggttat | ttataaagat | actgaaagac | catctggtat tccagaaaga | 180 |
| ttctcaggta | cttcttctgg | tactactgct | actttgacta | tttctggtgt tcaagctgaa | 240 |
| gatgaagctg | attattattg | tcaatctgct | gattcttctg | gttcttatgt atttttcggt | 300 |

```
ggtggtacta aagttactgt tttgtct                                          327
```

<210> SEQ ID NO 24
<211> LENGTH: 327
<212> TYPE: DNA
<213> ORGANISM: Artificial Sequence
<220> FEATURE:
<223> OTHER INFORMATION: Light-chain from single-chain Fv (scFv)

<400> SEQUENCE: 24

```
tcttacgaat taacacaacc tccatctgtt tctgtttctc caggtcaaac tgctagaatt       60
acttgttctg gtgatgcttt gccaaaacaa tacacttact ggtatcaaca aaaagctggt      120
caagctccag ttttggttat ttataaagat actgaaagac catctggtat tccagaaaga      180
ttctcaggta cttcttctgg tactactgct actttgacta tttctggtgt tcaagctgaa      240
gatgaagctg attattattg tcaatctgct gattcttctg gttctcatgt attttttcggt     300 ggtggtacta aagttactgt tttgtct                                          327
```

<210> SEQ ID NO 25
<211> LENGTH: 6
<212> TYPE: DNA
<213> ORGANISM: Artificial Sequence
<220> FEATURE:
<223> OTHER INFORMATION: Restriction Enzyme site BspEI

<400> SEQUENCE: 25

```
tccgga                                                                   6
```

<210> SEQ ID NO 26
<211> LENGTH: 6
<212> TYPE: DNA
<213> ORGANISM: Artificial Sequence
<220> FEATURE:
<223> OTHER INFORMATION: Restriction Enzyme Site BamHI

<400> SEQUENCE: 26

```
ggatcc                                                                   6
```

<210> SEQ ID NO 27
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 27

```
aagcttccgg atcttacgaa ttaacacaac ctccatctg                              39
```

<210> SEQ ID NO 28
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 28

```
tgatgggatc cagacaaaac agtaactttg gtaccaccac                             40
```

```
<210> SEQ ID NO 29
<211> LENGTH: 50
<212> TYPE: DNA
<213> ORGANISM: Artificial Sequence
<220> FEATURE:
<223> OTHER INFORMATION: Oligonucleotide primer

<400> SEQUENCE: 29
cgacgattga aggtagatac ccatacgacg ttccagacta cgctctgcag            50

<210> SEQ ID NO 30
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 30
tctcgatgcg gccgcttaag acaaaacagt aactttagta ccacc                 45

<210> SEQ ID NO 31
<211> LENGTH: 238
<212> TYPE: PRT
<213> ORGANISM: Artificial Sequence
<220> FEATURE:
<223> OTHER INFORMATION: dL9.3

<400> SEQUENCE: 31

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Thr
            20                  25                  30

Tyr Trp Tyr Gln Gln Lys Ala Gly Gln Ala Pro Val Leu Val Ile Tyr
        35                  40                  45

Lys Asp Thr Glu Arg Pro Ser Gly Ile Pro Glu Arg Phe Ser Gly Thr
    50                  55                  60

Ser Ser Gly Thr Thr Ala Thr Leu Thr Ile Ser Gly Val Gln Ala Glu
65                  70                  75                  80

Asp Glu Ala Asp Tyr Tyr Cys Gln Ser Ala Asp Ser Ser Gly Ser Tyr
                85                  90                  95

Val Phe Phe Gly Gly Gly Thr Lys Val Thr Val Leu Ser Gly Gly Gly
            100                 105                 110

Gly Pro Gly Gly Gly Ser Gly Gly Ser Gly Gly Ser Gly Gly
            115                 120                 125

Gly Ser Tyr Glu Leu Thr Gln Pro Pro Ser Val Ser Val Ser Pro Gly
        130                 135                 140

Gln Thr Ala Arg Ile Thr Cys Ser Gly Asp Ala Leu Pro Lys Gln Tyr
145                 150                 155                 160

Thr Tyr Trp Tyr Gln Gln Lys Ala Gly Gln Ala Pro Val Leu Val Ile
                165                 170                 175

Tyr Lys Asp Thr Glu Arg Pro Ser Gly Ile Pro Glu Arg Phe Ser Gly
            180                 185                 190

Thr Ser Ser Gly Thr Thr Ala Thr Leu Thr Ile Ser Gly Val Gln Ala
        195                 200                 205

Glu Asp Glu Ala Asp Tyr Tyr Cys Gln Ser Ala Asp Ser Ser Gly Ser
    210                 215                 220

Tyr Val Phe Phe Gly Gly Gly Thr Lys Val Thr Val Leu Ser
225                 230                 235
```

NEAR INFRARED FLUOROGEN AND FLUORESCENT ACTIVATING PROTEINS FOR IN VIVO IMAGING AND LIVE-CELL BIOSENSING

PRIORITY

This application claims the benefit of U.S. Provisional Patent Application Ser. No. 61/850,872 filed Feb. 25, 2013 and Ser. No. 61/851,789 filed Mar. 13, 2013; the contents of each of which are incorporated by reference herein in their entirety.

GOVERNMENT RIGHTS

This invention was made with government support under the National Institute of Health 5U54RR022241. The government has certain rights in this invention.

SEQUENCE LISTING

This application includes a Sequence Listing submitted via EFS-Web in computer readable form contained in a 82 Kb byte file entitled 130104_ST25(New).txt created on Jun. 18, 2013 and amended on Oct. 29, 2014 using an IBM-PC machine format, which is hereby incorporated herein by reference in its entirety.

TECHNICAL FIELD

The present disclosure is directed to fluorogens and biosensors comprising fluorogens and fluorogenic activating peptides, methods of producing the fluorogens and biosensors, and methods of using the same.

BACKGROUND

A new technology has been reported that involves protein engineering to obtain single chain antibodies (fluorogen activating peptides, or FAPs) that bind engineered chromophores (Fluorogens) that are not fluorescent in aqueous solution but which become highly fluorescent when bound to a corresponding FAP. See, Szent-Gyorgyi C. et al., Fluorogen-activating single-chain antibodies for imaging cell surface proteins, *Nat Biotechnol*, 26:235-240, (2008); Patent Application WO 2008/092041 A2; and U.S. Published Application US2011/0159519 A1, the contents of each of which are hereby incorporated by reference herein. Various FAP-Fluorogen combinations have been used to detect the location of cellular proteins that have been genetically labeled with FAPs. Szent-Gyorgyi, et al., *Nat Biotechnol*. 26:235-240, (2008). Also FAP-Fluorogen combinations have been developed that allow detection of pH and calcium concentrations in the local environment of the protein labeled with a FAP. See, Grover A. et al, Genetically Encoded pH Sensor for Tracking Surface Proteins through Endocytosis, *Angewante Chemie*, published online: 29 Mar. 2012. This technology has been used in biological assays in drug discovery and basic research to track membrane surface proteins that are exposed to agonist and antagonist molecules. See, Wu Y. et al., Discovery of regulators of receptor internalization by high throughput cytometry, *Mol. Pharmacol*. (2012) PMID: 22767611.

At present, the longest wavelength of fluoromodule excitation/emission maxima has been 633/667 nm. This partially limits the application of the FAP technology, particularly towards the interrogation of tissue slices, organs, and whole animals, which absorb and scatter visible light. Further, conventional fluorescence-based drug discovery assays are sometimes confounded by various compounds present in most drug candidate libraries that are themselves fluorescent when the assay is carried out. There are very few such drug candidates that fluoresce at long wavelengths, especially in the Near Infrared Region (NIR).

SUMMARY OF THE INVENTION

The invention described herein comprises new embodiments of a fluorogen having the structure:

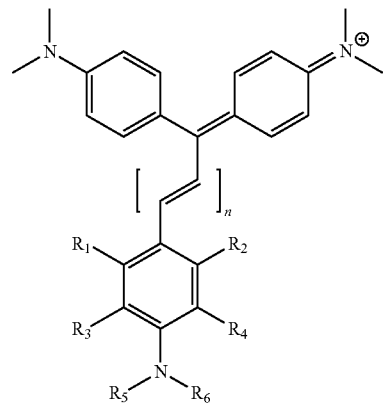

wherein $R_1$, $R_2$, $R_3$, and $R_4$ are the same or different and are selected from H, Cl, Br, I, F, an electron donating group, or an electron withdrawing group; $R_5$ and $R_6$ are the same or different and are selected from substituents that permit passage through a plasma membrane and substituents that interfere with passage through a plasma membrane, or facilitate conjugation to another chemical species; and, n is an integer from 0 to 2.

The substituents that permit passage through a plasma membrane may contain one or more of hydrogen, alkyl groups, substituted alkyl groups, esters, aryl groups, substituted aryl groups, amines, and amides. The length of the substituents should be sufficient to pass through the plasma membrane, for example, a length of 18 carbon atoms or less should be sufficient in most situations. The substituents that interfere with passage through a plasma membrane may comprise hydrophilic or charged groups, and may contain one or more of sulfonated groups, carboxylating groups, and multiple hydroxy groups.

The invention further comprises the various embodiments of the fluorogens and cognate fluorogen-activating peptides (FAPs) that maximally absorb and emit 70 and 66 nm longer wavelengths, respectively, than previous described fluorogen/FAP complexes. In various embodiments, the invention may be characterized as a composition comprised of (i) one of the several embodiments of the fluorogen and (ii) a fluorogen-activating peptide non-covalently complexed with the fluorogen, to form a fluoromodule that yields an emission peak in the near infrared region. The fluorogen-activating peptide may be a protein derived from the variable chain or variable chains of an scFv. The FAP molecule may be selected from the group consisting of SEQ. ID. NO. 1, 2 and 3.

In various embodiments, the invention may comprise a ligand-dye complex, comprising a cognate ligand of a dye non-covalently bound to the dye, wherein the cognate ligand comprises a polypeptide derived from the variable chain or variable chains of an scFv that possesses an amino acid sequence having at least 85% to 100% sequence identity, and preferably, at least 90%, more preferably at least 95%, and most preferably at least 95% to about 100% sequence identity to the polypeptide selected from the group consisting of SEQ ID NO: 1, 2, 3, 20 and 21, wherein the dye comprises any of the embodiments of the fluorogen described herein and derivatives, analogs, and equivalents thereof, that bind the fluorogen-activating peptide, and wherein the bound dye and ligand exhibit a detectable fluorescence signal in the near infrared region of the spectrum.

A novel fluorescent tag was developed, based upon a genetically targeted fluorogen-activating protein and cognate fluorogenic dye that yields emission with a peak at 733 nm exclusively when complexed as a "fluoromodule". This tool improves substantially over previously described far-red/NIR fluorescent proteins in terms of brightness, wavelength, and flexibility by leveraging the flexibility of synthetic chemistry to produce novel chromophores. Indeed, the basic aromatic fluorogen structure can be modified with, for example, an alkyl group, and/or with charged groups on a linker. These modifications can be used to control water solubility and the ability of the fluorogen to cross, or be blocked by, biological membranes. This technology was used for in vivo imaging applications which resulted in robust, in vivo detection of FAPs binding the novel fluorogen SKC602 in living mice. These results suggest the new fluoromodule can bypass previous limitations imposed for fluorescence-based studies within tissues, intact organs, and living organisms.

The development of these new fluorogen structures and cognate FAPs that absorb and emit at wavelengths longer that the previous fluorogen/FAPs described above will allow for a number of new applications and improvements upon existing ones. First, fluorescence detection in the Near-Infrared region (NIR, >700 nm-2500 nm) permits detection of fluorescent structures deeper in tissues. This is because hemoglobin and other naturally occurring biomolecules absorb light strongly in the visible light region, limiting the excitation and detection of traditional fluorescent probes deep in tissues. However, longer NIR wavelengths penetrate tissues more deeply, allowing more efficient excitation of the probe, as well as more effective capture of the emitted light.

NIR detection assays that can be executed at longer wavelengths will result in less false-positive or false-negative events caused by fluorescent drug candidates. Additionally, there is less biological background fluorescence at longer wavelengths which would subsequently increase detection sensitivity.

Additionally, a new detection range can be used in combination with FAP-Fluorogens that are detected at multiple wavelengths in the visible range of the spectrum allowing the simultaneous detection of several biological properties of individual living or fixed cells. Multi-parameter detection not only speeds the amount of data per unit time but allows correlation of multiple parameters. This has great importance in studies of correlated physiological and biochemical activities in cells.

Finally, longer-wavelength fluorogens can be used for development of physiological indicators that emit in the long wavelength region. For example, targeted pH indicators can be constructed that emit in the NIR by covalent linkage of a pH probe to such fluorogen. The pH sensitivity of the FAP-targeted fluorogen then responds to the pH of the environment as sensed by the pH-sensitive component of the two-part fluorogen.

It should be understood that this disclosure is not limited to the embodiments disclosed in this Summary, and it is intended to cover modifications that are within the spirit and scope of the invention, as defined by the claims.

BRIEF DESCRIPTION OF THE DRAWINGS

The characteristics and advantages of the present disclosure may be better understood by reference to the accompanying figures.

FIGS. 9A through R show Tables 9A through G of nucleotide sequences and features thereof use to express the compositions described herein.

DETAILED DESCRIPTION AND BEST MODE OF IMPLEMENTATION

Figure 1:
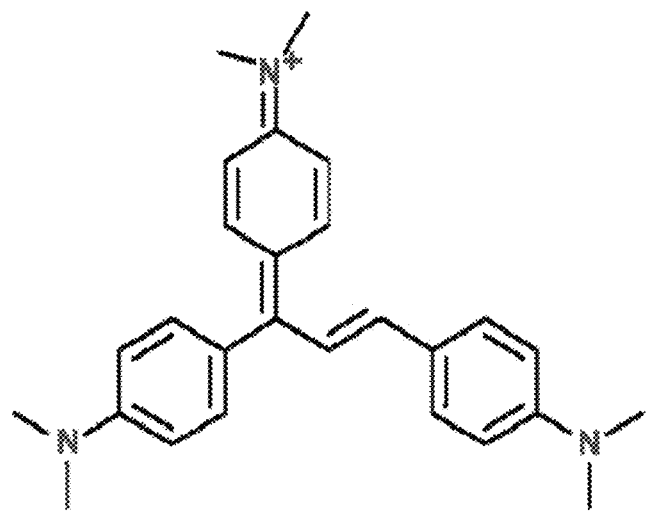
FIGS. 1A and 1B illustrate the chemical structures of two embodiments of the dye described herein, SKC602 (A) and SKC728 (B).
Figure 1:
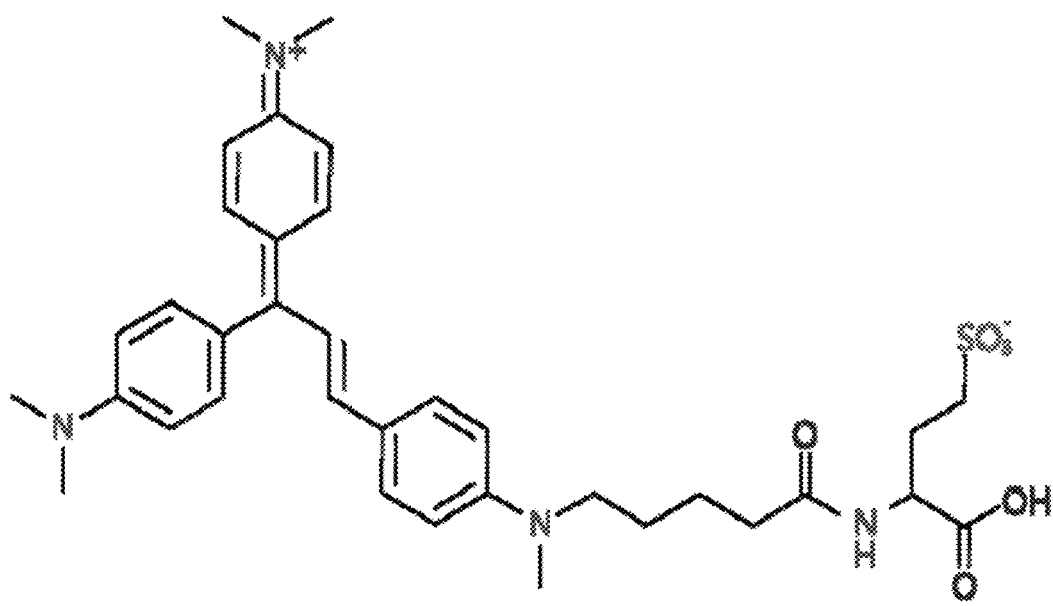

In the present application, including the claims, other than where otherwise indicated, all numbers expressing quantities, values or characteristics are to be understood as being modified in all instances by the term "about." Thus, numbers may be read as if preceded by the word "about" even though the term "about" may not expressly appear with the number. Accordingly, unless indicated to the contrary, any numerical parameters set forth in the following description may vary depending on the desired properties one seeks to obtain in the compositions and methods according to the present disclosure. At the very least, and not as an attempt to limit the application of the doctrine of equivalents to the scope of the claims, each numerical parameter described in the present description should at least be construed in light of the number of reported significant digits and by applying ordinary rounding techniques.

Any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The articles "a" and "an" are used herein to refer to one or to more than one (i.e., to at least one) of the grammatical object of the article. By way of example, "an element" means one element or more than one element.

As used herein, the term "amino acid" is intended to embrace all molecules, whether natural or synthetic, which include both an amino functionality and a carboxylate functionality and capable of being included in a poly(amino acid) polymer. Exemplary amino acids include, for example, naturally-occurring amino acids; analogs, derivatives and congeners thereof; amino acid analogs having variant side chains; and all stereoisomers of any of the foregoing.

As used herein, the terms "peptide," "polypeptide", and "protein" are synonymous and used interchangeably to refer to a polymer or oligomer of amino acids. In addition, as used herein, the terms "peptide," "polypeptide", and "protein" may refer to a discrete sub-unit of a larger peptide construct. As used herein, the term "peptide construct" refers to a peptide comprising discrete peptide domains covalently linked to form the larger peptide construct. The constituent peptides of a peptide construct may be covalently linked through peptide bonds. Any one or more constituent peptides of a peptide construct may also respectively possess an active domain that possesses various activity or functionality, including, but not limited to, receptor-ligand functionality, ligand-target functionality, enzyme-substrate functionality, and antibody-antigen functionality.

As used herein, the term "ligand" refers to a binding moiety for a specific target molecule. The molecule may comprise a cognate receptor, a protein, a small molecule, a hapten, an epitope, or any other relevant molecule. The molecule may comprise an analyte of interest. As used herein, the term "epitope" refers to a structure on a molecule that interacts with another molecule, such as, for example, an antibody or antibody fragment. In various embodiments, epitope refers to a desired region on a target molecule that specifically interacts with another molecule comprising a cognate ligand.

The term "Fv" refers herein to an antibody fragment that consists of one $V_H$ and one $V_L$ domain held together by non-covalent interactions. The term "dsFv" is used herein to refer to an Fv with an engineered intermolecular disulfide bond to stabilize the $V_H$-$V_L$ pair. Methods for preparing Fv fragments are known in the art. See, for example, U.S. Pat. No. 4,462,334; Hochman et al., *Biochemistry*, 12, 1130, 1973; Sharon et al., *Biochemistry*, 15, 1591, 1976; and U.S. Pat. No. 4,355,023.

The terms "single chain antibody," "single-chain Fv," and "scFv" refer herein to an antibody fragment comprising the variable light chain ($V_L$) and variable heavy chain ($V_H$) antibody domains covalently connected to one another by a peptide linker moiety. Either the $V_L$ or the $V_H$ may be the amino-terminal domain. The peptide linker may be of variable length and composition, and its presence will be denoted using a short dash, e.g. $V_H$-$V_L$. In various embodiments, peptide linkers may comprise segments of glycine and serine residues, optionally with some glutamic acid or lysine residues interspersed in the peptide linker sequence. Methods for preparing scFvs are known in the art. See, for example, International Application No. PCT/US/87/02208 and U.S. Pat. Nos. 4,704,692; 4,946,778, each of which is incorporated by reference herein in its entirety.

The terms "fluorogen-activating protein" and "fluorogen-activating peptide" refer to polypeptides and combinations of polypeptides derived from the variable chains of scFvs such as $V_L$, $V_L$-$V_L$, $V_H$, and $V_H$-$V_H$, and multiples thereof, that are able to form a fluorescent complex with cognate fluorogen molecules. The fluorogen-activating peptides described presently may be of the conformation $V_L$-$V_L$, where each $V_L$ is derived from the same scFv light chain, or may be one or more $V_L$ chain, with or without linkers interposed between the $V_L$ chains, and in each case, are either identical, or differ in amino acid sequence.

As used herein, the term "fluorogen" refers to a chemical moiety that exhibits fluorogenic properties. Fluorogens include, but are not limited to, fluorogenic dyes, such as, for example, the new fluorogens described herein, and derivatives, analogs and equivalents thereof, thiazole orange, malachite green, dimethyl indol red, and derivatives thereof. Not wishing to be bound by theory, the fluorogenic properties of dyes such as, for example, thiazole orange, malachite green, dimethyl indol red, and derivatives thereof are believed to be due to an environmentally sensitive conformational relaxation pathway (Magde et al., *Chem. Phys. Letters*, 24, 144-148, (1974); Duxbury, *Chem. Rev.*, 93, 381-433, (1993); Furstenberg et al., *JACS*, 128, 7661-7669, (2006); Silvia et al., *JACS*, 129, 5710-5718, (2007); see also Senutovitch et al., A Variable Light Domain Fluorogen Activating Protein Homodimerizes To Activate Dimethylindole Red, *Biochemistry*, 51, 2471-2485 (2012)).

The term "sequence homology" refers to the proportion of base matches between two nucleic acid sequences or the proportion of amino acid matches between two amino acid sequences. When sequence homology is expressed as a percentage, e.g., 50%, the percentage denotes the proportion of matches over the length of sequence from a desired sequence (e.g., SEQ. ID NO: 1) that is compared to some other sequence. Gaps (in either of the two sequences) are permitted to maximize matching; gap lengths of 15 bases or less are usually used, 6 bases or less are used more frequently, with 2 bases or less used even more frequently. The term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, determining the number of positions at which the identical amino acids occur in both sequences to yield the number of matched positions, dividing the number of matched positions by the total number of positions in the comparison window, and multiplying the result by 100 to yield the percentage of sequence identity. Methods to calculate sequence identity are known to those of skill in the art.

A new fluorescent tag has been developed which is based upon a genetically targeted fluorogen-activating protein and cognate fluorogenic dyes that yields emission with a peak at 733 nm exclusively when complexed as a "fluoromodule". This is 66 nm farther red than previously characterized fluorogen/Fluorogen-Activating Peptides (FAPs) currently available and can address the substantial challenges in fluorescent imaging of tissue slices and whole organisms. Autofluorescence and absorption via intrinsic chromophores, such as flavins, melanin, and hemoglobins, confound and degrade output from all fluorescent tags. An "optical window," farther red than most autofluorescence sources and in a region of low hemoglobin and water absorbance, lies between 650 and 900 nm. This valley of relative optical clarity is an attractive target for fluorescence-based studies within tissues, intact organs, and living organisms. To date, few genetically encoded fluorescent proteins have ventured into this window, primarily due to limitations imposed by chromophore size and conformation.

Examples of two embodiments of the chemical structures of the dyes are shown in FIG. 1. It is noteworthy that the basic aromatic fluorogen structure can be modified with alkyl groups (for example, using the short hand nomenclature, SKC602) and with charged groups on a linker (for example, SKC728). Alkyl groups, for example, increase the hydrophobicity of the fluorogen. The length of the substituents used to modify the fluorogen may be long enough to pass through the plasma membrane, for example, a length of 18 or less carbon atoms in an alkyl or substituted alkyl chain should be sufficient in most situations. These modifications can be used to control water solubility and the ability of the fluorogen either to cross biological membranes, or be excluded from them. The distributed positive charge of SKC602 allows it to pass through cell membranes, accessing any labeled protein on the cell surface, in the cytoplasm, and inside membrane-bound organelles such as the nucleus and mitochondria. The sulfonate substituent of SKC728 blocks penetration of plasma membranes, enabling selective labeling of FAP-tagged proteins that have exclusively been exposed to the external environment of the cell. If it is desirable for the fluorogen to enter the cytoplasm of the cell to reach an internal FAP, then a fluorogen such as SKC602 would be used. If it is desirable for the fluorogen to selectively access FAPs that are attached to membrane surface proteins, for example to quantify their density on the cell surface in a drug discovery assay, then a more highly charged fluorogen such as SKC728 would be selected.

The spectral properties of fluoromodules assembled from combinations of dL9.2 (SEQ. ID. NO. 2) and dL9.5 (SEQ. ID. NO. 3) with SKC602 and SKC728 are listed in Table 1. dL9.2 (SEQ. ID. NO. 2) is an asymmetric light chain ($V_L$-$V_L$) tandem dimer based upon dL9 (SEQ. ID. NO. 1), hosting the V70A mutation on the N-terminal light chain. dL9.5 (SEQ. ID. NO. 3) is a symmetric light chain ($V_L$-$V_L$) tandem dimer based upon dL9.2 (SEQ. ID. NO. 2) with the V70A mutation propagated to C-terminal chain, and an additional Y96H mutation that is present on both chains. These genetically encoded fluorescent labels yield good brightness in the far-red/NIR spectral regime when combined with their cognate fluorogens.

TABLE 1

| | Ex/Em (nm) | ε ($M^{-1}cm^{-1}$) | Φ | Brightness (ε · Φ · 1 × $10^{-3}$) |
|---|---|---|---|---|
| dL9.2:SKC602 (SEQ. ID. NO. 2:SKC602) | 702/731 | $1.2 \times 10^5$ | 0.17 | 20 |
| dL9.5:SKC602 (SEQ. ID. NO. 3:SKC602) | 702/731 | $1.2 \times 10^5$ | 0.17 | 20 |
| dL9.2:SKC728 (SEQ. ID. NO. 2:SKC728) | 703/733 | $9.0 \times 10^4$ | 0.21 | 19 |
| dL9.5:SKC728 (SEQ. ID. NO. 3:SKC728) | 703/733 | $9.8 \times 10^4$ | 0.23 | 23 |

Figure 2:
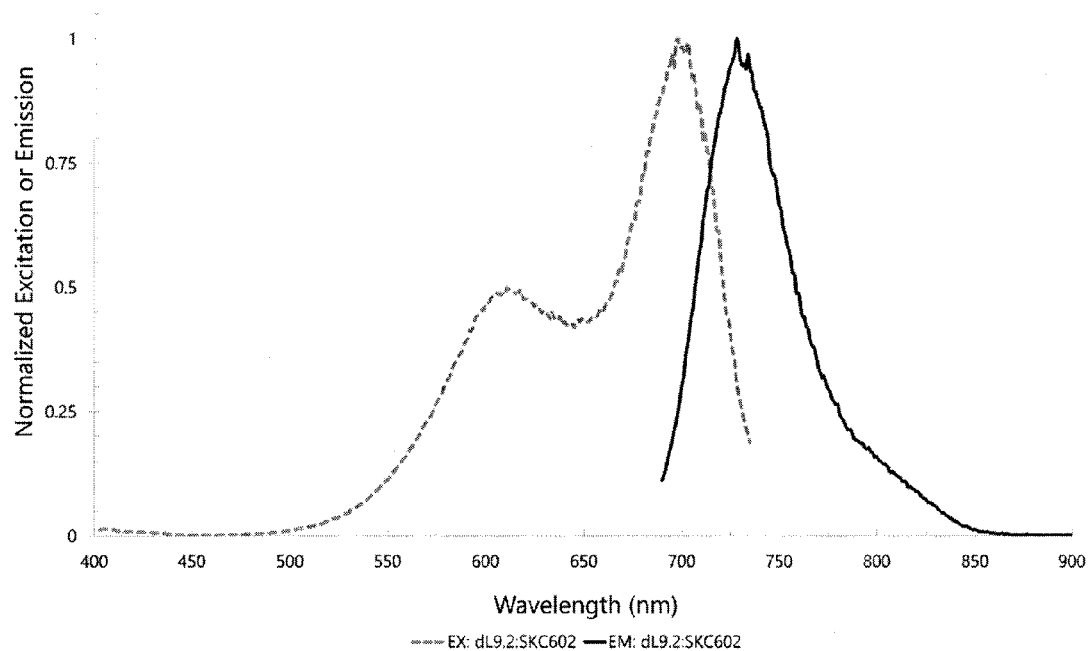
FIG. 2 is a graph of the normalized excitation (dotted line) and emission (solid line) spectra of the dL9.2:SKC602 (SEQ. ID. NO. 2:SKC602) embodiment of a fluoromodule in phosphate buffered saline (PBS).

The normalized excitation and emission spectra of the dL9.2:SKC602 (SEQ. ID. NO. 2:SKC602) fluorogen is shown in FIG. 2. The dL9.2:SKC602 (SEQ. ID. NO. 2:SKC602) fluoromodule (black, solid) emits at longer wavelengths than existing biliverdin-binding infra-red fluorescent proteins, while retaining the ability to be excited effectively by common illumination sources such as the HeNe laser line (633 nm) as well as lamps equipped with Cy5™-compatible excitation filters. Spectra of dL9.5 (SEQ. ID. NO. 3) bound to SKC602 are highly similar. Excitation and emission spectra are normalized to the highest value within each data set.

Figure 10:
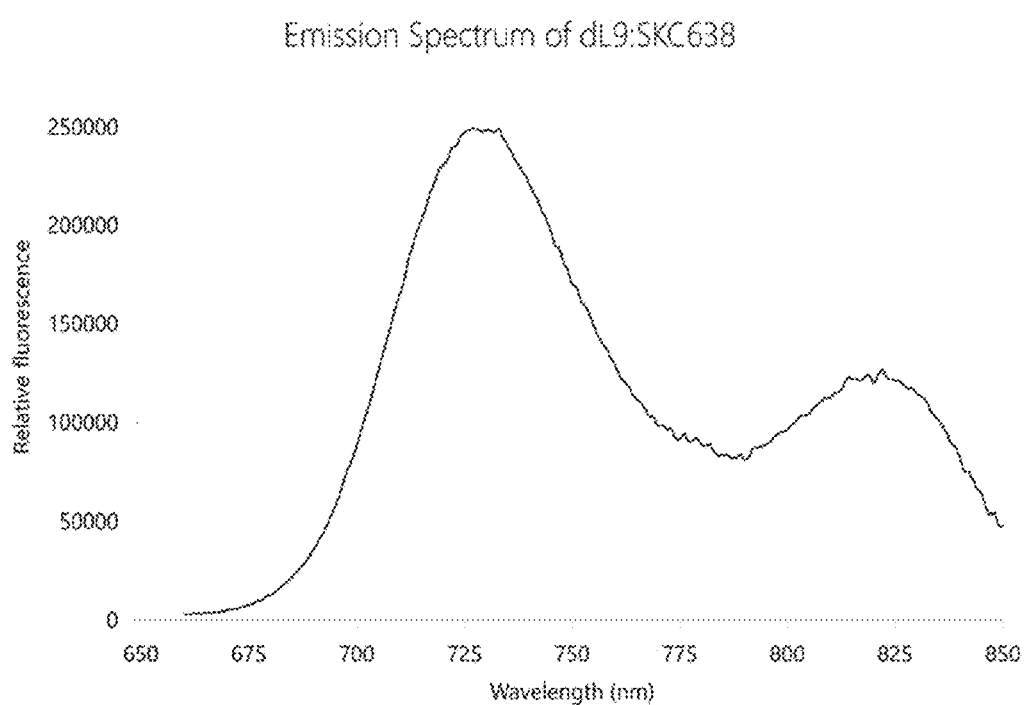
FIG. 10 is a graph showing the spectral characterization of fluorescence activation for the solution resulting from incubation of SKC638 with a molar excess of purified dL9 (SEQ. ID NO: 1). The non-normalized emission spectrum shown (black, solid) was acquired using a Quantamaster™ fluorometer (PTI) by excitation through monochromators set at 630 nm.

To further demonstrate the utility of extended fluorogen analogues, the extended SKC602 derivative, SKC638 (Example 2) was incubated with a molar excess of purified dL9 (SEQ. ID NO: 1). The resulting solution was analyzed for fluorescence activation, and the spectral characterization is shown in FIG. 10. The non-normalized emission spectrum shown (black, solid) was acquired using a Quantamaster fluorometer (PTI) by excitation through monochromators set at 630 nm. The primary peak near 730 nm is likely due to contaminating SKC602, while a second, smaller peak is clearly observed near 823 nm, and is likely contributed by the extended chromophore of SKC638.

Figure 11:
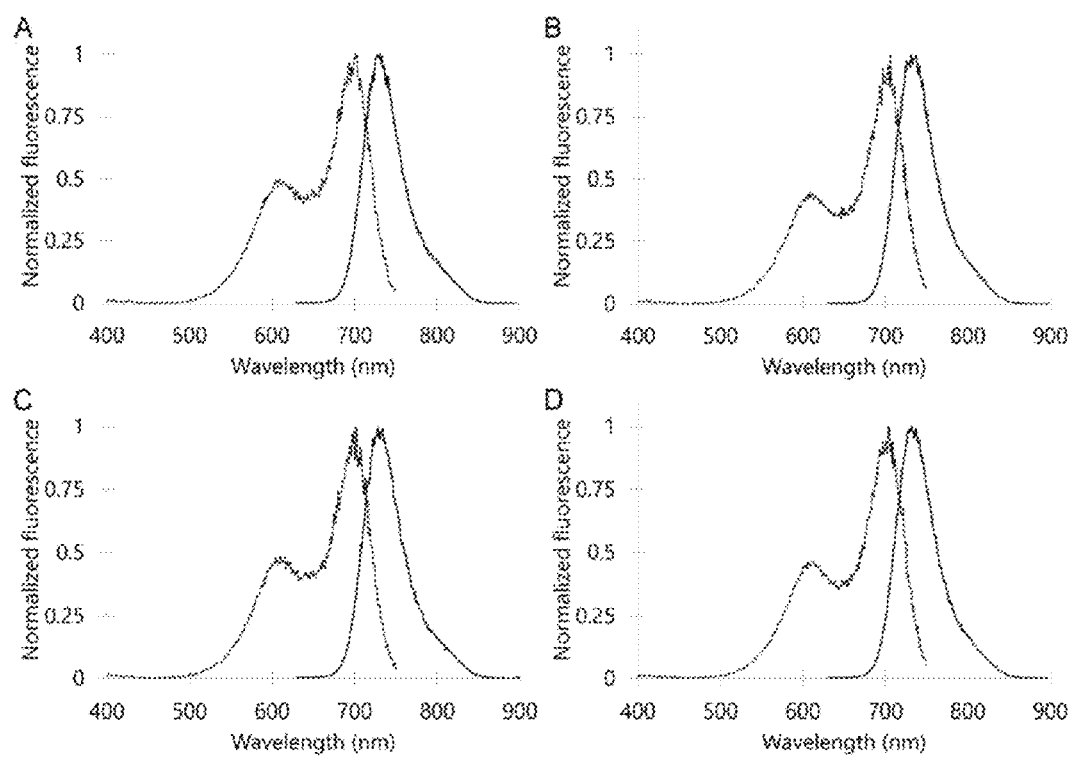
FIG. 11 shows the spectral properties of monomeric FAP variants mL9.3 and mL9.5 (SEQ. ID. NO. 20 and 21, respectively) bound to, and activating the fluorogens SKC602 and SKC728. Panel A shows the normalized excitation and emission spectra of mL9.3:SKC602 (SEQ. ID. NO. 20:SKC602). Panel B shows the normalized excitation and emission spectra of mL9.3:SKC728 (SEQ. ID. NO. 21:SKC728). Panels C and D show the spectra corresponding to mL9.5:SKC602 (SEQ. ID. NO. 21:SKC602) and mL9.5:SKC728 (SEQ. ID. NO. 21:SKC728), respectively. As in FIG. 2, all spectra were obtained in PBS, pH 7.4.

While the peptide linker that joins the $V_L$ units in dL9.2 (SEQ. ID. NO. 2) and dL9.5 (SEQ. ID. NO. 3) enhance fluorogen binding affinity and binding rate by reducing the entropic cost of assembly around the fluorogen, the linker is not strictly necessary for fluorogenic activation. We show in FIGS. 11 and 12, via spectral analysis and confocal microscopy respectively, that the monomeric FAPs mL9.3 (SEQ. ID. NO. 20) (L9 V70A, corresponding to SEQ. ID. NO. 1) and mL9.5 (SEQ. ID. NO. 21) (L9 V70A, Y96H, corresponding to SEQ. ID. NO. 1) also bind SKC602 and SKC728 to induce NIR fluorescence. In panels A and B of FIG. 11, we observe that purified monomeric FAP mL9.3 (SEQ. ID. NO. 20) induces fluorescence in SKC602 and SKC728, respectively. In panels C and D, corresponding spectra from mL9.5: SKC602 (SEQ. ID. NO. 21:SKC602) and mL9.5:SKC728 (SEQ. ID. NO. 21:SKC728) fluoromodules are shown. Spectra were obtained using a Quantamaster™ fluorometer (PTI) equipped with dual monochromators on both excitation and emission light paths.

Figure 12:
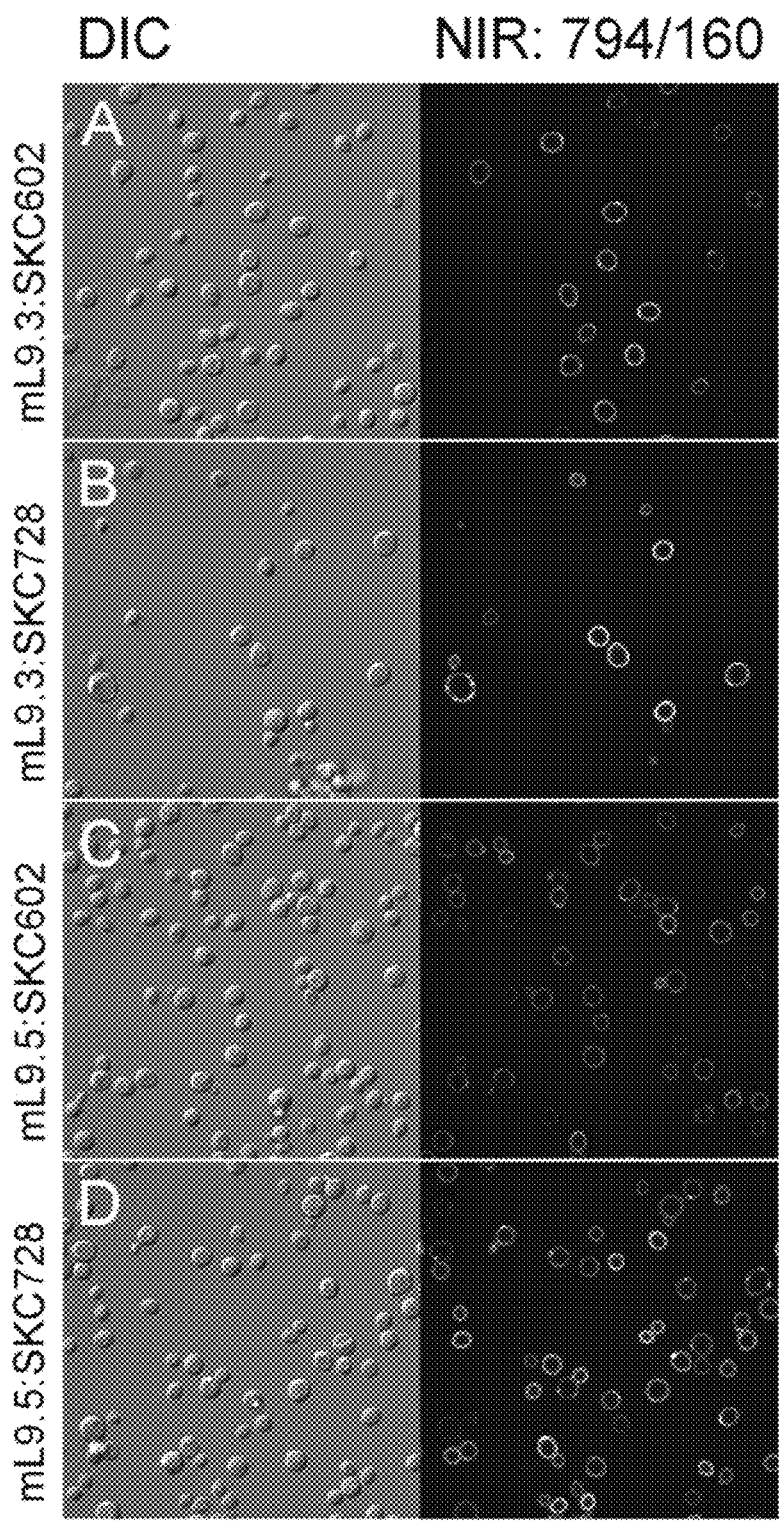
FIG. 12 shows *S. cerevisiae* hosting plasmids that express either mL9.3 (SEQ. ID. NO. 20) or mL9.5 (SEQ. ID. NO. 21) in a surface-tethered format, in brightfield (DIC) and NIR fluorescence as excited by 641 nm light (NIR:794/160) channels. Not all cells visible in the DIC channel express the FAP, and these non-expressing cells are not visible in the NIR channel. Samples contain either SKC602 or SKC728 as labeled, and demonstrate that single-chain versions of dL9.2 (SEQ. ID. NO. 20) and dL9.5 (SEQ. ID. NO. 21) remain competent to activate fluorescence in their cognate fluorogens.

FIG. 12 shows that the same proteins can achieve fluorogen activation to yield NIR fluorescence when expressed on the surface of S. cerevisiae. The DIC column shows brightfield images of induced yeast hosting a vector that allows surface-tethered expression of FAPs, while the NIR:794/160 column shows NW fluorescence from individual yeast that express the FAPs. Note that not all yeast seen in the brightfield image are fluorescent—this is due to non-complete retention of the expression plasmid during cell division cycles, and assists in demonstrating that SKC602 and SKC728, by themselves, do not cause NIR fluorescence in the absence of cognate FAP.

To further demonstrate the utility of extended fluorogen analogues, the extended SKC602 derivative, SKC638 (Example 2) was incubated with a molar excess of purified dL9 (SEQ. ID NO: 1). The resulting solution was analyzed for fluorescence activation, and the spectral characterization is shown in FIG. 10. The non-normalized emission spectrum shown (black, solid) was acquired using a Quantamaster fluorometer (PTI) by excitation through monochromators set at 630 nm. The primary peak near 730 nm is likely due to contaminating SKC602, while a second, smaller peak is clearly observed near 823 nm, and is likely contributed by the extended chromophore of SKC638.

Figure 3:
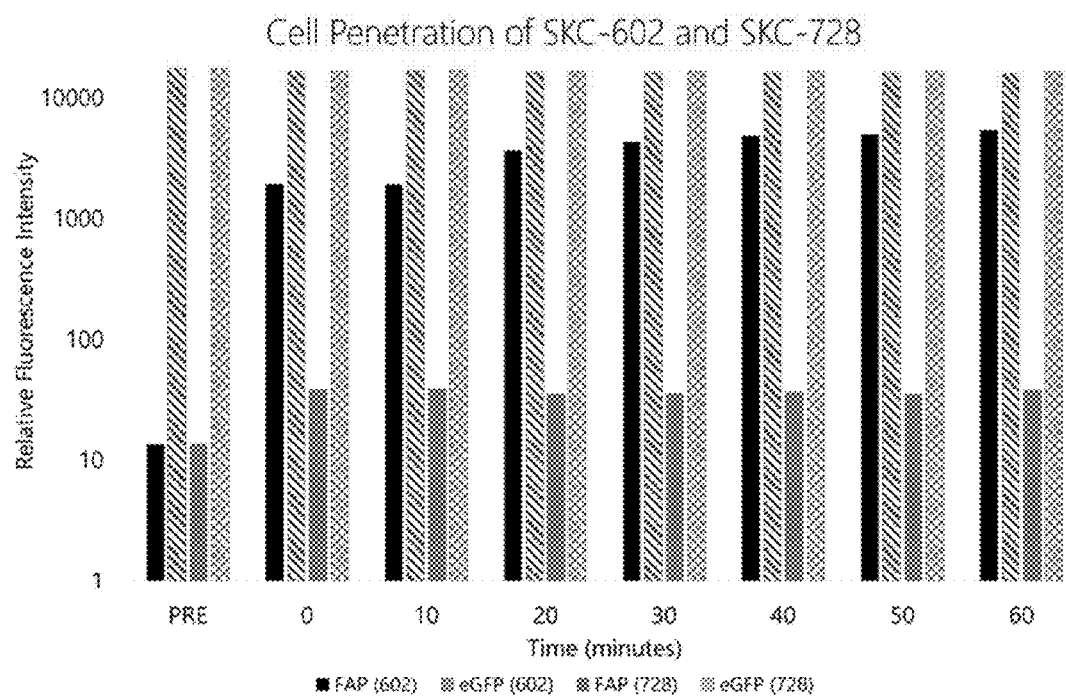
FIG. 3 is a graph that illustrates the fluorescence intensity over time from incubation of mammalian cells expressing a cytoplasmic dL9.5-eGFP (SEQ. ID. NO. 3:eGFP) (green fluorescent protein) fusion protein with dye embodiments SKC602 and SKC728: signal intensities indicate that SKC602 enters cells and binds to the FAP, while SKC728 is excluded. The GFP signal remains constant, showing that the total amount of FAP in each cell did not change over the course of the experiment.

In one example, incubation with mammalian cells expressing a cytoplasmic dL9.5-eGFP (SEQ. ID. NO. 3:eGFP) fusion protein demonstrated the membrane permeability difference between SKC602 and SKC728, and the results are in FIG. 3. The GFP fluorescence intensity describes the total fluoromodule-eGFP fusion protein expressed within each cell and as expected, this quantity does not change over the course of the experiment. The PRE set denotes baseline fluorescence of the cell population (approximately 20000 cells per acquisition) prior to addition of fluorogen to 100 nM per sample. Fluorescence intensity increases substantially upon addition of SKC602, but not SKC728. Furthermore, SKC728 is excluded from entry for at least one hour after addition of the fluorogen.

Figure 4:
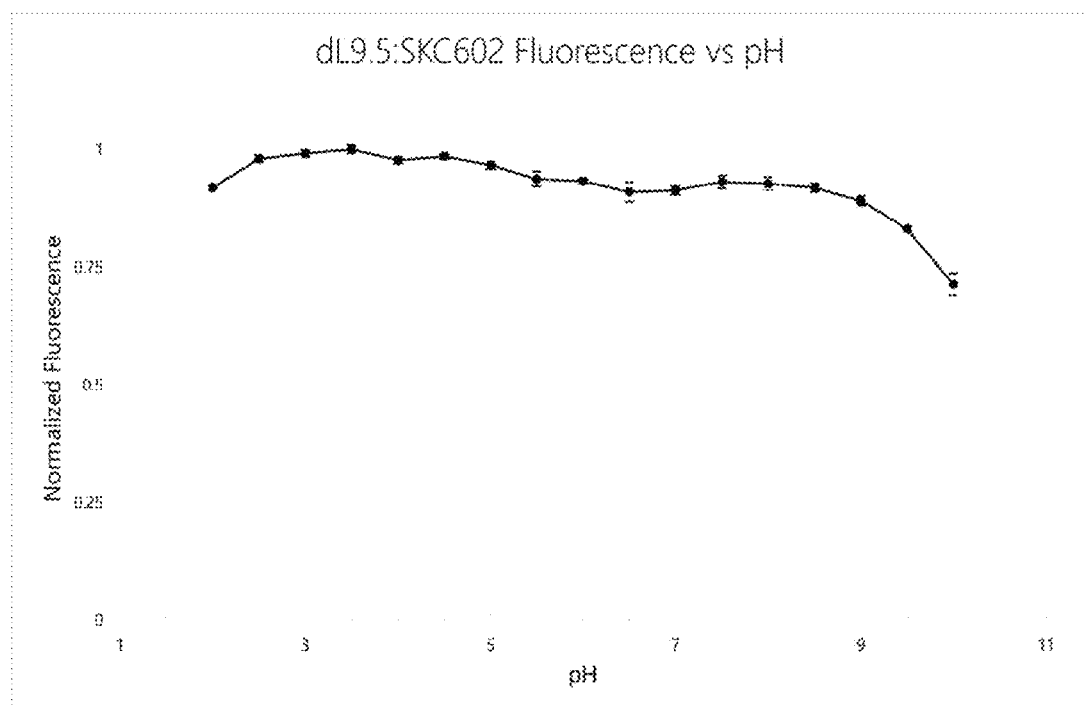
FIG. 4 is a graph that illustrates normalized fluorescence of the dL9.5:SKC602 (SEQ. ID. NO. 3:SKC602) embodiment of a fluoromodule as a function of pH. The average values of five separate measurements are displayed (circles); bars denoting extreme values within the measurement set, and normalization is to the maximum value within all data points. The observed trend is highly similar to that of dL9.2:SKC602 (SEQ. ID. NO. 2:SKC602) and dL9.2:SKC728 (SEQ. ID. NO. 2:SKC728).

In another example, the dL9.5:SKC602 (SEQ. ID. NO. 3:SKC602) fluoromodule exhibited exceptional stability across a broad pH range. Fluoromodules incubated in Carmody buffer with 300 mM NaCl, spanning pH 2-10 in 0.5 pH unit increments, were assessed for fluorescence after three hours and the results are summarized in FIG. 4. The averages of five replicates per pH increment are shown as filled circles; bars denote extreme values within each replicate set, and normalization is to the maximum value within all data points. Fluorescence intensity did not fluctuate over the course of one hour of measurement. A longer-term assessment of dL9.2: SKC602 (SEQ. ID. NO. 2:SKC602) and dL9.2:SKC728 (SEQ. ID. NO. 2:SKC728) yielded similar results and remained stable over 24 hours. Stability of this degree allows the fluoromodule probe to be useful in an extremely wide range of cellular contexts.

Figure 5:
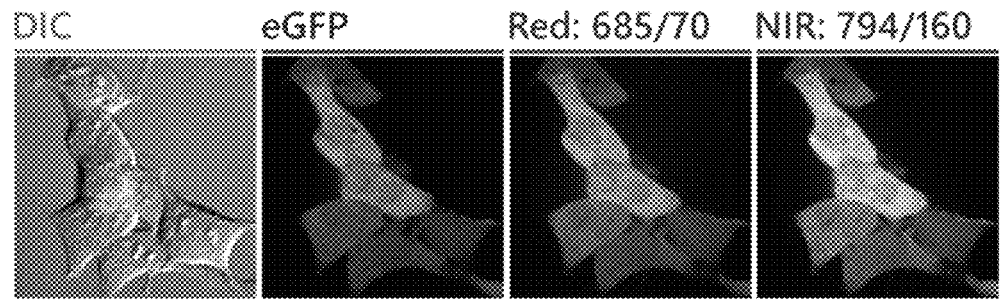
FIG. 5 shows a series of photomicrographs of HEK293 cells expressing cytoplasmic dL9.5-eGFP (SEQ. ID. NO. 3:eGFP). The HEK293 cells were incubated with SKC602 and imaged via spinning disk confocal microscope. A differential interference contrast (DIC) image was obtained to show all cells. Fluorescence images of the same field of view were obtained by exciting the fluoromodule with a 641 nm laser. NIR emission was collected through 685/70 nm and 794/160 nm filters as shown in figure headings. dL9.5 (SEQ. ID. NO. 3) affords easily detected signal in the NIR channel.

In another example, the dL9.5:SKC602 (SEQ. ID. NO. 3:SKC602) fluoromodule produces NIR fluorescence when expressed in the cytoplasm of the HEK293 mammalian cell lines. The expressed construct was imaged using an Andor Revolution XD spinning disk confocal (GFP 488:525/50, dL9.5 (SEQ. ID. NO. 3) 640:685/70 AND 640:794/160, 60×1.49 NA oil immersion objective) and the results are shown in FIG. 5. The protein is functional and exhibits even cytoplasmic distribution. Non-transfected cells do not exhibit fluorescence. The fluorogen was not washed away prior to imaging.

Figure 6:
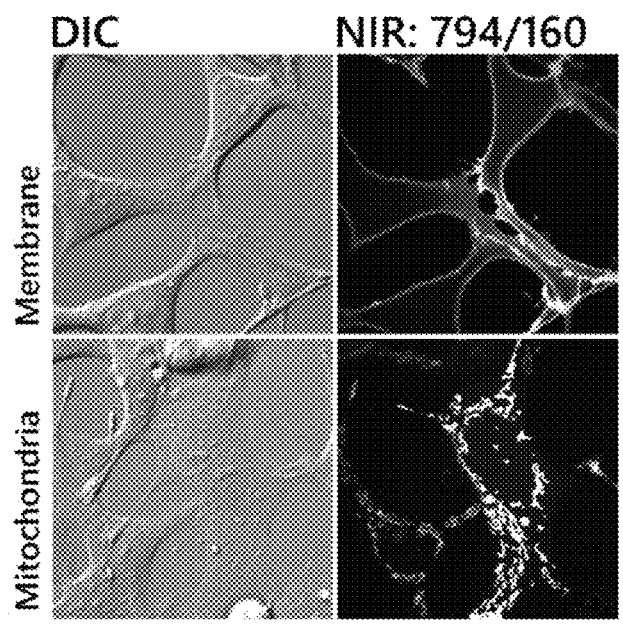
FIG. 6 shows photomicrographs (DIC and NIR fluorescence) of the fluoromodule being used to target a probe to desired subcellular locations with high specificity. (Top: Plasma membrane, Bottom: Mitochondria).

In addition to demonstrative fluoromodule activity and non-aggregation when expressed in the cytoplasm of living mammalian cells, we have also demonstrated high-fidelity targeting of the FAP to various subcellular locations. FIG. 6 demonstrates precise labeling of FAP tethered to the exterior plasma membrane surface of HEK293 cells by virtue of activating the membrane impermeant fluorogen SKC728, as well as FAP targeted to the mitochondrial matrix, activating the membrane permeant fluorogen SKC602. Imaging conditions were similar to those described for obtaining FIG. 5.

Experiments in a mouse model indicate that the described NIR fluoromodules are of substantial utility as a novel genetically encoded fluorescent tag that features relatively high brightness in addition to long-wavelength excitation and emission. Application of these properties is demonstrated in FIG. 7, which shows a nude mouse that has been subcutaneously injected with 100 FAP-expressing, pre-labeled cells. Bright NIR fluorescence from the fluoromodules are easily detected through the skin of the animal, suggesting that far fewer cells could be monitored by pairing fluoromodules with currently existing imaging technologies.

Figure 8:
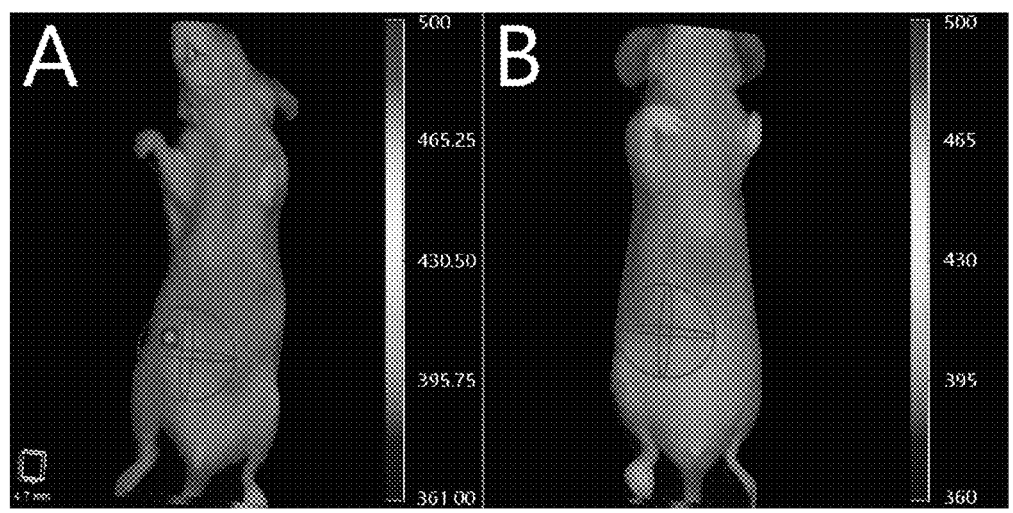
FIG. 8A demonstrates detection of NIR fluorescence from FAP-expressing cells injected intraperitoneally into mice that were then administered fluorogen SKC602 via intravenous injection.
FIG. 8B shows a mouse that was imaged without injection of transfected cells.

Further utility of NIR fluoromodules as applied to small animal imaging is demonstrated in FIG. 8A, in which is shown a nude mouse that has been injected intraperitoneally with 7×10⁶ FAP-expressing cells that were not pre-labeled with fluorogen. Fluorescence arose from the injected cells only after intravenous administration of SKC602 (8B depicts a control mouse not injected with transfected cells). These data indicate that cohorts of FAP-expressing cells can be tracked deep within the body of a small animal, and that the NIR fluorogen SKC602 can propagate through the body, activating at sites of interest designated by the presence of cognate FAP (analogous experiments with SKC728 indicate similar properties).

Synthesis Pathways for Example Fluorogens

Example 1

Synthesis of [(E)-N-(4-(1,3-bis(4-(dimethylamino)phenyl) allylidene)cyclohexa-2,5-dien-1-ylidene)-N-methylmethanaminium] (SKC602)

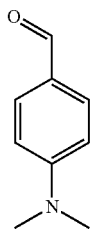

4-(dimethylamino)benzaldehyde
Chemical Formula: $C_9H_{11}NO$
Exact Mass: 149.0841
Molecular Weight: 149.1897

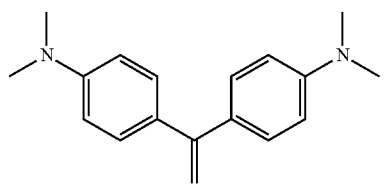

Chemical Formula: $C_{18}H_{22}N_2$
Exact Mass: 266.1783
Molecular Weight: 266.3807

60% $HClO_4$
Acetic anhydride

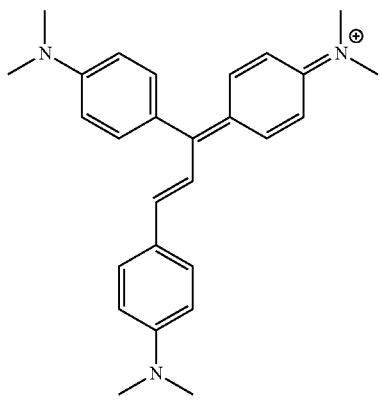

Chemical Formula: $C_{27}H_{32}N_3^+$
Exact Mass: 398.2591
Molecular Weight: 398.5625
SKC-602

4-Dimethyl amino benzaldehyde (149 mg, 1 mmol) and 4,4'-vinylidene bis(N,N-dimethylaniline) (300 mg, 1.12 mmol) were dissolved in 5 ml acetic anhydride. 200 μl of 60% perchloric acid was added slowly. The mixture was refluxed for 3 hour under stirring and cooled to room temperature. The mixture was precipitated by diethyl ether, and the blue residue was purified by silica gel column chromatography using 10% methanol in chloroform to give a 242 mg deep blue solid as the product. MW $C_{27}H_{32}N_3^+$ 398.56 g/mol (61% yields).

$^1$H-NMR (CD$_3$OD): δ 7.72-7.85 (m, 2H); 7.53 (d, 2H); 7.45 (d, 1H); 7.12 (d, 1H); 6.52-6.98 (m, 8H); 3.24 (d, 12H); 2.9 (m, 6H). ESI-MS (+): 398.3.

Example 2

Synthesis of SKC638

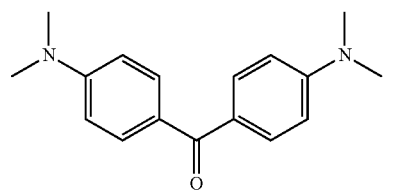

Chemical Formula: $C_{17}H_{20}N_2O$
Exact Mass: 268.16
Molecular Weight: 268.35

Acetic anhydride
$HClO_4$

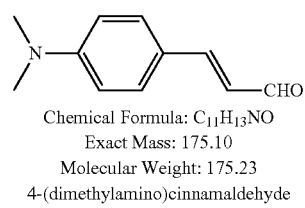

Chemical Formula: $C_{11}H_{13}NO$
Exact Mass: 175.10
Molecular Weight: 175.23
4-(dimethylamino)cinnamaldehyde

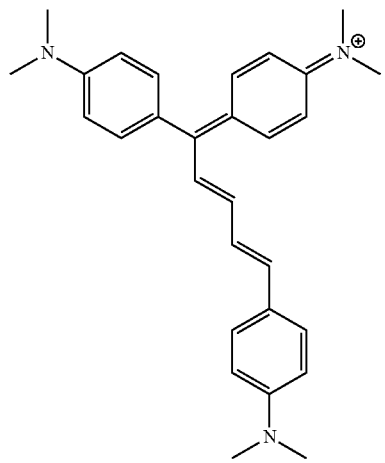

Chemical Formula: $C_{29}H_{34}N_3^+$
Exact Mass: 424.27
Molecular Weight: 424.60
SKC-638

4-(dimethylamino)cinnamaldehyde (355 mg, 2 mmol) and 4,4'-vinylidene bis(N,N-dimethylaniline) (585.37 mg, 2.2 mmol) were dissolved in 10 ml acetic anhydride and 300 μl of $HClO_4$ was added. The mixture was refluxed for 3 hour under stirring and cooled to room temperature. The mixture was precipitated by diethyl ether, and the residue was purified by silica gel column chromatography using 5% methanol in chloroform to give a 202 mg solid (24% yields) as the product. MW: $C_{29}H_{34}N_3$+424.27 g/mol; ESI-MS (+): 424.67.

Example 3

Synthesis of [Ethyl 5-(methyl(phenyl)amino)pentanoate] (SKC659)

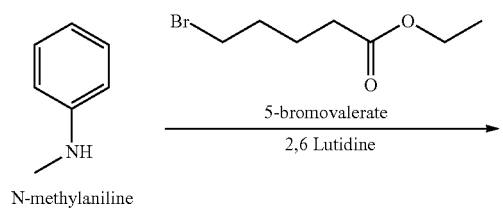

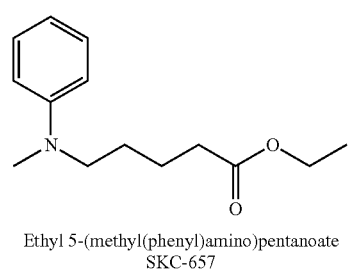

Ethyl 5-(methyl(phenyl)amino)pentanoate
SKC-657

5.52 ml (48 mmol) of N-Methyl aniline, 8 ml Bromovalerate (50.2 mmol) and 2,6-lutidine (5.82 ml, 50.2 mmol) were taken in 100 ml acetonitrile and the reaction was refluxed for 24 hour under stirring. Acetonitrile was removed under vacuum and residues were dissolved in ether. The organic phase was washed with water. After drying over magnesium sulfate and filtering, the solvent was removed to give a brown liquid. The residue was purified by flash chromatography on silica gel using a 10% ethyl acetate in hexane as eluent gave 10.1 g light yellow oil as product. MW $C_{14}H_{21}NO_2$ 235.32 g/mol (yields 90%).

$^1$H-NMR (CDCl$_3$): δ 7.25 (m, 2H); 6.72 (m, 3H); 4.15 (m, 2H); 3.35 (m, 2H); 2.94 (s, 3H); 2.35 (m, 2H); 1.67 (m, 4H); 1.27 (m, 3H). ESI-MS (+): 235.62

Example 4

Synthesis of [Ethyl 5-((4-formylphenyl)(methyl)amino)pentanoate] (SKC659)

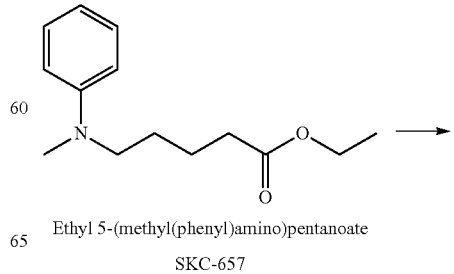

Ethyl 5-(methyl(phenyl)amino)pentanoate
SKC-657

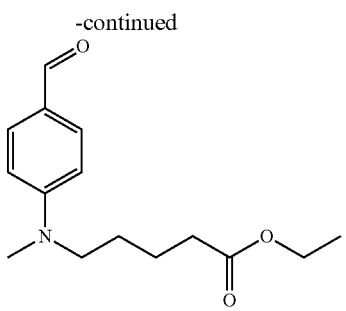

Ethyl 5-((4-formylphenyl)(methyl)amino)pentanoate
SKC-659

2.94 g (1.25 mmol) of SKC657 was dissolved in 10 ml dry DMF and cool to −5° C. by salt ice bath. 5 ml of POCl$_3$ was added drop wise over a period of 1 hour at −5° C. and stir the reaction mixture at room temperature for 20 hour. Raise the temperature to 90° C. for 2.5 hour. Cool to room temperature and pour in 200 g of ice water, neutralized by solid K$_2$CO$_3$. Extract the mass by 3×75 ml CHCl$_3$. The combined organic layer was washed whit 2×100 ml water and dried over anhydrous MgSO$_4$. Concentrated under vacuum gave 2.2 g light brown oil (66% yield). MW C$_{15}$H$_{21}$NO$_3$ 263.33 g/mol $^1$H-NMR (CDCl$_3$): δ 9.76 (s, 1H); 7.75 (d, 2H); 6.80 (d, 2H); 4.14 (m, 2H); 3.44 (m, 2H); 3.07 (s, 3H); 2.35 (m, 2H); 1.68 (m, 4H); 1.27 (m, 3H). ESI-MS (+): 263.23

Example 5

Synthesis of (E)-N-(4-(1-(4-(dimethylamino)phenyl)-3-(4-((5-ethoxy-5-oxopentyl)(methyl)amino)phenyl)allylidene)cyclohexa-2,5-dien-1-ylidene)-N-methylmethanaminium (SKC660)

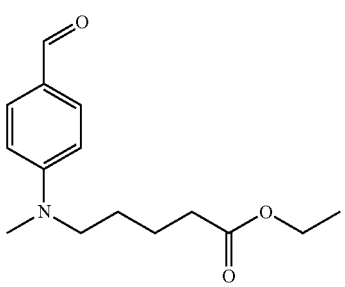

ethyl 5-((4-formylphenyl)(methyl)amino)pentanoate
SKC-659

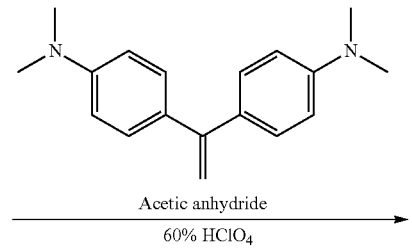

Acetic anhydride
60% HClO$_4$

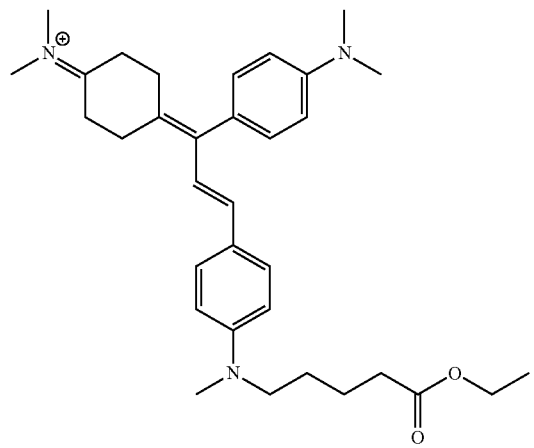

(E)-N-(4-(1-(4-(dimethylamino)phenyl)-3-(4-((5-ehtoxy-5-oxopentyl)(methyl)amino)phenyl)allylidene)cyclohexa-2,5-dien-1-ylidene)-N-methylmethanaminium
SKC-660

1.3 g (5 mmol) of SKC-659 and 1.6 g (6 mmol) of 4,4'-vinylidene bis(N,N-dimethylaniline) were suspended in 15 ml acetic anhydride and 400 µl of 60% perchloric acid was added slowly. The blue color reaction mixture was stirred at room temperature for 20 hour, concentrated and the residue was purified by flash chromatography on SiO$_2$ using a 5% methanol in chloroform as eluent gave 600 mg deep blue solid as compound (yields 24%). MW $C_{33}H_{42}N_3O_2{}^+$ 512.70 g/mol.

$^1$H-NMR (CD$_3$OD): δ 7.42-7.99 (m, 9H); 6.76-6.97 (m, 5H); 4.15 (m, 2H), 3.61 (m, 2H); 3.23 (s, 6H); 2.39 (m, 2H); 2.01 (s, 6H); 1.71 (m, 4H); 1.25 (m, 3H).

Example 6

Synthesis of SKC672

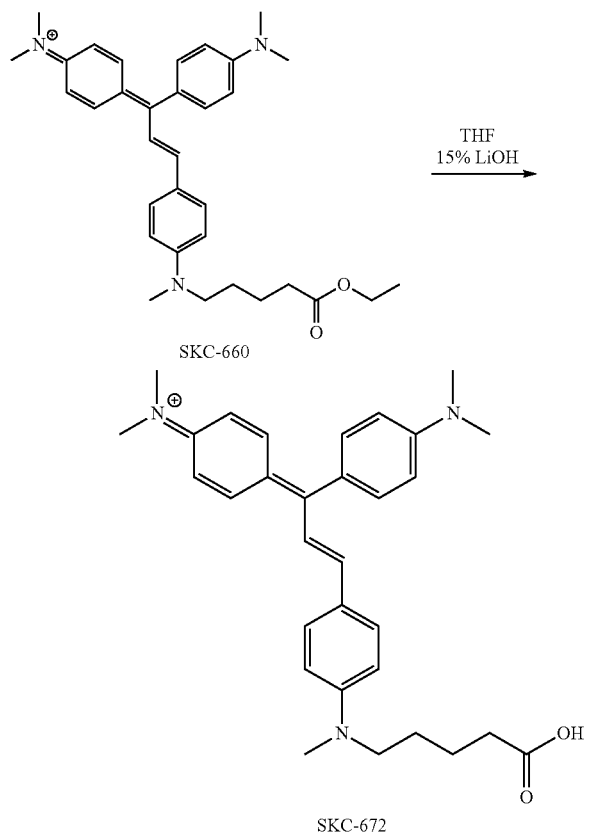

450 mg of SKC660 was suspended in 50 ml THF. 15% LiOH aqueous solution (10 ml) was added and stirred at room temperature for 24 hour. The organic layer was separated. The aqueous layer was extracted with 3×50 ml CHCl$_3$ and combined with the organic layer. The organic fraction was dried over anhydrous MgSO$_4$, and concentrated to 20 ml. 200 µl of 60% HClO$_4$ was added slowly and stirred at room temperature for 1 hour. Upon concentration the blue residue was purified by flash chromatography on silica gel using a 10% methanol in chloroform as the eluent to provide a 200 mg (47% yield) pure product. MW $C_{31}H_{38}N_3O_2{}^+$ 484.65 g/mol.

$^1$H-NMR (CD$_3$OD): δ 6.65-7.88 (m, 14H); 3.33 (m, 9H); 2.99 (m, 2H); 2.91 (m, 3H); 2.31 (m, 2H); 1.66 (m, 4H). ESI-MS (+): 484.3.

The following analog of SKC602 and SKC638 can be prepared by substituting an appropriate starting material in Table 2 for 4-Dimethyl amino benzaldehyde or 4-(dimethylamino)cinnamaldehyde in Examples 1 or 2, respectively.

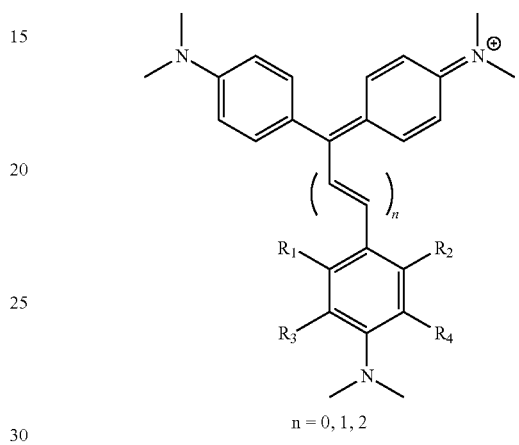

n = 0, 1, 2 wherein R$_1$, R$_2$, R$_3$, R$_4$ are the same or different and may be selected from H, Cl, Br, I, F, electron donating groups, and electron withdrawing groups.

The following analog of SKC672 can be prepared as described below.

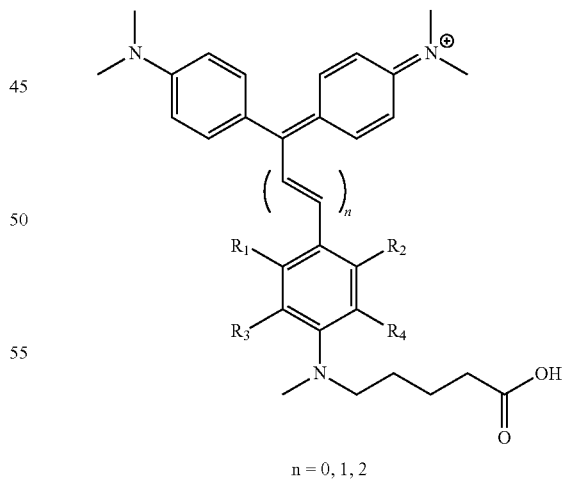

n = 0, 1, 2 wherein R$_1$, R$_2$, R$_3$, R$_4$ are the same or different and may be selected from H, Cl, Br, I, F, electron donating groups, and electron withdrawing groups.

Example 7

General Synthesis of the Malachite Green Analog

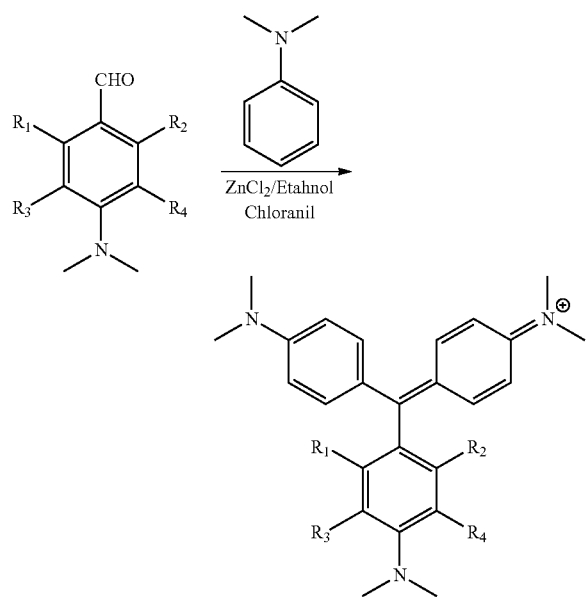

SKC602 analog:

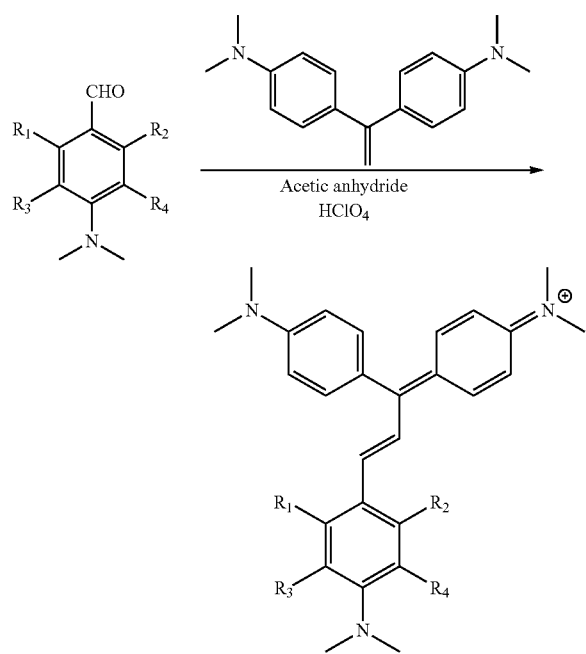

SKC638 analog:

See the procedures described in Chao, Herbert S. I., Improved synthesis of trans-4-(diethyl amino)cinnamaldehyde, *Synthetic Communications*, 18(14), pp. 1641-50 (1988), incorporated herein by reference.

The following compounds/intermediates are exemplary of compounds/intermediates that can be used for above mentioned reactions. They are either commercially available or can be synthesized by procedures well known to persons of skill in the art. Those in the art will recognize that other compounds, starting materials, and intermediaries may be used as well to synthesize analogs, derivatives and equivalents to the fluorogens falling within the scope of the present invention.

TABLE 2

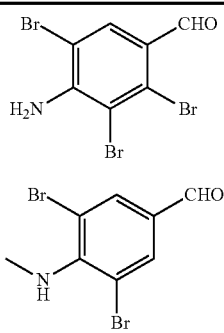

TABLE 2-continued
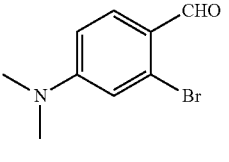
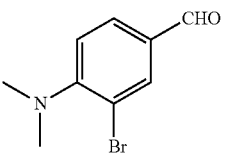
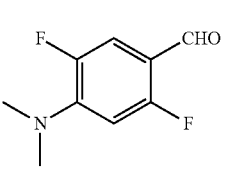
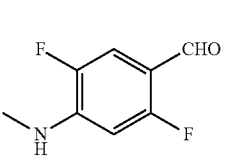
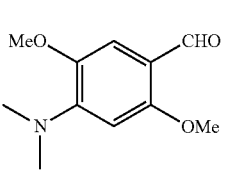
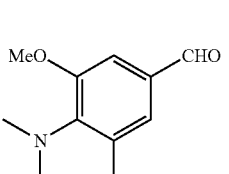
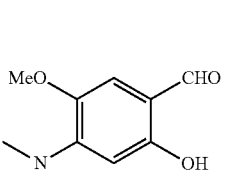
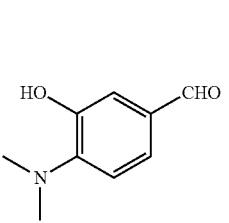
TABLE 2-continued
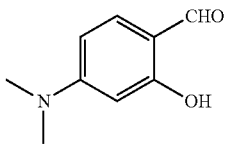
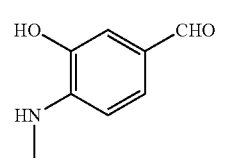
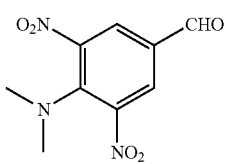 [SMILES: CN(C)c1c([N+](=O)[O-])cc(C=O)cc1[N+](=O)[O-]]
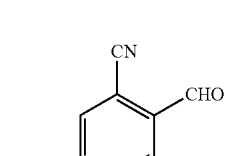
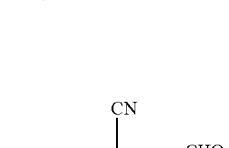
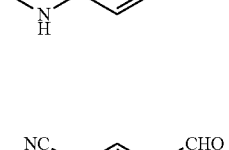
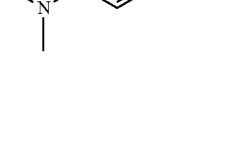

TABLE 2-continued
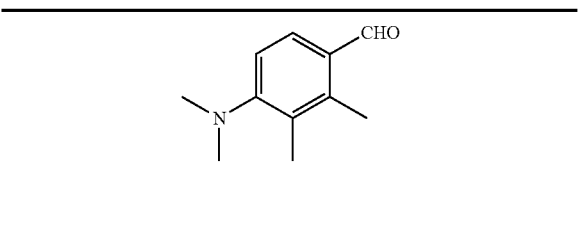
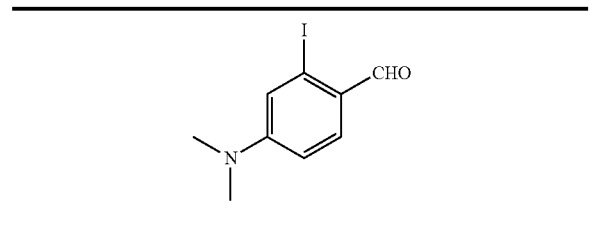
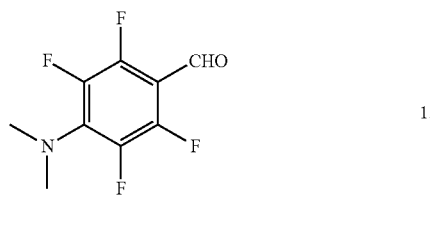
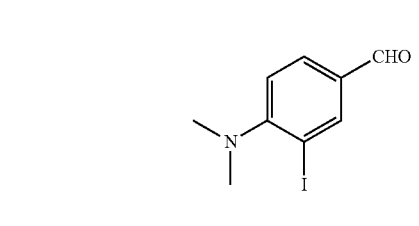
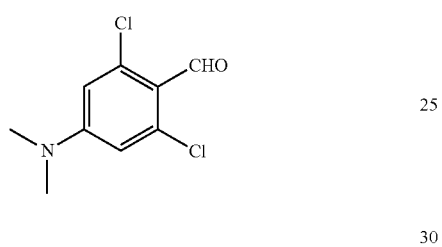
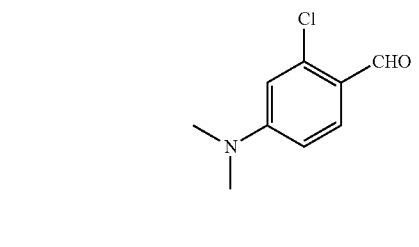
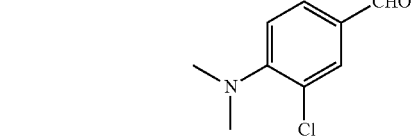
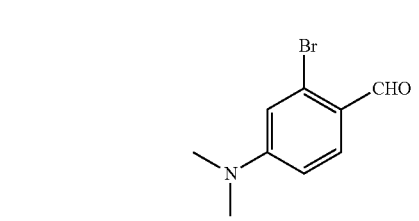
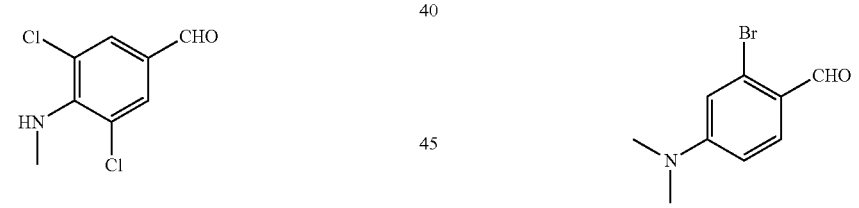
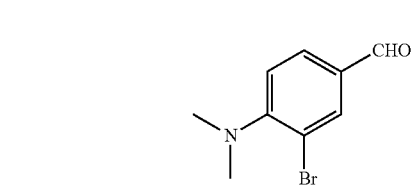
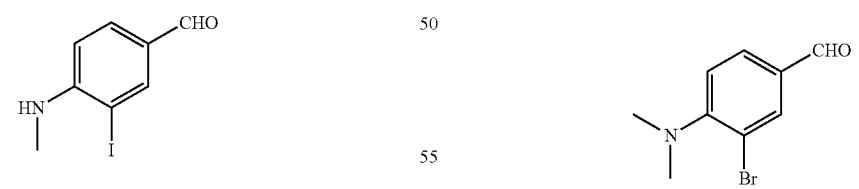
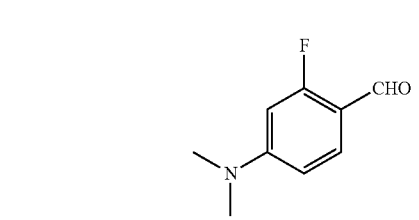
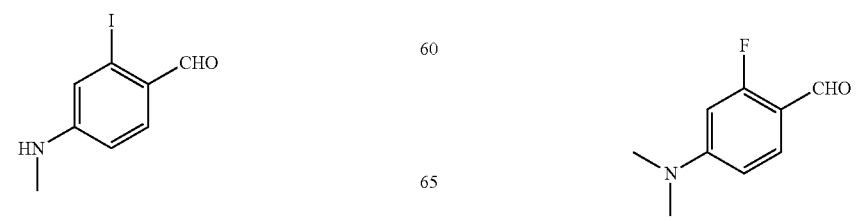

TABLE 2-continued

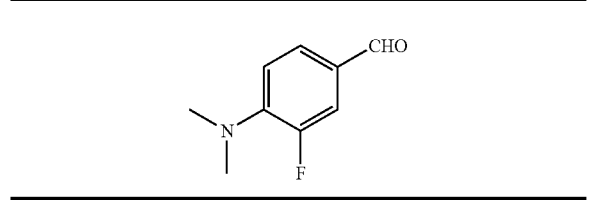

Example 8

Synthesis of SKC722

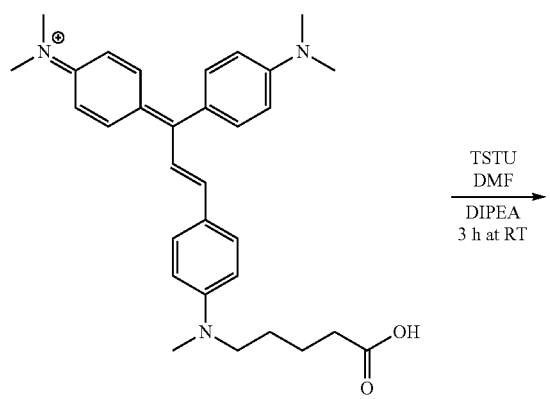

Chemical Formula: $C_{31}H_{38}N_3O_2^+$
Exact Mass: 484.2959
Molecular Weight: 484.6518
SKC-672

$\xrightarrow{\text{TSTU, DMF, DIPEA, 3 h at RT}}$

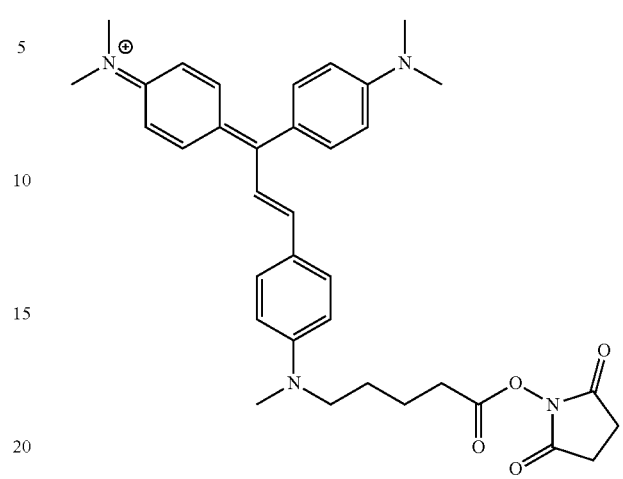

Chemical Formula: $C_{35}H_{41}N_4O_4^+$
Exact Mass: 581.3122
Molecular Weight: 581.7239
SKC-722

SKC672 (162 mg) was dissolved in 3 ml anhydrous DMF. 160 mg of TSTU and 25 μl of Diisopropyl ethyl amine were added and the mixture was stirred at room temperature for 3 hours. The mixture was concentrated under vacuum and the residue was precipitated by diethyl ether and dried to give 173 mg of active ester SKC-722. MW $C_{35}H_{41}N_4O_4^+$ 581.72 g/mol. (yield 89%). ESI-MS (+): 581.3.

Example 9

Synthesis of SKC728

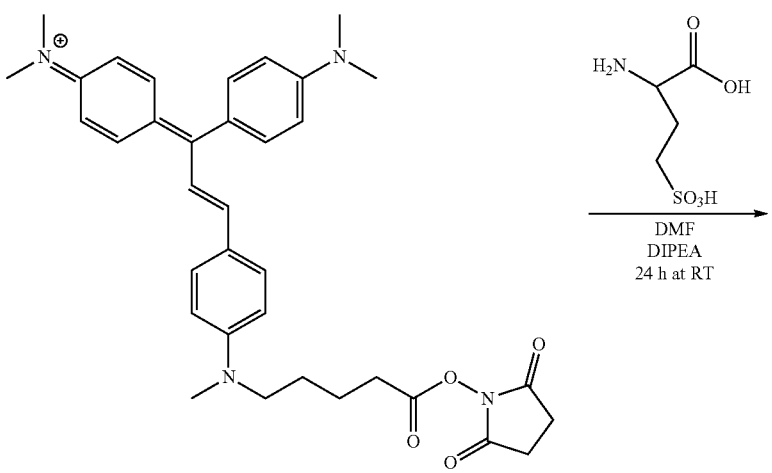

Chemical Formula: $C_{35}H_{41}N_4O_4^-$
Exact Mass: 581.3122
Molecular Weight: 581.7239
SKC-722

$\xrightarrow{\text{DMF, DIPEA, 24 h at RT}}$

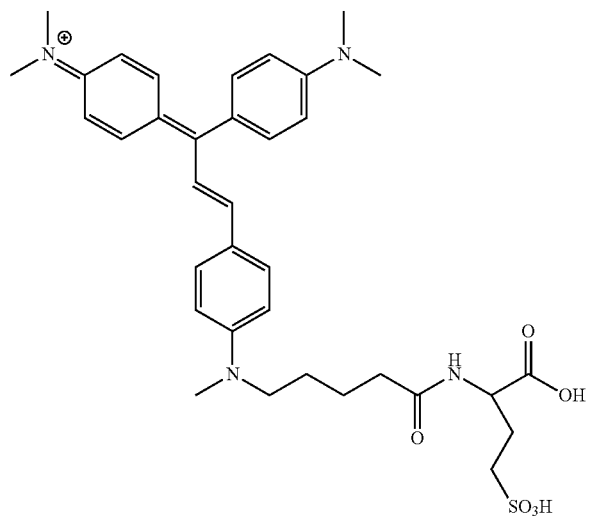

Chemical Formula: $C_{35}H_{45}N_4O_6S^+$
Exact Mass: 649.3054
Molecular Weight: 649.8195
SKC-728

SKC722 (58 mg, 1 mmol) and DL-Homocysteic acid (23 mg, 1.25 mmol) were dissolved in 2 ml anhydrous DMF. DIPEA (20 μl) was added and stirred at room temperature for 24 hours. The mixture was concentrated and the residue was purified by flash chromatography on $SiO_2$ using a 20% methanol in chloroform as eluent, providing 51 mg of pure product. MW: $C_{35}H_{45}N_4O_6S^+$ 649.81 g/mol (78% yields). ESI-MS (+): 649.3.

Synthesis Click Chemistry Intermediate

The following compounds can be use separately to couple with fluorescent dyes to study the energy transfer behavior of the fluorogen.

Example 10

Synthesis of SKC732

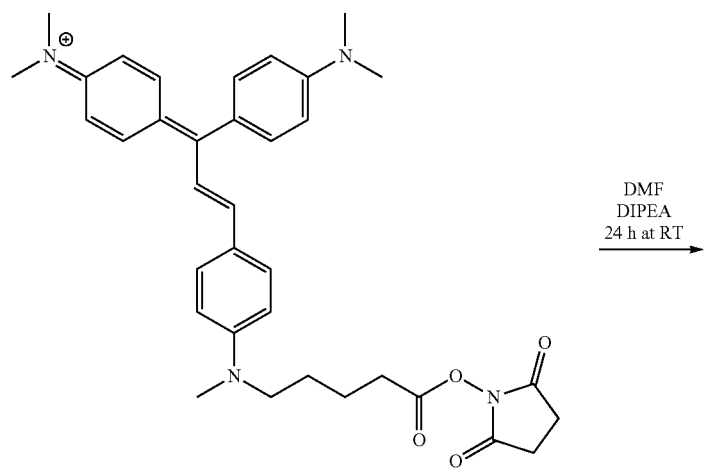

Chemical Formula: $C_{35}H_{41}N_4O_4^+$
Exact Mass: 581.3122
Molecular Weight: 581.7239
SKC-722

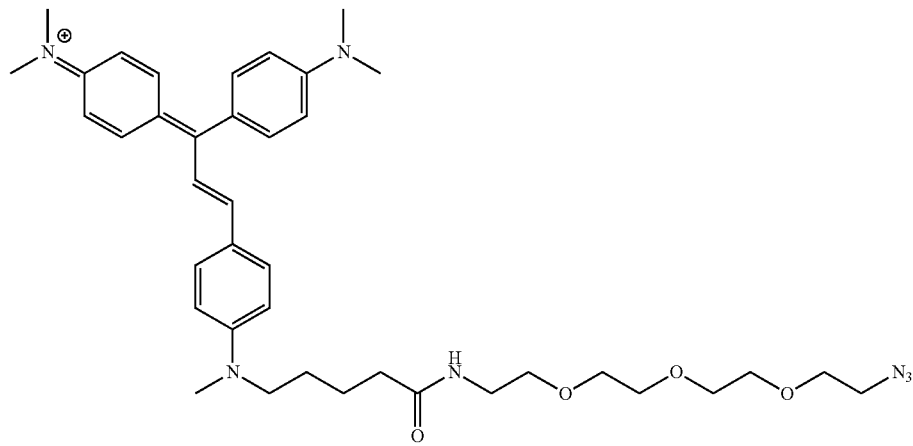

Chemical Formula: $C_{39}H_{54}N_7O_4^+$
Exact Mass: 684.4232
Molecular Weight: 684.8900
SKC-732

SKC722 (48 mg), 30 µl of 11-Azido-3,6,9-trioxaundecan-1-amine and 20 µl of DIPEA were dissolved in 2 ml of anhydrous DMF and stirred at room temperature for 24 hours. The mixture was concentrated under vacuum and purified by flash chromatography on $SiO_2$ using a 5% methanol in chloroform as the eluent to give 50 mg product. MW $C_{39}H_{54}N_7O_4^+$ 684.89 g/mol. (yield 88.5%). ESI-MS (+):684.52.

Example 11

Synthesis of SKC737

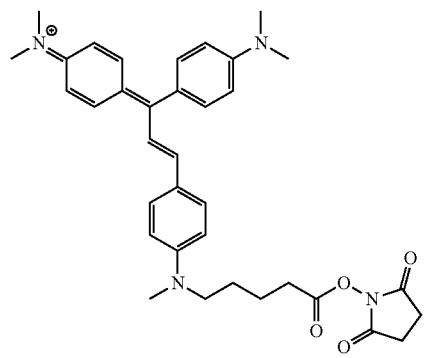

Chemical Formula: $C_{35}H_{41}N_4O_4^+$
Exact Mass: 581.3122
Molecular Weight: 581.7239
SKC-722

DMF
DIPEA
24 h at RT

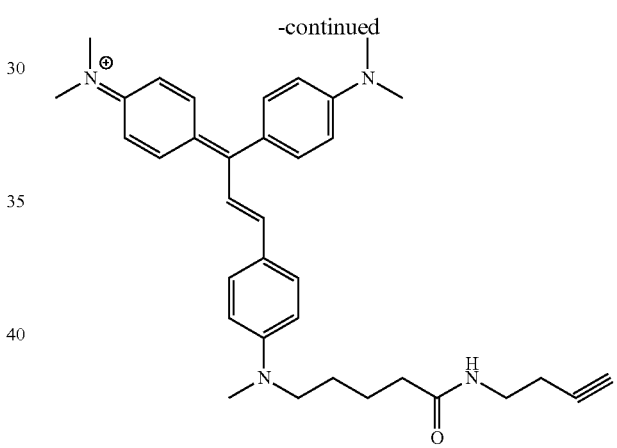

Chemical Formula: $C_{35}H_{43}N_4O^+$
Exact Mass: 535.3431
Molecular Weight: 535.7416
SKC-737

25.3 mg of SKC-722, 30 µl of 1-Amino-3-butyne and 20 µl of DIPEA were dissolved in 4 ml of anhydrous DMF and stirred at room temperature for 20 hours. The mixture was concentrated under vacuum and the residue was purified by flash chromatography on $SiO_2$ using a 20% methanol in chloroform as the eluent to give 23.2 mg of product. MW: $C_{35}H_{43}N_4O^+$ 535.74 g/mol (yield 100%). ESI-MS (+): 535.34

Example 12

Isolation of dL9.2 and dL9.5 from Mutagenized Libraries

A precursor FAP designated dL9 (SEQ. ID. NO. 1) was designed using the coding sequence of the light-chain from HL9-MG, a scFv originally isolated for binding and fluorescence activation of malachite green-based fluorogenic dyes (Szent-Gyorgyi, et al. 2008, incorporated herein by reference). This FAP was assembled as a tandem dimer of light chains by attaching a glycine-serine linker and a codon-optimized copy of the light chain gene to the original light chain via PCR. The gene sequence (SEQ. ID. NO. 4) (Table 4) encoding dL9 (SEQ. ID. NO. 1) (Table 3) was subjected to PCR-based random mutagenesis in order to isolate more stable variants of the encoded protein. Mutagenesis and library generation by electroporation was performed in a previously described manner (Chao, et al., Isolating and engineering human antibodies using yeast surface display, *Nature Protocols*, vol. 1, No. 2, pp. 755-768 (2006)), but screening employed the protein secretion vector pPNL9, rather than the surface display vector pPNL6: Individual *S. cerevisiae* expressing FAP mutants were incubated with cell-permeant fluorogen MG-ester and the brightest activators were cloned via flow cytometry. Clones were induced for FAP production in tryptone-based protein secretion media (Szent-Gyorgyi, et al. 2008) and media was screened for activation of MG-ester after five days of induction at 20° C. This screen yielded dL9.2 (SEQ. ID. NO. 2): a bright, stable FAP amenable to high levels of expression. Sequence analysis of this clone revealed a single amino acid change—valine 70 to alanine (V70A)—within the first light chain. This clone was found to fortuitously bind and activate fluorescence in the NIR fluorogen SKC602.

The V70A mutation was propagated to both light chains to produce dL9.3 (SEQ. ID. NO. 31), which was immediately subjected to mutagenesis and screening in the surface-display format described previously (Chao, et al., *Nature Protocols* (2006)) in the presence of SKC602. The brightest clone collected from this screen was designated dL9.5 (SEQ. ID. NO. 3), and sequencing described exactly two mutations—tyrosine 96 to histidine—on both light chains. Both proteins were found to also bind the NIR fluorogen SKC728, a derivative of SKC602.

Expression of dL9.2 (SEQ. ID. NO. 2) and dL9.5 (SEQ. ID. NO. 3) for the Purposes of Protein Purification.

A yeast expression and secretion plasmid based upon pPNL9 (http://www.sysbio.org/dataresources/ppnl9.txt), with nucleotides 789-903 replaced by the sequence gcaacgatagtgg (SEQ. ID. NO. 15), was generously provided by Dr. Christopher Szent-Gyorgyi for the purpose of facilitating the following cloning strategy. This pPNL9 variant shall hereon be referred to as pPNL9m. Primers dL9.1-pPNL9mF (TTGCT GCTAA AGAAG AAGGG GTATC TCTCG AGAAA AGAGA GGCTG AAGCT TCTTA CGAAT TAACA CAACC TCCAT CTGTT TCTGT TTCTC) (SEQ. ID. NO. 16) and dL9pPNL9Rev (CTCTA GGATC AGCGG GTTTA AACTC AATGG TGATG GTGAT GATGA CCGGT GGATA GTACG GTCAC CTTGG TCC) (SEQ. ID. NO. 17) were used to amplify dL9.2 (SEQ. ID. NO. 5) or dL9.5 (SEQ. ID. NO. 6) from the respective yeast surface display vectors pPNL6-dL9.2 and pPNL6-dL9.5. The resulting PCR amplicons were gel-extracted and purified using a commercial kit (PureLink Quick Gel Extraction Kit, Invitrogen). One microgram of CspCI-digested pPNL9m was combined with two micrograms of purified PCR amplicon (either dL9.2 (SEQ. ID. NO. 5) or dL9.5 (SEQ. ID. NO. 6)), and the mixture was electroporated into *S. cerevisiae* strain YVH10. Resulting colonies were selected for the ability to grow on SD/CAA agar plates supplemented with tryptophan (Szent-Gyorgyi C. et al., Fluorogen-activating single-chain antibodies for imaging cell surface proteins, *Nat Biotechnol*. 26:235-240, (2008)). Single colonies of YVH10 hosting the desired pPNL9-dL9.2 or pPNL9-dL9.5 plasmids were picked for protein production and purification in the manner described in Szent-Gyorgyi C. et al., Fluorogen-activating single-chain antibodies for imaging cell surface proteins, *Nat Biotechnol*. 26:235-240, (2008).

To facilitate ligase-dependent cloning methods, the above procedure was repeated for dL9.5 (SEQ. ID. NO. 6), using otherwise identical primers that appended BspEI (TCCGGA) (SEQ. ID. NO. 25) and BamHI (GGATCC) (SEQ. ID. NO. 26) sites directly at the 5' and 3' termini, respectively, of the dL9.5 gene (SEQ. ID. NO. 6). The resulting plasmid, designated pPNL9z-dL9.5, could be digested with BspEI (SEQ. ID. NO. 25) and BamHI (SEQ. ID. NO. 26) to produce a yeast expression vector backbone capable of receiving inserts with like-digested termini. Expression vectors pPNL9z-mL9.3 and pPNL9z-mL9.5 were produced by amplifying the respective monomers from plasmids pPNL6-dL9.2 and pPNL6-dL9.5 using primers p9zmL9XFw (AAGCT TCCGG ATCTT ACGAA TTAAC ACAAC CTCCA TCTG) (SEQ. ID. NO. 27) and p9zmL9XRv (TGATG GGATC CAGAC AAAAC AGTAA CTTTA GTACC ACCAC) (SEQ. ID. NO. 28). The amplicons were digested with BspEI (SEQ. ID. NO. 25) and BamHI (SEQ. ID. NO. 26) (New England Biolabs), purified by PCR cleanup kit (Qiagen), and ligated into the pPNL9z vector backbone. Ligation mixtures were used to transform *E. coli* (NEB10β) by heat-shock, from which single clones were sequenced to verify plasmid identity. Upon verification, purified stocks of each plasmid were introduced into YVH10 via electroporation. Transformed cells were grown in 10.0 mL SD/CAA supplemented with tryptophan for 48 hours (30° C., 300 RPM/0.75" shaking). Grown cells were collected by centrifugation (4° C., 2400×G, 3') and induced in the manner described for production of dL9.2 (SEQ. ID. NO. 2) and dL9.5 (SEQ. ID. NO. 3) at a smaller scale of 24 mL. The cultures were grown (20° C., 300 RPM/0.75" shaking) for 96 hours prior to harvesting: cells were pelleted by centrifugation (0° C., 22789×G, 20'), and the supernatant was collected and filtered (PES, 0.22 μm syringe-driven). Each protein supernatant was concentrated to 5.0 mL by centrifugation (Amicon Ultra-4 10 kDa MWCO filter unit, Millipore) in accordance with manufacturer-supplied recommendations. NiNTA-agarose beads (Qiagen, 250 μL) in 5.0 mL Wash Buffer (50 mM Tris pH 7.4, 500 mM NaCl, 20 mM imidazole pH 8.0, 5% glycerol) were applied to each concentrated protein solution, and the suspensions were incubated on a rocker (4° C., 1 hour) to allow protein binding. The beads were then centrifuged and washed with 50 mL Wash Buffer. The beads were transferred to DNA miniprep columns (Qiagen) and spun briefly on a bench top microcentrifuge to eliminate excess Wash Buffer. Elution Buffer (Wash Buffer with 250 mM imidazole, 800 μL) was applied over the beads. Liberated protein was then collected by centrifugation (4° C., 300×G, 5') into microcentrifuge tubes, yielding approximately 600 μL of 400 μM protein in both cases. Samples for spectral characterization were prepared by combining 300 μL of each protein with 2190 μL PBS, pH 7.4. Fluorogen (SKC602 and SKC728) was added to a final concentration of approximately 300 nM in each cuvette to produce samples of mL9.3: SKC602 (SEQ. ID. NO. 20:SKC602), mL9.3:SKC728 (SEQ. ID. NO. 20:SKC728), mL9.5:SKC602 (SEQ. ID. NO. 21:SKC602), and mL9.5:SKC728 (SEQ. ID. NO. 21:SKC728). Excitation and emission spectra were obtained by scanning samples on a Quantamaster™ fluorometer (PTI) equipped with dual monochromators on both excitation and emission paths. Slits were adjusted to 3.0 mm. Samples were scanned, with spectral corrections, at 1.0 nm intervals with 0.5 second integration. Three sequential scans were averaged. Values were subtracted from a PBS blank, and normalized to the maximum intensity within each scan. Results were plotted in Microsoft Excel to produce FIG. 11.

Plasmids pPNL6-mL9.3 and pPNL6-mL9.5 for yeast cell surface display were produced by PCR amplification of mL9.3 (SEQ. ID. NO. 23) and mL9.5 (SEQ. ID. NO. 24) from pPNL6-dL9.2 and pPNL6-dL9.5, respectively, using primers pCTCON2F (CGACG ATTGA AGGTA GATAC CCATA CGACG TTCCA GACTA CGCTC TGCAG) (SEQ. ID. NO. 29) and p6 mL9XRv (TCTCG ATGCG GCCGC TTAAG ACAAA ACAGT AACTT TAGTA CCACC) (SEQ. ID. NO. 30). Amplicons were digested with NheI and NotI prior to ligation into a like-digested pPNL6 vector backbone. Ligated plasmids were transformed into E. coli (NEB 10β) by heat-shock, and plasmids from single colonies were sequenced to verify identity. Upon verification, purified stocks of each plasmid were introduced into S. cerevisiae strain JAR200 via electroporation. Transformed cells were induced in the manner described in Szent-Gyorgyi, et al. 2008 for 96 hours prior to imaging. Cells were adhered to concanavalin A-coated glass-bottom dishes (MatTek Corporation) for 10 minutes at room temperature. Non-adhered cells were cleared by washing gently with 1.5 mL PBS, pH 7.4. The sample was bathed in 1.5 mL fresh PBS, pH 7.4, and fluorogen (SKC602 or SKC728) was added to a final concentration of 100 nM. Images were collected after 10 minutes of incubation at room temperature on an Andor Revolution XD spinning disc confocal microscope equipped with a 60×1.49 NA oil immersion objective. Images of fluorescence (FIG. 12, NIR:794/160) were obtained by excitation with a 641 nm laser, and emission was collected through a 794/160 bandpass filter (Semrock) by an iXon3 EMCCD (DU897 BV). Plasmids pPNL6-mL9.3 and pPNL6-mL9.5 for yeast cell surface display were produced by PCR amplification of mL9.3 (SEQ. ID. NO. 23) and mL9.5 (SEQ. ID. NO. 24) from pPNL6-dL9.2 and pPNL6-dL9.5, respectively, using primers pCTCON2F (SEQ. ID. NO. 29) and p6 mL9XRv (SEQ. ID. NO. 30). Amplicons were digested with NheI and NotI prior to ligation into a like-digested pPNL6 vector backbone. Ligated plasmids were transformed into E. coli (NEB 10β) by heat-shock, and plasmids from single colonies were sequenced to verify identity. Upon verification, purified stocks of each plasmid were introduced into S. cerevisiae strain JAR200 via electroporation. Transformed cells were induced in the manner described in Szent-Gyorgyi, et al. 2008 for 96 hours prior to imaging. Cells were adhered to concanavalin A-coated glass-bottom dishes (MatTek Corporation) for 10 minutes at room temperature. Non-adhered cells were cleared by washing gently with 1.5 mL PBS, pH 7.4. The sample was bathed in 1.5 mL fresh PBS, pH 7.4, and fluorogen (SKC602 or SKC728) was added to a final concentration of 100 nM. Images were collected after 10 minutes of incubation at room temperature on an Andor Revolution XD spinning disc confocal microscope equipped with a 60×1.49 NA oil immersion objective. Images of fluorescence (FIG. 12, NIR:794/160) were obtained by excitation with a 641 nm laser, and emission was collected through a 794/160 bandpass filter (Semrock) by an iXon3 EMCCD (DU897 BV).

The peptide sequence of each clone is described in Table 3 below. The residues where the deviations between the parent FAP sequence (dL9, SEQ. ID. NO. 1) and the subsequent generation sequences (dL9.2, SEQ. ID. NO. 2 and dL9.5, SEQ. ID. NO. 3) occur are underlined. The glycine-serine linker between light chains of SEQ. ID. Nos. 1, 2, and 3 is italicized and in bold face type. The nucleotide sequence encoding the parent FAP (dL9, SEQ. ID. NO. 4) as well as dL9.2 (SEQ. ID. NO. 5) and dL9.5 (SEQ. ID. NO. 6) and mL9.39 (SEQ. ID. NO. 23) and mL9.5 (SEQ. ID. NO. 24) are provided in Table 4, with a labeling scheme congruent with that used in Table 3.

TABLE 3

| Designation | Peptide Sequence |
| --- | --- |
| dL9<br>SEQ. ID.<br>NO. 1 | SYELTQPPSVSVSPGQTARITCSGDALPKQYTYWYQQKAGQAPVLVIYKDTER<br>PSGIPERFSGTSSGTTVTLTISGVQAEDEADYYCQSADSSGSYVFFGGGTKVTV<br>LS*GGGGPGGGSGGGSGGGSGGG*SYELTQPPSVSVSPGQTARITCSGDALPKQY<br>TYWYQQKAGQAPVLVIYKDTERPSGIPERFSGTSSGTTVTLTISGVQAEDEADY<br>YCQSADSSGSYVFFGGGTKVTVLS |
| dL9.2<br>SEQ. ID.<br>NO. 2 | SYELTQPPSVSVSPGQTARITCSGDALPKQYTYWYQQKAGQAPVLVIYKDTER<br>PSGIPERFSGTSSGTTATLTISGVQAEDEADYYCQSADSSGSYVFFGGGTKVTV<br>LS*GGGGPGGGSGGGSGGGSGGG*SYELTQPPSVSVSPGQTARITCSGDALPKQY<br>TYWYQQKAGQAPVLVIYKDTERPSGIPERFSGTSSGTTVTLTISGVQAEDEADY<br>YCQSADSSGSYVFFGGGTKVTVLS |
| dL9.5<br>SEQ. ID.<br>NO. 3 | SYELTQPPSVSVSPGQTARITCSGDALPKQYTYWYQQKAGQAPVLVIYKDTER<br>PSGIPERFSGTSSGTTATLTISGVQAEDEADYYCQSADSSGSHVFFGGGTKVTV<br>LS*GGGGPGGGSGGGSGGGSGGG*SYELTQPPSVSVSPGQTARITCSGDALPKQY<br>TYWYQQKAGQAPVLVIYKDTERPSGIPERFSGTSSGTTATLTISGVQAEDEADY<br>YCQSADSSGSHVFFGGGTKVTVLS |
| mL9.3<br>SEQ. ID.<br>NO. 20 | SYELTQPPSVSVSPGQTARITCSGDALPKQYTYWYQQKAGQAPVLVIYKDTER<br>PSGIPERFSGTSSGTTATLTISGVQAEDEADYYCQSADSSGSYVFFGGGTKVTV<br>LS |
| mL9.5<br>SEQ. ID.<br>NO. 21 | SYELTQPPSVSVSPGQTARITCSGDALPKQYTYWYQQKAGQAPVLVIYKDTER<br>PSGIPERFSGTSSGTTATLTISGVQAEDEADYYCQSADSSGSHVFFGGGTKVTV<br>LS |

TABLE 4

| Designation | Nucleotide sequence |
|---|---|
| dL9<br>SEQ. ID.<br>NO. 4 | TCTTACGAATTAACACAACCTCCATCTGTTTCTGTTTCTCCAGGTCAA<br>ACTGCTAGAATTACTTGTTCTGGTGATGCTTTGCCAAAACAATACAC<br>TTACTGGTATCAACAAAAAGCTGGTCAAGCTCCAGTTTTGGTTATTT<br>ATAAAGATACTGAAAGACCATCTGGTATTCCAGAAAGATTCTCAGGT<br>ACTTCTTCTGGTACTACT<u>GTT</u>ACTTTGACTATTTCTGGTGTTCAAGCT<br>GAAGATGAAGCTGATTATTATTGTCAATCTGCTGATTCTTCTGGTTCT<br>TATGTATTTTTCGGTGGTGGTACTAAAGTTACTGTTTTGTCTGGT*GGTGGA<br>GGAGGCCCAGGTGGCGGTTCAGGTGGAGGTTCTGGCGGAGGTTCTGG<br>TGGAGGT*TCCTATGAGTTGACTCAGCCACCCTCGGTGTCAGTGTCCC<br>CAGGACAGACGGCCAGGATCACCTGCTCTGGAGATGCATTGCCAAA<br>GCAATATACTTATTGGTACCAGCAGAAGGCAGGCCAGGCCCCTGTCT<br>TGGTGATATATAAAGACACTGAGAGGCCCTCAGGGATCCCTGAGCG<br>ATTCTCTGGTACCAGTTCAGGGACAACAGTCACATTGACCATCAGTG<br>GAGTCCAGGCAGAAGACGAGGCTGACTATTACTGTCAATCAGCAGA<br>CAGCAGTGGTTCCTATGTTTTCTTCGGCGGAGGGACCAAGGTGACCG<br>TACTATCC |
| dL9.2<br>SEQ. ID.<br>NO. 5 | TCTTACGAATTAACACAACCTCCATCTGTTTCTGTTTCTCCAGGTCAA<br>ACTGCTAGAATTACTTGTTCTGGTGATGCTTTGCCAAAACAATACAC<br>TTACTGGTATCAACAAAAAGCTGGTCAAGCTCCAGTTTTGGTTATTT<br>ATAAAGATACTGAAAGACCATCTGGTATTCCAGAAAGATTCTCAGGT<br>ACTTCTTCTGGTACTACT<u>GCT</u>ACTTTGACTATTTCTGGTGTTCAAGCT<br>GAAGATGAAGCTGATTATTATTGTCAATCTGCTGATTCTTCTGGTTCT<br>TATGTATTTTTCGGTGGTGGTACTAAAGTTACTGTTTTGTCT*GGTGGA<br>GGAGGCCCAGGTGGCGGTTCAGGTGGAGGTTCTGGCGGAGGTTCTGG<br>TGGAGGT*TCCTATGAGTTGACTCAGCCACCCTCGGTGTCAGTGTCCC<br>CAGGACAGACGGCCAGGATCACCTGCTCTGGAGATGCATTGCCAAA<br>GCAATATACTTATTGGTACCAGCAGAAGGCAGGCCAGGCCCCTGTCT<br>TGGTGATATATAAAGACACTGAGAGGCCCTCAGGGATCCCTGAGCG<br>ATTCTCTGGTACCAGTTCAGGGACAACAGTCACATTGACCATCAGTG<br>GAGTCCAGGCAGAAGACGAGGCTGACTATTACTGTCAATCAGCAGA<br>CAGCAGTGGTTCCTATGTTTTCTTCGGCGGAGGGACCAAGGTGACCG<br>TACTATCC |
| dL9.5<br>SEQ. ID.<br>NO. 6 | TCTTACGAATTAACACAACCTCCATCTGTTTCTGTTTCTCCAGGTCAA<br>ACTGCTAGAATTACTTGTTCTGGTGATGCTTTGCCAAAACAATACAC<br>TTACTGGTATCAACAAAAAGCTGGTCAAGCTCCAGTTTTGGTTATTT<br>ATAAAGATACTGAAAGACCATCTGGTATTCCAGAAAGATTCTCAGGT<br>ACTTCTTCTGGTACTACTGCTACTTTGACTATTTCTGGTGTTCAAGCT<br>GAAGATGAAGCTGATTATTATTGTCAATCTGCTGATTCTTCTGGTTCT<br><u>CAT</u>GTATTTTTCGGTGGTGGTACTAAAGTTACTGTTTTGTCTGGT*GGTGGA<br>GGAGGCCCAGGTGGCGGTTCAGGTGGAGGTTCTGGCGGAGGTTCTGG<br>TGGAGGT*TCCTATGAGTTGACTCAGCCACCCTCGGTGTCAGTGTCCC<br>CAGGACAGACGGCCAGGATCACCTGCTCTGGAGATGCATTGCCAAA<br>GCAATATACTTATTGGTACCAGCAGAAGGCAGGCCAGGCCCCTGTCT<br>TGGTGATATATAAAGACACTGAGAGGCCCTCAGGGATCCCTGAGCG<br>ATTCTCTGGTACCAGTTCAGGGACAAC<u>AGCC</u>ACATTGACCATCAGTG<br>GAGTCCAGGCAGAAGACGAGGCTGACTATTACTGTCAATCAGCAGA<br>CAGCAGTGGTTCC<u>CAC</u>GTTTTCTTCGGCGGAGGGACCAAGGTGACCG<br>TACTATCC |
| mL9.3<br>SEQ. ID.<br>NO. 23 | TCTTACGAATTAACACAACCTCCATCTGTTTCTGTTTCTCCAGGTCAAACTG<br>CTAGAATTACTTGTTCTGGTGATGCTTTGCCAAAACAATACACTTACTGGTA<br>TCAACAAAAAGCTGGTCAAGCTCCAGTTTTGGTTATTTATAAAGATACTGA<br>AAGACCATCTGGTATTCCAGAAAGATTCTCAGGTACTTCTTCTGGTACTACT<br><u>GCT</u>ACTTTGACTATTTCTGGTGTTCAAGCTGAAGATGAAGCTGATTATTATT<br>GTCAATCTGCTGATTCTTCTGGTTCT<u>TAT</u>GTATTTTTCGGTGGTGGTACTAA<br>AGTTACTGTTTTGTCT |
| mL9.5<br>SEQ. ID.<br>NO. 24 | TCTTACGAATTAACACAACCTCCATCTGTTTCTGTTTCTCCAGGTCAAACTG<br>CTAGAATTACTTGTTCTGGTGATGCTTTGCCAAAACAATACACTTACTGGTA<br>TCAACAAAAAGCTGGTCAAGCTCCAGTTTTGGTTATTTATAAAGATACTGA<br>AAGACCATCTGGTATTCCAGAAAGATTCTCAGGTACTTCTTCTGGTACTACT<br><u>GCT</u>ACTTTGACTATTTCTGGTGTTCAAGCTGAAGATGAAGCTGATTATTATT<br>GTCAATCTGCTGATTCTTCTGGTTCT<u>CAT</u>GTATTTTTCGGTGGTGGTACTAA<br>AGTTACTGTTTTGTCT |

Example 13

Determination of Fluoromodule Fluorescence Quantum Yield

Relative fluorescence quantum yield assessments were conducted via the gradient method (Williams, Winfield and Miller, Relative Fluorescent Quantum Yield Using a Computer-controlled Luminescence Spectrometer, *Analyst*, vol. 108, 1067-1071 (1083) against reference dyes Cy5.18 in PBS, pH 7.4 (Mujumdar, et al., Cyanine Dyes Labeling Reagents: Sulfoindocyanine Succinimidyl Esters, *Bioconjugate Chemistry*, Vol. 4, No. 2, 105-111 (1993) and oxazine-1 in absolute ethanol (Worth, et al., Integrating Sphere Setup for the Traceable Measurement of Absolute Photoluminescence Quantum Yields in the Near Infrared, *Analytical Chemistry*, 84, 1345-1352 (2012). Fluoromodules were formed by combining a quantity of fluorogen (SKC602 or SKC728) at least 20-fold above the fluoromodule dissociation constant with a molar excess of purified FAP (dL9.2 (SEQ. ID. NO. 2) or dL9.5 (SEQ. ID. NO. 3)). The solutions were incubated at 4° C. with rocking for at least one hour prior to measurements in order to ensure complete complex formation. The optical path length for all sample measurements was 1.00 cm, and all solutions were at room temperature during measurement. Absorbance measurements were taken using a PerkinElmer Lambda 45 UV/VIS spectrometer, while fluorescence emission spectra were measured using a Quantamaster fluorometer equipped with dual excitation and emission monochromators (Photon Technology International). Fluorescence emission was integrated using Spekwin32 (Menges 2013, http://www.effemm2.de/spekwin/spekwin_copyright/de.html. Linear fits and quantum yield ratios were calculated in Microsoft Excel 2013.

Example 14

Assessment of Fluoromodule Activity with Respect to pH

A set of titrating buffers occupying pH values from 2.0 to 10.0 in 0.5 unit increments was prepared at room temperature in accordance to a published recipe (Carmody, An Easily Prepared Wide Range Buffer Series, *Journal of Chemical Education*, Vol. 38, No. 11, pp. 559-560 (1961)) adjusted to accommodate sodium chloride at a concentration of 300 mM. Fluoromodules consisting of dL9.5 bound to SKC602 were prepared by addition of 16.7 µL HPLC-purified SKC602 (300 µM stock in EtOH/5% acetic acid) to 1.30 mL Buffer (10.0 mM Tris, pH 8.0 at RT, supplemented with 300 mM NaCl). Purified dL9.5 was added (1.5 mL, approximately 50 µM stock) and incubated at 4° C. for 90 minutes. Twenty microliters of this solution was combined with 180 µL of titrating buffer (five replicate samples per pH increment) in wells of a Costar® 96-well Tray (Corning Incorporated, Product 3596) and incubated for approximately three hours in absence of light. Fluorescence was then measured using a TECAN Infinite M1000 plate reader with 695/10 nm excitation and 735/10 nm emission windows at a gain of 111. Data was processed in Microsoft Excel 2010: The mean fluorescence intensity value for each pH increment was calculated, and all mean values were divided by the maximum mean intensity in order to normalize fluorescence intensities measured across the entire pH range to a value of 1.0. Extreme values within each set of five replicates calculated to a percentage of the mean for each pH increment in order to indicate the degree of variation across replicate reads. Fluoromodule stability was further assessed by repeating reads with the stated settings every minute for a total duration of one hour, during which the mean fluorescence in each pH solution failed to change more than 3% (data not shown).

Example 15

Production of Stable FAP-Expressing Mammalian Cell Lines

HEK293 Plasma Membrane Exterior.

Genes encoding dL9.2 and dL9.5 (SEQ. ID. NOs. 5 and 6, respectively) were fused to a 5' linker encoding a start codon and Igκ secretion peptide via PCR. These products were then fused in-frame and upstream of DNA encoding a truncated scaffold derived from a C-terminal fragment (Proline 237 to end) of murine CD80 (Chou, et al., Expression of Chimeric Monomer and Dimer Proteins on the Plasma Membrane of Mammalian Cells, *Biotechnology and Engineering*, vol. 65, No. 2, (1999) to yield membrane-targeted and tethered expression cassettes. The cassette was flanked by NheI and XmaI restriction sites and cloned into pEGFP-C2 (Clontech) in place of eGFP, producing plasmids pOIdL9.2N (SEQ. ID. NO. 7) and pOIdL9.5N (SEQ. ID. NOs.: 8). See FIGS. 9A through 9D. HEK293 cells were transfected with purified plasmid DNA using Fugene 6 (Roche) in accordance with manufacturer-supplied recommended protocols. Transfected cells were selected by propagation in media (DMEM/10% BS) supplemented with G418 for 12 days, and survivors were cloned by flow cytometry in the presence of MG-2p. Cloned single cells were re-propagated to establish stable cell lines with largely homogeneous FAP expression.

HEK293 Cytoplasmic eGFP Fusion.

The gene was modified from the above vector by deletion of the Igκ secretion signal, and substitution of a glycine-rich linker comprised of the amino acid sequence GGR ASG GGA SGG GSG GSG (SEQ. ID. NO. 14), followed by eGFP in place of the murine CD80 membrane anchoring scaffold to produce plasmids pCYdL9.2eGFP (SEQ. ID. NO. 9) and pCYdL9.5eGFP (SEQ. ID. NO. 10). Cloning of stable HEK293 cell lines expressing the cytoplasmic FAPs via flow cytometry was based on activation of SKC602 rather than MG-2p.

HEK293 Mitochondrial eGFP Fusion.

The gene for dL9.5 (SEQ. ID. NO. 6) plasma membrane display was modified by replacement of the Igκ secretion signal with a mitochondrial localization signal derived from human cytochrome c oxidase subunit 4 (encoding the peptide sequence MLATRVFSLVGKRAISTSVCVRAEESR, SEQ. ID. NO. 18). In the course of adapting the gene (SEQ. ID. NO. 6) encoding dL9.5 (SEQ. ID. NO. 3) for constructing the mitochondrial expression vector, the first and fourth codons were modified (1: TCT to AGC, 4: TTA to CTG) in order to optimize for expression in mammalian cells. The linked eGFP was adapted directly from the cytoplasmic eGFP fusion construct in order to yield plasmid pMTdL9.5eGFP (SEQ. ID. NO. 11). Cloning of HEK293 cells transfected with this vector in the previously described manner was performed via flow cytometry, based on activation of SKC602.

HCT116 Plasma Membrane Exterior.

A lentiviral vector backbone, pLenti-CaMKIIa-hChR2 (E123T-H134R)-EYFP, (Gunaydin, et al., *Nat. Neurosci.*, (3): 387-392 (2010)) was adapted for FAP expression by excision of the entire viral payload—CaMKIIa promoter, channelrhodopsin, and eYFP—between PacI and EcoRI restriction sites. Into this site was cloned (5'-3'): The promoter and open reading frame from the previously described plasma membrane-targeting constructs (for both dL9.2 and dL9.5), the internal ribosome entry site (IRES) from pQCXIP (Clontech), and a separate open reading frame encoding eGFP. The vectors produced by these modifications were designated pLenCMVdL9.2NIG (SEQ. ID. NO. 12) and pLenCMVdL9.5NIG (SEQ. ID. NO. 13). Viral particles were produced by collaborators for transduction of HCT116 to generate transgene-expressing tumor models.

Example 16

Assessment of Fluorogen Membrane Permeance by Flow Cytometry

An HEK293 cell line stably expressing dL9.5-eGFP (SEQ. ID. NO. 3-eGFP) was propagated to 90% confluence in two 100 mm tissue culture dishes. Cells were lifted by application of Cellstripper™ (Mediatech Inc.) and transferred to two 5.0 mL cell culture tubes on ice. The baseline population fluorescence (labeled PRE, excitation: 633 nm, emission: 755/75 nm) was assessed by collection of 20000 events on a Becton Dickinson FACSVantage SE flow cytometer with FACSDiVa option. Fluorogen (SKC602 and SKC728) was applied as a droplet above each cell suspension to yield 100 nM after mixing, and then fitted to the flow cytometer sample holder. A brief vortexing pulse was applied by the sample holder in order to mix fluorogen with the cells as data acquisition for Time 0 was started. Population fluorescence was acquired every 10 minutes after Time 0 for one hour, with acquisition durations typically lasting 90 seconds in order to scan 20000 events. The mean fluorescence intensity from eGFP and FAP double-positive cells was calculated using BD FACSDiVa acquisition software and plotted as mean population emission intensities (on a logarithmic scale) vs. Time.

Example 17

Imaging of HEK293 Stable Cell Lines Expressing dL9.5 (SEQ. ID. NO. 3) in Various Cellular Contexts For all imaging experiments, unbound fluorogen was not washed away prior to image acquisition.

CYTOPLASM. HEK293 cells were transfected with, and stably expressing the pCYdL9.5eGFP vector, were thawed from a cryostock and maintained in DMEM/10% FBS for four passages prior to fluorescence imaging procedures. Immediately prior to imaging, growth media was exchanged for HBSS (pH 7.4) supplemented with SKC602 (200 nM final concentration). The cells were allowed to recover at 37° C. with 5% $CO_2$ for 20-30 minutes, and fluoromodule activity under in vivo conditions within the cytoplasm was imaged using an Andor Revolution XD spinning disk confocal microscope (60×1.49 NA oil immersion objective, excitation at 640 nm, emission in far-red: 685/70 filter, and NIR: 794/160 filter). The same cells were also imaged for eGFP activity (excitation at 488 nm, emission via 525/50 nm filter). A single imaging field representative of what one may observe under the prescribed conditions is shown in FIG. 5. The DIC channel shows all cells in the field of view under white light illumination (no fluorescence). The eGFP channel shows fluorescence as observed from the eGFP molecule covalently attached to every expressed FAP, with some cells exhibiting greater overall protein expression (brighter) than other cells in the field of view. The Red channel shows fluorescence emission from the fluoromodule as detected through an emission filter that passes light of wavelengths between 650 and 720 nm—as shown in FIG. 2, the NIR emitting FAPs emit a small portion of light that falls within this range. The NIR channel shows NIR fluorescence emission from the fluoromodule as detected through an emission filter that passes light of wavelengths between 714 and 874 nm. In accordance with the fluoromodule emission spectrum shown in FIG. 2, this emission filter allows the microscope camera to detect a large portion of the fluoromodule emission, and consequently, the observed signal appears brighter. One must note that intensities cannot be directly compared between channels, due to considerations non-exclusively including: differences in excitation light intensities, exposure and capture times, the transmission profile of each emission filter, and the quantum efficiency of the iXON3 DU897 (back-illuminated) camera across the range of emitted wavelengths. An evenly distributed fluorescence signal is observed in these cells, with no bright foci that would indicate protein aggregation, and the fluoromodule signal intensity scales with that of eGFP.

PLASMA MEMBRANE. The imaging protocol and conditions were similar to those applied to assess cytoplasmic fluoromodule activity; SKC728 was used in place of SKC602 at 100 nM, and eGFP imaging was omitted. As seen in FIG. 6, NIR fluorescence indicates FAP present on the plasma membrane of the cell, and does not reveal the portion of fully synthesized FAP in the endoplasmic reticulum and Golgi compartments, which cannot be accessed by SKC728.

MITOCHONDRIA. The imaging protocol and conditions were similar to those applied to assess cytoplasmic fluoromodule activity, but transiently transfected cells were used with 50 nM SKC602; eGFP imaging was omitted. FIG. 6 shows that dL9.5 (SEQ. ID. NO. 3) remains competent to form fluoromodules upon addition of a cell-permeant fluorogen such as SKC602, even after being imported through a dual membrane enclosed compartment such as the mitochondrial matrix. Taken together, images in FIG. 6 demonstrate the ability to target the FAP to specific subcellular locations. Also shown is that the physical properties of the fluorogen, may be used to specify additional targeting constraints.

Example 18

Application of NIR Fluoromodules Towards In Vivo Imaging within a Mouse Model

Figure 7:
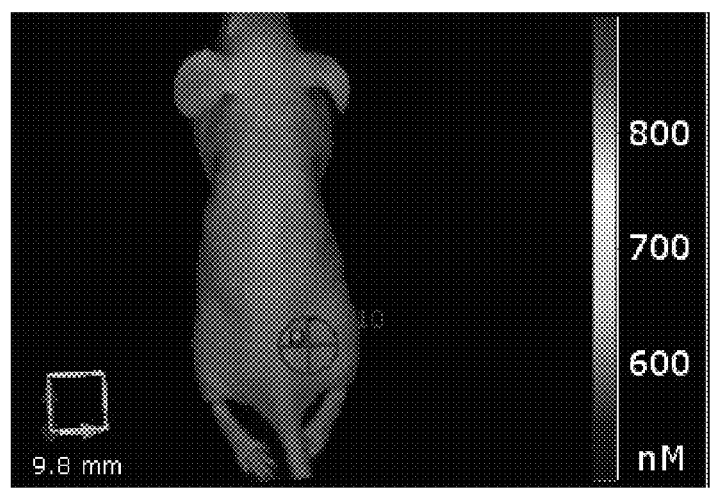
FIG. 7 shows that 100 cells expressing cytoplasmic dL9.5-eGFP (SEQ. ID. NO. 3:eGFP) and pre-labeled with SKC602 can be easily visualized via NIR fluorescence after subcutaneous injection into mice.

SUBCUTANEOUS DETECTION LIMIT. An FMT2500LX instrument (VisEN, now PerkinElmer) was calibrated for quantitative fluoromodule measurement (excitation at 670 nm, emission collected from 690-740 nm) using solutions of purified protein and fluorogen at defined concentrations. HEK293 cells stably expressing the cytoplasmic dL9.5-eGFP (SEQ. ID. NO. 3-eGFP) fusion protein were labeled by application of SKC602 to a final concentration of 200 nM. Different numbers of pre-labeled cells ($1 \times 10^5 - 1 \times 10^2$) as well as unlabeled controls were then mixed with chilled Matrigel (BD Biosciences) and injected subcutaneously into nude mice. The animals were imaged 24 hours after cell implantation using the FMT2500LX in order to determine the lowest detectable number of cells. A representative image of fluorescence from a mouse injected subcutaneously with $1 \times 10^2$ pre-labeled cells is shown in FIG. 7, along with corresponding concentration scale (color represents calculated concentration per voxel based upon previously described calibration).

Fluorescence detection of FAP-expressing cells in the intraperitoneal cavity. Unlabeled HCT116 cells transduced by the dL9.2 (SEQ. ID. NO. 2)-delivering lentivirus (approximately $7 \times 10^6$) were injected into the intraperitoneal cavity of nude mice (a non-injected control was run in parallel). Following two hours of recovery, fluorogens SKC602 or SKC728 were administered intravenously (100 µL maximum injection volume per animal, 4.0 µM fluorogen stock in PBS, pH 7.4). Animals were allowed 20 hours to recover prior to imaging by the FMT2500LX instrument using the previously mentioned fluorescence channel. The resulting data, represented in part in FIG. 8, demonstrates that unlabeled FAP-expressing cells can be injected deep into mice, and labeled post-injection by intravenous administration of fluorogen. The labeled FAPs, upon excitation by a 670 nm laser, emit NIR fluorescence that can be detected through a 715/50 (690-740 nm) emission filter from deep within the mice.

These examples show a substantial improvement over previously described far-red/NIR fluorescent proteins in terms of brightness, wavelength, and flexibility by leveraging the flexibility of synthetic chemistry to produce novel chromophores.

The present invention has been described in accordance with several examples, which are intended to be illustrative in all aspects rather than restrictive. Thus, the present invention is capable of many variations in detailed implementation, which may be derived from the description contained herein by a person of ordinary skill in the art.

All patents, patent applications, publications, or other disclosure material mentioned herein, are hereby incorporated by reference in their entirety as if each individual reference was expressly incorporated by reference respectively. All references, and any material, or portion thereof, that is said to be incorporated by reference herein are incorporated herein only to the extent that the incorporated material does not conflict with existing definitions, statements, or other disclosure material set forth in this disclosure. As such, and to the extent necessary, the disclosure as set forth herein supersedes any conflicting material incorporated herein by reference and the disclosure expressly set forth in the present application controls.

The present invention has been described with reference to various exemplary and illustrative embodiments. The embodiments described herein are understood as providing illustrative features of varying detail of various embodiments of the disclosed invention; and therefore, unless otherwise specified, the features, elements, components, constituents, ingredients, structures, modules, and/or aspects of the disclosed embodiments may be combined, separated, interchanged, and/or rearranged without departing from the scope of the disclosed invention. Accordingly, it will be recognized by persons having ordinary skill in the art that various substitutions, modifications or combinations of any of the exemplary embodiments may be made without departing from the scope of the invention. In addition, persons skilled in the art will recognize, or be able to ascertain using no more than routine experimentation, many equivalents to the various embodiments of the invention described herein upon review of this specification. Thus, the invention is not limited by the description of the various embodiments, but rather by the claims.

What is claimed is:

1. A composition comprising:

a fluorogen and a cognate fluorogen-activating peptide wherein, upon binding to the fluorogen-activating peptide, the fluorogen fluoresces having an emission peak in the near infrared region, the fluorogen having the structure

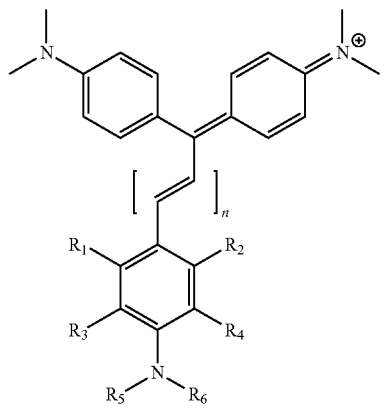

wherein $R_1, R_2, R_3, R_4,$ and $R_5$ are the same or different and are selected from H, Cl, Br, I, F, an electron donating group, or an electron withdrawing group;

$R_5$ and $R_6$ are the same or different and are selected from the group consisting of substituents that comprise one or more of hydrogen, alkyl groups, substituted alkyl groups, esters, aryl groups, substituted aryl groups, amines, amides, sulfonated groups, carboxylated groups, multiple hydroxy groups and substituents that can conjugate the fluorogen to another chemical species; and, n is an integer from 0 to 2;

wherein the fluorogen-activating peptide is selected from the group consisting of SEQ. ID. 20, SEQ. ID. 21, and a polypeptide sequence having at least 90% sequence identity to the polypeptide of SEQ. ID. NOs. 1, 2, and 3.

2. The composition recited in claim 1 wherein the fluorogen has the structure

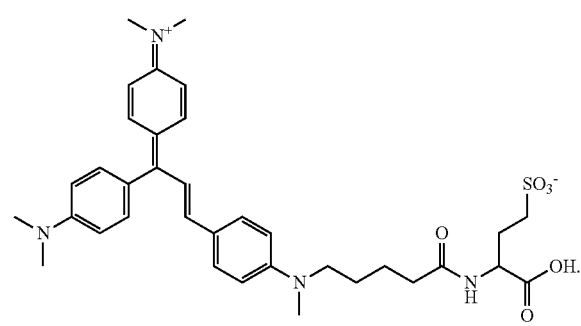

3. The composition recited in claim 1 wherein the fluorogen has the structure

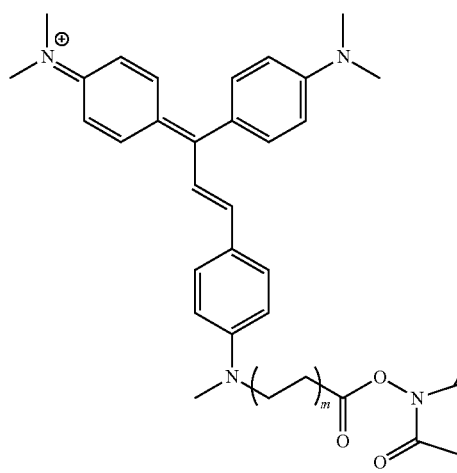

wherein m is an integer from 1 to 10.

4. The composition recited in claim 1 wherein the fluorogen has the structure

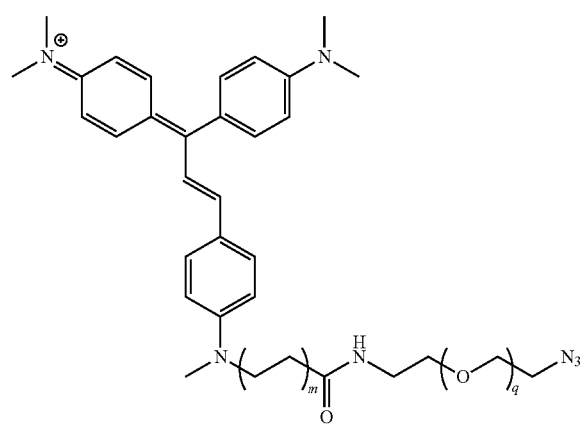

wherein m is an integer from 1 to 10 and q is an integer from 1 to 10.

5. The composition recited in claim 1 wherein the fluorogen is synthesized from compounds having the structure selected from

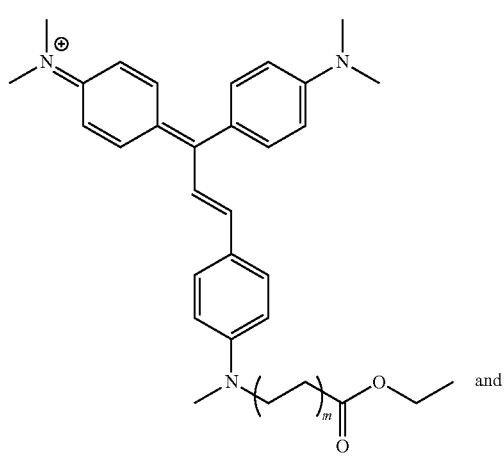

and

103

-continued

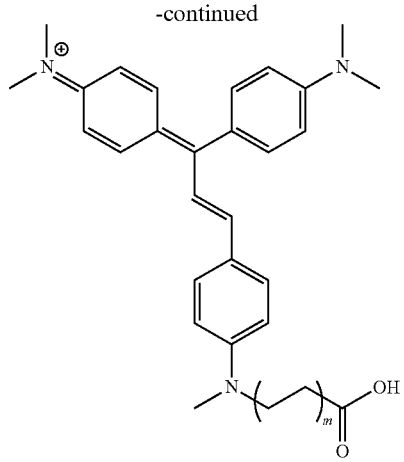

wherein m is an integer from 1 to 10.

6. The composition recited in claim 1 wherein the fluorogen has the structure

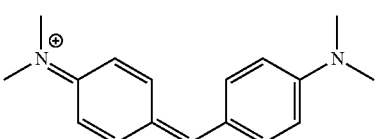

wherein m is an integer from 1 to 10.

7. A cognate ligand of a dye for non covalently binding in use, to the dye,
the cognate ligand comprising a fluorogen-activating peptide selected from the group consisting of SEQ. ID. 20, SEQ. ID. 21, and a polypeptide sequence having at least 90% sequence identity to the polypeptide selected from the group consisting of SEQ ID NOs: 1, 2, and 3;
the dye and ligand exhibiting, upon binding, a detectable fluorescence signal in the near infrared region of the spectrum;

104 wherein the dye has the structure

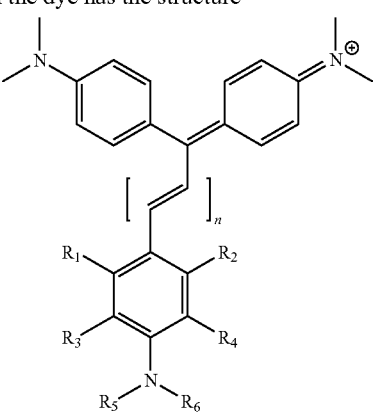

wherein $R_1$, $R_2$, $R_3$, $R_4$ and $R_5$ are the same or different and are selected from H, Cl, Br, I, F, an electron donating group, or an electron withdrawing group;
$R_5$ and $R_6$ are the same or different and are selected from substituents comprising one or more of hydrogen, alkyl groups, substituted alkyl groups, esters, aryl groups, substituted aryl groups, amines, amides, hydrophilic groups, and charged groups; and,
n is an integer from 0 to 2.

8. The cognate ligand recited in claim 4 wherein the dye has the structure

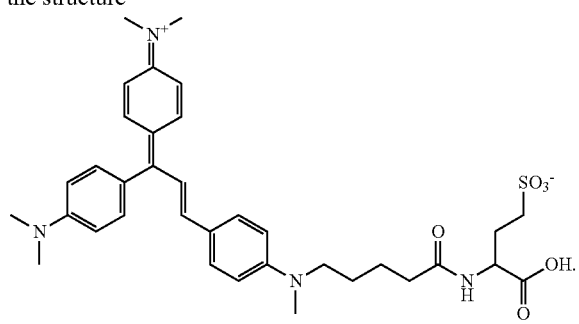

9. The cognate ligand recited in claim 4 wherein the dye has the structure

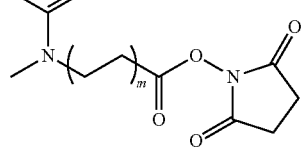

wherein m is an integer from 1 to 10.

10. The cognate ligand recited in claim 4 wherein the dye has the structure

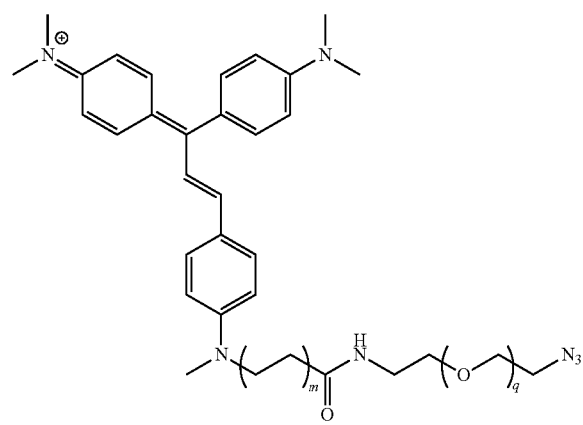

wherein m is an integer from 1 to 10 and q is an integer from 1 to 10.

11. The cognate ligand recited in claim 4 wherein the dye has the structure

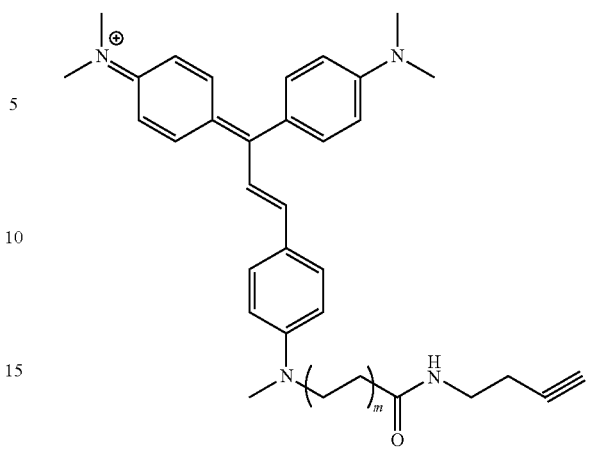

wherein m is an integer from 1 to 10.

12. A composition comprising:
a polypeptide selected from the group consisting of SEQ. ID. NO. 20 and SEQ. ID. NO.

13. A composition comprising:
a polypeptide selected from the group consisting of a sequence having at least 90% sequence identity to the amino acid sequence of SEQ. ID. NOs. 1, 2, and 3.

* * * * *

UNITED STATES PATENT AND TRADEMARK OFFICE
CERTIFICATE OF CORRECTION

PATENT NO. : 9,023,998 B2  
APPLICATION NO. : 13/920775  
DATED : May 5, 2015  
INVENTOR(S) : Chakraborty et al.

Page 1 of 1

It is certified that error appears in the above-identified patent and that said Letters Patent is hereby corrected as shown below:

In the Specification

In Column 1, Line 17, delete "5U54RR022241" and insert -- 5U54GM103529 --, therefor.

Signed and Sealed this  
Fifth Day of April, 2016

Michelle K. Lee  
*Director of the United States Patent and Trademark Office*